US009775881B2

(12) United States Patent
Bellovin et al.

(10) Patent No.: US 9,775,881 B2
(45) Date of Patent: Oct. 3, 2017

(54) METHODS OF TREATING MESOTHELIOMA BY ADMINISTRATION OF COMPOUNDS COMPRISING FGFR1 ECD

(71) Applicants: Five Prime Therapeutics, Inc., South San Francisco, CA (US); GlaxoSmithKline Intellectual Property (NO.2) Limited, Brentford, Middlesex (GB)

(72) Inventors: David Bellovin, South San Francisco, CA (US); Kevin Baker, Burlingame, CA (US); Thomas Brennan, Saratoga, CA (US); Arundathy Nirmalini Pandite, Research Triangle Park, NC (US); Bijoyesh Mookerjee, Collegeville, PA (US); Maurice P. DeYoung, Collegeville, PA (US); Rakesh Kumar, Collegeville, PA (US)

(73) Assignees: Five Prime Therapeutics, Inc., South San Francisco, CA (US); GlaxoSmithKline Intellectual Property (No.2) Limited, Brentford, Middlesex (GB)

(*) Notice: Subject to any disclaimer, the term of this patent is extended or adjusted under 35 U.S.C. 154(b) by 0 days.

(21) Appl. No.: 14/890,047

(22) PCT Filed: May 22, 2014

(86) PCT No.: PCT/US2014/039129
§ 371 (c)(1),
(2) Date: Nov. 9, 2015

(87) PCT Pub. No.: WO2014/190147
PCT Pub. Date: Nov. 27, 2014

(65) Prior Publication Data
US 2016/0106809 A1  Apr. 21, 2016

Related U.S. Application Data

(60) Provisional application No. 61/826,975, filed on May 23, 2013, provisional application No. 61/936,471, filed on Feb. 6, 2014, provisional application No. 61/974,279, filed on Apr. 2, 2014.

(51) Int. Cl.
A61K 38/17 (2006.01)
A61K 31/337 (2006.01)
C07K 14/71 (2006.01)
C12Q 1/68 (2006.01)
G01N 33/53 (2006.01)
G01N 33/574 (2006.01)
A61K 31/519 (2006.01)
A61K 31/555 (2006.01)
A61K 33/24 (2006.01)
A61K 45/06 (2006.01)

(52) U.S. Cl.
CPC .......... *A61K 38/179* (2013.01); *A61K 31/337* (2013.01); *A61K 31/519* (2013.01); *A61K 31/555* (2013.01); *A61K 33/24* (2013.01); *A61K 45/06* (2013.01); *C07K 14/71* (2013.01); *C12Q 1/6886* (2013.01); *G01N 33/574* (2013.01); *G01N 33/57496* (2013.01); *C07K 2319/30* (2013.01); *C12Q 2600/106* (2013.01); *C12Q 2600/158* (2013.01); *G01N 2333/49* (2013.01); *G01N 2333/50* (2013.01); *G01N 2333/503* (2013.01); *G01N 2333/515* (2013.01); *G01N 2800/52* (2013.01)

(58) Field of Classification Search
None
See application file for complete search history.

(56) References Cited

U.S. PATENT DOCUMENTS

| 8,951,972 | B2* | 2/2015 | Long | A61K 45/06 424/134.1 |
|---|---|---|---|---|
| 2006/0189679 | A1* | 8/2006 | Holton | A61K 31/137 514/449 |
| 2008/0171689 | A1 | 7/2008 | Williams et al. | |
| 2009/0004687 | A1 | 1/2009 | Mansfield et al. | |
| 2009/0105329 | A1* | 4/2009 | Chiao | A61K 31/167 514/449 |
| 2012/0128672 | A1 | 5/2012 | Keer | |
| 2012/0308562 | A1* | 12/2012 | Derynck | A61K 31/519 424/133.1 |

FOREIGN PATENT DOCUMENTS

| WO | 2007014123 A2 | 2/2007 |
|---|---|---|
| WO | 2012068030 A1 | 5/2012 |

OTHER PUBLICATIONS

Harding et al., Blockade of nonhormonal fibroblast growth factors by FP-1039 inhibits growth of multiple types of cancer. Science/Translational Medicine, 5, 178ra39, 2013.*
Huang et al. "Ectopic activity of fibroblast growth factor 1 in hepatocytes accelerates hepatocarcinogenesis by driving proliferation and vascular endothelial growth-induced angiogenesis" Cancer Research vol. 66(3): 1481-1490 (2006).
International Search Report and Written Opinion for PCT/US2014/039129 dated Dec. 22, 2014.
Bellovin, D. et al: "FP-1039/GSK3052230, an FGF ligand trap, enhances VEGF antagonist therapy in preclinical models of RCC and HCC", Jan. 1, 2014 URL:http://www.fiveprime.com/file.cfm/4/do cs/AACR Poster-Bellovin-Final.pdf.
(Continued)

Primary Examiner — Elly-Gerald Stoica
(74) Attorney, Agent, or Firm — McNeill Baur PLLC

(57) ABSTRACT

Methods of treating cancers comprising administering a fibroblast growth factor receptor 1 (FGFR1) extracellular domain (ECD) and/or an FGFR1 ECD fusion molecule are provided. Methods of treating cancers comprising administering a fibroblast growth factor receptor 1 (FGFR1) extracellular domain (ECD) and/or an FGFR1 ECD fusion molecule and at least one anti-angiogenic agent are provided.

19 Claims, 14 Drawing Sheets

(56) References Cited

OTHER PUBLICATIONS

Bellovin, D: "Abstract 5449: FP-1039/GSK3052230, an FGF ligand trap, enhances VEGF antagonist therapy in preclinical models of RCC and HCC" Cancer Research, 2014, 74(19) Suppl.
Cao R. et al, "Collaborative interplay between FGF-2 and VEGF-c promotes lymphangiogenesis and metastasis." Proc Natl Acad Sci USA., Sep. 11, 2012, vol. 109, No. 39, pp. 15894-15899.
European Search Report for EP14800459.1 issued Nov. 29, 2016.
Harding T.C. et al, "Blockade of nonhormonal fibroblast growth factors by FP-1039 inhibits growth of multiple types of cancer." Sci Trans Med., Mar. 27, 2013, vol. 5, No. 178, pp. 178ra39.
Harding T.C. et al, "Preclinical efficacy of fibroblast growth factor ligand trap HGS1036 in lung carcinoma models with genomic amplification of FGFR1" AACR Annual Meeting 2012, Poster.
Iwasaki A. et al, "Basic fibroblast growth factor (bFGF) and vascular endothelial growth factor (VEGF) levels as prognostic indicators in NSCLC." Eur J Cardiothorac Surg., Mar. 2004, vol. 25, No. 3, pp. 443-448.
Lieu C. et al, "Beyond VEGF: inhibition of the fibroblast growth factor pathway and antiangiogenesis." Clin Cancer Res., Sep. 27. 2011, vol. 17, No. 19, pp. 6130-6139.
Long L. et al, "Preclinical antitumor efficacy of FP-1039, a soluble FGF receptor 1:Fc conjugate, as a single agent or in combination with anticancer drugs." AACR 100th Annual Meeting 2009, Abstract.
Long L. et al, Abstract #2789: Antitumor efficacy of FP-1039, a soluble FGF receptor 1:Fc conjugate, as a single agent or in combination with anticancer drugs. Cancer Res., May 1, 2009, vol. 69, No. 9, Supplement.
Ogawa T. et al, "Anti-tumor angiogenesis therapy using soluble receptors: enhanced inhibition of tumor growth when soluble fibroblast growth factor receptor-1 is used with soluble vascular endothelial growth factor receptor." Cancer Gene Ther., Aug. 2002, vol. 9, No. 8, pp. 633-640.
Singapore search report and written opinion issued in Singapore Application No. 11201509596Y on Dec. 15, 2016.
Tolcher A et al: "381 Preliminary results of adose escalation study of the Fibroblast Growth Factor ( FGF) 'trap' FP-1039 (FGFR1:Fc) in patients with advanced malignancies" European Journal of Cancer. Supplement, vol. 8, No. 7, (2010), p. 121.
Zhang H et al "B55: FP-1039 (FGFR1:Fc), a soluble FGFR1 receptor antagonist, inhibits tumor growth and angiogenesis" Molecular Cancer Therapeutics, vol. 6, No. 12, Supp I ., (Dec. 2007), pp. 3449S-3450S.
Zhang H et al, "FP-1039 (FGFR1:Fc). A Soluble FGFR1 Receptor Antagonist, Inhibits Tumor Growth and Angiogenesis", AACR-NCI-EORTC International Conference Molecular Targets and Cancer Therapeutics Discovery, Biology and Clinical Applications, (Oct. 22, 2007), p. 1.

\* cited by examiner

A

B

C

A

B

C

A

B

C

A

B

A

B

C

A

B

C

A

B

A

B

SEQUENCE LISTING

<160> NUMBER OF SEQ ID NOS: 10

<210> SEQ ID NO 1
<211> LENGTH: 374
<212> TYPE: PRT
<213> ORGANISM: Artificial sequence
<220> FEATURE:
<223> OTHER INFORMATION: Synthetic

<400> SEQUENCE: 1

-continued

```
Met Trp Ser Trp Lys Cys Leu Leu Phe Trp Ala Val Leu Val Thr Ala
1               5                   10                  15

Thr Leu Cys Thr Ala Arg Pro Ser Pro Thr Leu Pro Glu Gln Ala Gln
                20                  25                  30

Pro Trp Gly Ala Pro Val Glu Val Glu Ser Phe Leu Val His Pro Gly
            35                  40                  45

Asp Leu Leu Gln Leu Arg Cys Arg Leu Arg Asp Asp Val Gln Ser Ile
    50                  55                  60

Asn Trp Leu Arg Asp Gly Val Gln Leu Ala Glu Ser Asn Arg Thr Arg
65                  70                  75                  80

Ile Thr Gly Glu Glu Val Glu Val Gln Asp Ser Val Pro Ala Asp Ser
                85                  90                  95

Gly Leu Tyr Ala Cys Val Thr Ser Ser Pro Ser Gly Ser Asp Thr Thr
            100                 105                 110

Tyr Phe Ser Val Asn Val Ser Asp Ala Leu Pro Ser Ser Glu Asp Asp
        115                 120                 125

Asp Asp Asp Asp Asp Ser Ser Ser Glu Glu Lys Glu Thr Asp Asn Thr
    130                 135                 140

Lys Pro Asn Pro Val Ala Pro Tyr Trp Thr Ser Pro Glu Lys Met Glu
145                 150                 155                 160

Lys Lys Leu His Ala Val Pro Ala Ala Lys Thr Val Lys Phe Lys Cys
                165                 170                 175

Pro Ser Ser Gly Thr Pro Asn Pro Thr Leu Arg Trp Leu Lys Asn Gly
            180                 185                 190

Lys Glu Phe Lys Pro Asp His Arg Ile Gly Gly Tyr Lys Val Arg Tyr
        195                 200                 205

Ala Thr Trp Ser Ile Ile Met Asp Ser Val Val Pro Ser Asp Lys Gly
    210                 215                 220

Asn Tyr Thr Cys Ile Val Glu Asn Glu Tyr Gly Ser Ile Asn His Thr
225                 230                 235                 240

Tyr Gln Leu Asp Val Val Glu Arg Ser Pro His Arg Pro Ile Leu Gln
                245                 250                 255

Ala Gly Leu Pro Ala Asn Lys Thr Val Ala Leu Gly Ser Asn Val Glu
            260                 265                 270

Phe Met Cys Lys Val Tyr Ser Asp Pro Gln Pro His Ile Gln Trp Leu
        275                 280                 285

Lys His Ile Glu Val Asn Gly Ser Lys Ile Gly Pro Asp Asn Leu Pro
    290                 295                 300

Tyr Val Gln Ile Leu Lys Thr Ala Gly Val Asn Thr Thr Asp Lys Glu
305                 310                 315                 320

Met Glu Val Leu His Leu Arg Asn Val Ser Phe Glu Asp Ala Gly Glu
                325                 330                 335

Tyr Thr Cys Leu Ala Gly Asn Ser Ile Gly Leu Ser His His Ser Ala
            340                 345                 350

Trp Leu Thr Val Leu Glu Ala Leu Glu Glu Arg Pro Ala Val Met Thr
        355                 360                 365

Ser Pro Leu Tyr Leu Glu
    370
```

<210> SEQ ID NO 2
<211> LENGTH: 353
<212> TYPE: PRT
<213> ORGANISM: Artificial sequence
<220> FEATURE:

<223> OTHER INFORMATION: Synthetic

<400> SEQUENCE: 2

```
Arg Pro Ser Pro Thr Leu Pro Glu Gln Ala Gln Pro Trp Gly Ala Pro
  1               5                  10                  15

Val Glu Val Glu Ser Phe Leu Val His Pro Gly Asp Leu Leu Gln Leu
             20                  25                  30

Arg Cys Arg Leu Arg Asp Asp Val Gln Ser Ile Asn Trp Leu Arg Asp
         35                  40                  45

Gly Val Gln Leu Ala Glu Ser Asn Arg Thr Arg Ile Thr Gly Glu Glu
     50                  55                  60

Val Glu Val Gln Asp Ser Val Pro Ala Asp Ser Gly Leu Tyr Ala Cys
 65                  70                  75                  80

Val Thr Ser Ser Pro Ser Gly Ser Asp Thr Thr Tyr Phe Ser Val Asn
             85                  90                  95

Val Ser Asp Ala Leu Pro Ser Ser Glu Asp Asp Asp Asp Asp Asp Asp
            100                 105                 110

Ser Ser Ser Glu Glu Lys Glu Thr Asp Asn Thr Lys Pro Asn Pro Val
        115                 120                 125

Ala Pro Tyr Trp Thr Ser Pro Glu Lys Met Glu Lys Lys Leu His Ala
    130                 135                 140

Val Pro Ala Ala Lys Thr Val Lys Phe Lys Cys Pro Ser Ser Gly Thr
145                 150                 155                 160

Pro Asn Pro Thr Leu Arg Trp Leu Lys Asn Gly Lys Glu Phe Lys Pro
                165                 170                 175

Asp His Arg Ile Gly Gly Tyr Lys Val Arg Tyr Ala Thr Trp Ser Ile
            180                 185                 190

Ile Met Asp Ser Val Val Pro Ser Asp Lys Gly Asn Tyr Thr Cys Ile
        195                 200                 205

Val Glu Asn Glu Tyr Gly Ser Ile Asn His Thr Tyr Gln Leu Asp Val
    210                 215                 220

Val Glu Arg Ser Pro His Arg Pro Ile Leu Gln Ala Gly Leu Pro Ala
225                 230                 235                 240

Asn Lys Thr Val Ala Leu Gly Ser Asn Val Glu Phe Met Cys Lys Val
                245                 250                 255

Tyr Ser Asp Pro Gln Pro His Ile Gln Trp Leu Lys His Ile Glu Val
            260                 265                 270

Asn Gly Ser Lys Ile Gly Pro Asp Asn Leu Pro Tyr Val Gln Ile Leu
        275                 280                 285

Lys Thr Ala Gly Val Asn Thr Thr Asp Lys Glu Met Glu Val Leu His
    290                 295                 300

Leu Arg Asn Val Ser Phe Glu Asp Ala Gly Glu Tyr Thr Cys Leu Ala
305                 310                 315                 320

Gly Asn Ser Ile Gly Leu Ser His His Ser Ala Trp Leu Thr Val Leu
                325                 330                 335

Glu Ala Leu Glu Glu Arg Pro Ala Val Met Thr Ser Pro Leu Tyr Leu
            340                 345                 350

Glu
```

<210> SEQ ID NO 3
<211> LENGTH: 360
<212> TYPE: PRT
<213> ORGANISM: Artificial sequence
<220> FEATURE:
<223> OTHER INFORMATION: Synthetic

<400> SEQUENCE: 3

```
Met Trp Ser Trp Lys Cys Leu Leu Phe Trp Ala Val Leu Val Thr Ala
1               5                   10                  15

Thr Leu Cys Thr Ala Arg Pro Ser Pro Thr Leu Pro Glu Gln Ala Gln
            20                  25                  30

Pro Trp Gly Ala Pro Val Glu Val Glu Ser Phe Leu Val His Pro Gly
        35                  40                  45

Asp Leu Leu Gln Leu Arg Cys Arg Leu Arg Asp Val Gln Ser Ile
    50                  55                  60

Asn Trp Leu Arg Asp Gly Val Gln Leu Ala Glu Ser Asn Arg Thr Arg
65                  70                  75                  80

Ile Thr Gly Glu Glu Val Glu Val Gln Asp Ser Val Pro Ala Asp Ser
                85                  90                  95

Gly Leu Tyr Ala Cys Val Thr Ser Ser Pro Ser Gly Ser Asp Thr Thr
            100                 105                 110

Tyr Phe Ser Val Asn Val Ser Asp Ala Leu Pro Ser Ser Glu Asp Asp
        115                 120                 125

Asp Asp Asp Asp Asp Ser Ser Ser Glu Glu Lys Glu Thr Asp Asn Thr
130                 135                 140

Lys Pro Asn Pro Val Ala Pro Tyr Trp Thr Ser Pro Glu Lys Met Glu
145                 150                 155                 160

Lys Lys Leu His Ala Val Pro Ala Ala Lys Thr Val Lys Phe Lys Cys
            165                 170                 175

Pro Ser Ser Gly Thr Pro Asn Pro Thr Leu Arg Trp Leu Lys Asn Gly
        180                 185                 190

Lys Glu Phe Lys Pro Asp His Arg Ile Gly Gly Tyr Lys Val Arg Tyr
    195                 200                 205

Ala Thr Trp Ser Ile Ile Met Asp Ser Val Val Pro Ser Asp Lys Gly
210                 215                 220

Asn Tyr Thr Cys Ile Val Glu Asn Glu Tyr Gly Ser Ile Asn His Thr
225                 230                 235                 240

Tyr Gln Leu Asp Val Val Glu Arg Ser Pro His Arg Pro Ile Leu Gln
                245                 250                 255

Ala Gly Leu Pro Ala Asn Lys Thr Val Ala Leu Gly Ser Asn Val Glu
            260                 265                 270

Phe Met Cys Lys Val Tyr Ser Asp Pro Gln Pro His Ile Gln Trp Leu
        275                 280                 285

Lys His Ile Glu Val Asn Gly Ser Lys Ile Gly Pro Asp Asn Leu Pro
    290                 295                 300

Tyr Val Gln Ile Leu Lys Thr Ala Gly Val Asn Thr Thr Asp Lys Glu
305                 310                 315                 320

Met Glu Val Leu His Leu Arg Asn Val Ser Phe Glu Asp Ala Gly Glu
                325                 330                 335

Tyr Thr Cys Leu Ala Gly Asn Ser Ile Gly Leu Ser His His Ser Ala
            340                 345                 350

Trp Leu Thr Val Leu Glu Ala Leu
        355                 360
```

<210> SEQ ID NO 4
<211> LENGTH: 339
<212> TYPE: PRT
<213> ORGANISM: Artificial sequence
<220> FEATURE:
<223> OTHER INFORMATION: Synthetic

<400> SEQUENCE: 4

```
Arg Pro Ser Pro Thr Leu Pro Glu Gln Ala Gln Pro Trp Gly Ala Pro
1               5                   10                  15
Val Glu Val Glu Ser Phe Leu Val His Pro Gly Asp Leu Leu Gln Leu
            20                  25                  30
Arg Cys Arg Leu Arg Asp Asp Val Gln Ser Ile Asn Trp Leu Arg Asp
        35                  40                  45
Gly Val Gln Leu Ala Glu Ser Asn Arg Thr Arg Ile Thr Gly Glu Glu
    50                  55                  60
Val Glu Val Gln Asp Ser Val Pro Ala Asp Ser Gly Leu Tyr Ala Cys
65                  70                  75                  80
Val Thr Ser Ser Pro Ser Gly Ser Asp Thr Thr Tyr Phe Ser Val Asn
                85                  90                  95
Val Ser Asp Ala Leu Pro Ser Ser Glu Asp Asp Asp Asp Asp Asp Asp
            100                 105                 110
Ser Ser Ser Glu Glu Lys Glu Thr Asp Asn Thr Lys Pro Asn Pro Val
        115                 120                 125
Ala Pro Tyr Trp Thr Ser Pro Glu Lys Met Glu Lys Lys Leu His Ala
    130                 135                 140
Val Pro Ala Ala Lys Thr Val Lys Phe Lys Cys Pro Ser Ser Gly Thr
145                 150                 155                 160
Pro Asn Pro Thr Leu Arg Trp Leu Lys Asn Gly Lys Glu Phe Lys Pro
                165                 170                 175
Asp His Arg Ile Gly Gly Tyr Lys Val Arg Tyr Ala Thr Trp Ser Ile
            180                 185                 190
Ile Met Asp Ser Val Val Pro Ser Asp Lys Gly Asn Tyr Thr Cys Ile
        195                 200                 205
Val Glu Asn Glu Tyr Gly Ser Ile Asn His Thr Tyr Gln Leu Asp Val
    210                 215                 220
Val Glu Arg Ser Pro His Arg Pro Ile Leu Gln Ala Gly Leu Pro Ala
225                 230                 235                 240
Asn Lys Thr Val Ala Leu Gly Ser Asn Val Glu Phe Met Cys Lys Val
                245                 250                 255
Tyr Ser Asp Pro Gln Pro His Ile Gln Trp Leu Lys His Ile Glu Val
            260                 265                 270
Asn Gly Ser Lys Ile Gly Pro Asp Asn Leu Pro Tyr Val Gln Ile Leu
        275                 280                 285
Lys Thr Ala Gly Val Asn Thr Thr Asp Lys Glu Met Glu Val Leu His
    290                 295                 300
Leu Arg Asn Val Ser Phe Glu Asp Ala Gly Glu Tyr Thr Cys Leu Ala
305                 310                 315                 320
Gly Asn Ser Ile Gly Leu Ser His His Ser Ala Trp Leu Thr Val Leu
                325                 330                 335
Glu Ala Leu
```

<210> SEQ ID NO 5
<211> LENGTH: 592
<212> TYPE: PRT
<213> ORGANISM: Artificial sequence
<220> FEATURE:
<223> OTHER INFORMATION: Synthetic

<400> SEQUENCE: 5

Met Trp Ser Trp Lys Cys Leu Leu Phe Trp Ala Val Leu Val Thr Ala

-continued

```
    1               5                  10                  15
Thr Leu Cys Thr Ala Arg Pro Ser Pro Thr Leu Pro Glu Gln Ala Gln
                20                  25                  30

Pro Trp Gly Ala Pro Val Glu Val Glu Ser Phe Leu Val His Pro Gly
                35                  40                  45

Asp Leu Leu Gln Leu Arg Cys Arg Leu Arg Asp Val Gln Ser Ile
 50                  55                  60

Asn Trp Leu Arg Asp Gly Val Gln Leu Ala Glu Ser Asn Arg Thr Arg
 65                  70                  75                  80

Ile Thr Gly Glu Glu Val Glu Val Gln Asp Ser Val Pro Ala Asp Ser
                85                  90                  95

Gly Leu Tyr Ala Cys Val Thr Ser Ser Pro Ser Gly Ser Asp Thr Thr
                100                 105                 110

Tyr Phe Ser Val Asn Val Ser Asp Ala Leu Pro Ser Ser Glu Asp Asp
                115                 120                 125

Asp Asp Asp Asp Asp Ser Ser Ser Glu Glu Lys Glu Thr Asp Asn Thr
130                 135                 140

Lys Pro Asn Pro Val Ala Pro Tyr Trp Thr Ser Pro Glu Lys Met Glu
145                 150                 155                 160

Lys Lys Leu His Ala Val Pro Ala Ala Lys Thr Val Lys Phe Lys Cys
                165                 170                 175

Pro Ser Ser Gly Thr Pro Asn Pro Thr Leu Arg Trp Leu Lys Asn Gly
                180                 185                 190

Lys Glu Phe Lys Pro Asp His Arg Ile Gly Gly Tyr Lys Val Arg Tyr
                195                 200                 205

Ala Thr Trp Ser Ile Ile Met Asp Ser Val Val Pro Ser Asp Lys Gly
                210                 215                 220

Asn Tyr Thr Cys Ile Val Glu Asn Glu Tyr Gly Ser Ile Asn His Thr
225                 230                 235                 240

Tyr Gln Leu Asp Val Val Glu Arg Ser Pro His Arg Pro Ile Leu Gln
                245                 250                 255

Ala Gly Leu Pro Ala Asn Lys Thr Val Ala Leu Gly Ser Asn Val Glu
                260                 265                 270

Phe Met Cys Lys Val Tyr Ser Asp Pro Gln Pro His Ile Gln Trp Leu
                275                 280                 285

Lys His Ile Glu Val Asn Gly Ser Lys Ile Gly Pro Asp Asn Leu Pro
                290                 295                 300

Tyr Val Gln Ile Leu Lys Thr Ala Gly Val Asn Thr Thr Asp Lys Glu
305                 310                 315                 320

Met Glu Val Leu His Leu Arg Asn Val Ser Phe Glu Asp Ala Gly Glu
                325                 330                 335

Tyr Thr Cys Leu Ala Gly Asn Ser Ile Gly Leu Ser His His Ser Ala
                340                 345                 350

Trp Leu Thr Val Leu Glu Ala Leu Glu Pro Lys Ser Ser Asp Lys Thr
                355                 360                 365

His Thr Cys Pro Pro Cys Pro Ala Pro Glu Leu Leu Gly Gly Pro Ser
                370                 375                 380

Val Phe Leu Phe Pro Pro Lys Pro Lys Asp Thr Leu Met Ile Ser Arg
385                 390                 395                 400

Thr Pro Glu Val Thr Cys Val Val Val Asp Val Ser His Glu Asp Pro
                405                 410                 415

Glu Val Lys Phe Asn Trp Tyr Val Asp Gly Val Glu Val His Asn Ala
                420                 425                 430
```

```
Lys Thr Lys Pro Arg Glu Glu Gln Tyr Asn Ser Thr Tyr Arg Val Val
            435                 440                 445

Ser Val Leu Thr Val Leu His Gln Asp Trp Leu Asn Gly Lys Glu Tyr
        450                 455                 460

Lys Cys Lys Val Ser Asn Lys Ala Leu Pro Ala Pro Ile Glu Lys Thr
465                 470                 475                 480

Ile Ser Lys Ala Lys Gly Gln Pro Arg Glu Pro Gln Val Tyr Thr Leu
                485                 490                 495

Pro Pro Ser Arg Asp Glu Leu Thr Lys Asn Gln Val Ser Leu Thr Cys
            500                 505                 510

Leu Val Lys Gly Phe Tyr Pro Ser Asp Ile Ala Val Glu Trp Glu Ser
        515                 520                 525

Asn Gly Gln Pro Glu Asn Asn Tyr Lys Thr Thr Pro Pro Val Leu Asp
530                 535                 540

Ser Asp Gly Ser Phe Phe Leu Tyr Ser Lys Leu Thr Val Asp Lys Ser
545                 550                 555                 560

Arg Trp Gln Gln Gly Asn Val Phe Ser Cys Ser Val Met His Glu Ala
                565                 570                 575

Leu His Asn His Tyr Thr Gln Lys Ser Leu Ser Leu Ser Pro Gly Lys
            580                 585                 590

<210> SEQ ID NO 6
<211> LENGTH: 571
<212> TYPE: PRT
<213> ORGANISM: Artificial sequence
<220> FEATURE:
<223> OTHER INFORMATION: Synthetic

<400> SEQUENCE: 6

Arg Pro Ser Pro Thr Leu Pro Glu Gln Ala Gln Pro Trp Gly Ala Pro
1               5                   10                  15

Val Glu Val Glu Ser Phe Leu Val His Pro Gly Asp Leu Leu Gln Leu
            20                  25                  30

Arg Cys Arg Leu Arg Asp Asp Val Gln Ser Ile Asn Trp Leu Arg Asp
        35                  40                  45

Gly Val Gln Leu Ala Glu Ser Asn Arg Thr Arg Ile Thr Gly Glu Glu
    50                  55                  60

Val Glu Val Gln Asp Ser Val Pro Ala Asp Ser Gly Leu Tyr Ala Cys
65                  70                  75                  80

Val Thr Ser Ser Pro Ser Gly Ser Asp Thr Thr Tyr Phe Ser Val Asn
                85                  90                  95

Val Ser Asp Ala Leu Pro Ser Ser Glu Asp Asp Asp Asp Asp Asp Asp
            100                 105                 110

Ser Ser Ser Glu Glu Lys Glu Thr Asp Asn Thr Lys Pro Asn Pro Val
        115                 120                 125

Ala Pro Tyr Trp Thr Ser Pro Glu Lys Met Glu Lys Lys Leu His Ala
    130                 135                 140

Val Pro Ala Ala Lys Thr Val Lys Phe Lys Cys Pro Ser Ser Gly Thr
145                 150                 155                 160

Pro Asn Pro Thr Leu Arg Trp Leu Lys Asn Gly Lys Glu Phe Lys Pro
                165                 170                 175

Asp His Arg Ile Gly Gly Tyr Lys Val Arg Tyr Ala Thr Trp Ser Ile
            180                 185                 190

Ile Met Asp Ser Val Val Pro Ser Asp Lys Gly Asn Tyr Thr Cys Ile
        195                 200                 205
```

Val Glu Asn Glu Tyr Gly Ser Ile Asn His Thr Tyr Gln Leu Asp Val
    210                 215                 220

Val Glu Arg Ser Pro His Arg Pro Ile Leu Gln Ala Gly Leu Pro Ala
225                 230                 235                 240

Asn Lys Thr Val Ala Leu Gly Ser Asn Val Glu Phe Met Cys Lys Val
                245                 250                 255

Tyr Ser Asp Pro Gln Pro His Ile Gln Trp Leu Lys His Ile Glu Val
                260                 265                 270

Asn Gly Ser Lys Ile Gly Pro Asp Asn Leu Pro Tyr Val Gln Ile Leu
            275                 280                 285

Lys Thr Ala Gly Val Asn Thr Thr Asp Lys Glu Met Glu Val Leu His
    290                 295                 300

Leu Arg Asn Val Ser Phe Glu Asp Ala Gly Glu Tyr Thr Cys Leu Ala
305                 310                 315                 320

Gly Asn Ser Ile Gly Leu Ser His His Ser Ala Trp Leu Thr Val Leu
                325                 330                 335

Glu Ala Leu Glu Pro Lys Ser Ser Asp Lys Thr His Thr Cys Pro Pro
                340                 345                 350

Cys Pro Ala Pro Glu Leu Leu Gly Gly Pro Ser Val Phe Leu Phe Pro
            355                 360                 365

Pro Lys Pro Lys Asp Thr Leu Met Ile Ser Arg Thr Pro Glu Val Thr
    370                 375                 380

Cys Val Val Val Asp Val Ser His Glu Asp Pro Glu Val Lys Phe Asn
385                 390                 395                 400

Trp Tyr Val Asp Gly Val Glu Val His Asn Ala Lys Thr Lys Pro Arg
                405                 410                 415

Glu Glu Gln Tyr Asn Ser Thr Tyr Arg Val Val Ser Val Leu Thr Val
                420                 425                 430

Leu His Gln Asp Trp Leu Asn Gly Lys Glu Tyr Lys Cys Lys Val Ser
    435                 440                 445

Asn Lys Ala Leu Pro Ala Pro Ile Glu Lys Thr Ile Ser Lys Ala Lys
450                 455                 460

Gly Gln Pro Arg Glu Pro Gln Val Tyr Thr Leu Pro Pro Ser Arg Asp
465                 470                 475                 480

Glu Leu Thr Lys Asn Gln Val Ser Leu Thr Cys Leu Val Lys Gly Phe
                485                 490                 495

Tyr Pro Ser Asp Ile Ala Val Glu Trp Glu Ser Asn Gly Gln Pro Glu
            500                 505                 510

Asn Asn Tyr Lys Thr Thr Pro Pro Val Leu Asp Ser Asp Gly Ser Phe
    515                 520                 525

Phe Leu Tyr Ser Lys Leu Thr Val Asp Lys Ser Arg Trp Gln Gln Gly
530                 535                 540

Asn Val Phe Ser Cys Ser Val Met His Glu Ala Leu His Asn His Tyr
545                 550                 555                 560

Thr Gln Lys Ser Leu Ser Leu Ser Pro Gly Lys
                565                 570

<210> SEQ ID NO 7
<211> LENGTH: 21
<212> TYPE: PRT
<213> ORGANISM: Artificial sequence
<220> FEATURE:
<223> OTHER INFORMATION: Synthetic

<400> SEQUENCE: 7

Met Trp Ser Trp Lys Cys Leu Leu Phe Trp Ala Val Leu Val Thr Ala
1               5                   10                  15

Thr Leu Cys Thr Ala
            20

<210> SEQ ID NO 8
<211> LENGTH: 232
<212> TYPE: PRT
<213> ORGANISM: Artificial sequence
<220> FEATURE:
<223> OTHER INFORMATION: Synthetic

<400> SEQUENCE: 8

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
                20                  25                  30

Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 9
<211> LENGTH: 228
<212> TYPE: PRT
<213> ORGANISM: Artificial sequence
<220> FEATURE:
<223> OTHER INFORMATION: Synthetic

<400> SEQUENCE: 9

Glu Arg Lys Cys Cys Val Glu Cys Pro Pro Cys Pro Ala Pro Pro Val
1               5                   10                  15

Ala Gly Pro Ser Val Phe Leu Phe Pro Pro Lys Pro Lys Asp Thr Leu
                20                  25                  30

Met Ile Ser Arg Thr Pro Glu Val Thr Cys Val Val Val Asp Val Ser

His Glu Asp Pro Glu Val Gln Phe Asn Trp Tyr Val Asp Gly Val Glu
            50                  55                  60

Val His Asn Ala Lys Thr Lys Pro Arg Glu Glu Gln Phe Asn Ser Thr
 65                  70                  75                  80

Phe Arg Val Val Ser Val Leu Thr Val His Gln Asp Trp Leu Asn
                85                  90                  95

Gly Lys Glu Tyr Lys Cys Lys Val Ser Asn Lys Gly Leu Pro Ala Pro
                100                 105                 110

Ile Glu Lys Thr Ile Ser Lys Thr Lys Gly Gln Pro Arg Glu Pro Gln
                115                 120                 125

Val Tyr Thr Leu Pro Pro Ser Arg Glu Glu Met Thr Lys Asn Gln Val
130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Met Leu Asp Ser Asp Gly Ser Phe Phe Leu Tyr Ser Lys Leu Thr
                180                 185                 190

Val Asp Lys Ser Arg Trp Gln Gln Gly Asn Val Phe Ser Cys Ser Val
                195                 200                 205

Met His Glu Ala Leu His Asn His Tyr Thr Gln Lys Ser Leu Ser Leu
210                 215                 220

Ser Pro Gly Lys
225

<210> SEQ ID NO 10
<211> LENGTH: 229
<212> TYPE: PRT
<213> ORGANISM: Artificial sequence
<220> FEATURE:
<223> OTHER INFORMATION: Synthetic

<400> SEQUENCE: 10

Glu Ser Lys Tyr Gly Pro Pro Cys Pro Ser Cys Pro Ala Pro Glu Phe
1               5                   10                  15

Leu Gly Gly Pro Ser Val Phe Leu Phe Pro Pro Lys Pro Lys Asp Thr
                20                  25                  30

Leu Met Ile Ser Arg Thr Pro Glu Val Thr Cys Val Val Val Asp Val
            35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
                100                 105                 110

Ser Ile Glu Lys Thr Ile Ser Lys Ala Lys Gly Gln Pro Arg Glu Pro
            115                 120                 125

Gln Val Tyr Thr Leu Pro Pro Ser Gln Glu Glu Met Thr Lys Asn Gln
        130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr

-continued

```
                165                 170                 175
Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225
```

METHODS OF TREATING MESOTHELIOMA BY ADMINISTRATION OF COMPOUNDS COMPRISING FGFR1 ECD

BACKGROUND

Soluble forms of Fibroblast Growth Factor Receptor 1 (FGFR1) have been shown to inhibit tumor cell growth in vitro and in vivo. See, e.g., U.S. Pat. No. 7,678,890. The efficacy of anti-cancer therapies is, in some instances, dependent on the genetic makeup of the cancer being targeted.

SUMMARY

In some embodiments, methods of treating cancer having a higher level of FGF2 compared to the level of VEGF in a subject are provided. In some embodiments, a higher level of FGF2 compared to the level of VEGF is indicative of therapeutic responsiveness by the cancer to a fibroblast growth factor receptor 1 (FGFR1) extracellular domain (ECD) or an FGFR1 ECD fusion molecule. In some embodiments, the method comprises administering a therapeutically effective amount of an FGFR1 ECD or an FGFR1 ECD fusion molecule to the subject. In another embodiment is provided a FGFR1 ECD or FGFR1 ECD fusion molecule for use in a method of treating cancer, characterised in that said cancer has a higher level of FGF2 compared to the level of VEGF in a subject. In a further embodiment is provided the use of an FGFR1 ECD or FDFR1 ECD fusion molecule in the manufacture of a medicament for use in a method of treating cancer, characterised in that said cancer has a higher level of FGF 2 compared to the level of VEGF in a subject. In some embodiments, a method comprises administering a therapeutically effective amount of an FGFR1 ECD or an FGFR1 ECD fusion molecule and a therapeutically effective amount of at least one anti-angiogenic agent to the subject. In some embodiments, the anti-angiogenic agent is a VEGF antagonist. In some embodiments, the VEGF antagonist is selected from pazopanib, bevacizumab, axitinib, aflibercept, sorafenib, or sunitinib.

In some embodiments, methods of treating cancer in a subject are provided, comprising administering a therapeutically effective amount of a fibroblast growth factor receptor 1 (FGFR1) extracellular domain (ECD) or an FGFR1 ECD fusion molecule to the subject. In some embodiments, a method comprises administering a therapeutically effective amount of an FGFR1 ECD or an FGFR1 ECD fusion molecule and a therapeutically effective amount of at least one anti-angiogenic agent to the subject. In some embodiments, prior to administration of the FGFR1 ECD or FGFR1 ECD fusion molecule, at least a portion of the cells of the cancer have been determined to have a higher level of FGF2 compared to the level of VEGF. In some embodiments, at least 10%, at least 20%, at least 30%, at least 40%, at least 50%, at least 60%, at least 70%, at least 80%, or at least 90% of the cells of a cancer sample have been determined to have a higher level of FGF2 compared to the level of VEGF. In some embodiments, a higher level of FGF2 compared to the level of VEGF in a cancer is indicative of therapeutic responsiveness by the cancer to an FGFR1 ECD or FGFR1 ECD fusion molecule.

In some embodiments, methods of identifying a subject who may benefit from treatment with a fibroblast growth factor receptor 1 (FGFR1) extracellular domain (ECD) or an FGFR1 ECD fusion molecule are provided. In some embodiments, the method comprises determining the levels of FGF2 and VEGF in a sample obtained from the subject, wherein a higher level of FGF2 compared to the level of VEGF in the sample indicates that the subject may benefit from treatment with the fibroblast growth factor receptor 1 (FGFR1) extracellular domain (ECD) or an FGFR1 ECD fusion molecule.

In some embodiments, methods of predicting responsiveness of a subject with cancer to a fibroblast growth factor receptor 1 (FGFR1) extracellular domain (ECD) or an FGFR1 ECD fusion molecule are provided. In some embodiments, the method comprises determining the levels of FGF2 and VEGF in a sample obtained from the subject, wherein a higher level of FGF2 compared to the level of VEGF in the sample indicates that the cancer is predicted to respond to the fibroblast growth factor receptor 1 (FGFR1) extracellular domain (ECD) or an FGFR1 ECD fusion molecule.

In some embodiments, the FGF2 level is FGF2 mRNA level. In some embodiments, the VEGF level is VEGF mRNA level. In some embodiments, the mRNA level is determined by quantitative RT-PCR. In some embodiments, the mRNA level is determined by a method selected from quantitative RT-PCR, microarray, digital PCT, RNA-Seq, RNase Protection Assay (RPA), Northern blot, and in situ hybridization (ISH).

In some embodiments, the FGF2 level is FGF2 protein level. In some embodiments, the VEGF level is VEGF protein level. In some embodiments, the protein level is determined by immunohistochemistry. In some embodiments, the protein level is determined by a method selected from immunohistochemistry, ELISA, mass spectrometry, reverse phase protein array (RPPA), antibody array, nano-immuno assay, Western blot, and capillary protein analysis assay.

In some embodiments, the ratio of FGF2 level to VEGF level is greater than 1. In some embodiments, the ratio of FGF2 level to VEGF level is greater than 1.1. In some embodiments, the ratio of FGF2 level to VEGF level is greater than 1.2. In some embodiments, the ratio of FGF2 level to VEGF level is greater than 1.3. In some embodiments, the ratio of FGF2 level to VEGF level is greater than 1.4. In some embodiments, the ratio of FGF2 level to VEGF level is greater than 1.5.

In some embodiments, the cancer is responsive to a FGFR1 ECD or a FGFR1 ECD fusion molecule as a monotherapy. In some embodiments, the subject is administered a FGFR1 ECD or a FGFR1 ECD fusion molecule as a monotherapy.

In some embodiments, the cancer is selected from kidney cancer (such as renal cell carcinoma), liver cancer (such as hepatocellular carcinoma), lung cancer, colon cancer, liver cancer, breast cancer, stomach cancer, ovarian cancer, endometrial cancer, esophageal cancer, head and neck cancer, glioblastoma, mesothelioma, and prostate cancer. In some embodiments, the cancer is gastrointestinal stromal tumor.

In some embodiments, methods of treating cancer having a lower level of FGF2 compared to the level of VEGF in a subject are provided. In some embodiments, the method comprises administering to a subject with the cancer an FGFR1 ECD or FGFR1 ECD fusion molecule and at least one anti-angiogenic agent. In some embodiments, a method comprises administering a therapeutically effective amount of an FGFR1 ECD or an FGFR1 ECD fusion molecule and a therapeutically effective amount of at least one anti-angiogenic agent to the subject. In some embodiments, the anti-angiogenic agent is a VEGF antagonist. In some embodiments, the VEGF antagonist is selected from pazopanib, bevacizumab, axitinib, aflibercept, sorafenib, or sunitinib.

In some embodiments, methods of treating cancer in a subject are provided, comprising administering a therapeutically effective amount of a fibroblast growth factor receptor 1 (FGFR1) extracellular domain (ECD) or an FGFR1 ECD fusion molecule and a therapeutically effective amount of at least one anti-angiogenic agent to the subject. In some embodiments, prior to administration of the FGFR1 ECD or FGFR1 ECD fusion molecule and at least one anti-angiogenic agent, at least a portion of the cells of the cancer have been determined to have a lower level of FGF2 compared to the level of VEGF. In some embodiments, at least 10%, at least 20%, at least 30%, at least 40%, at least 50%, at least 60%, at least 70%, at least 80%, or at least 90% of the cells of a cancer sample have been determined to have a lower level of FGF2 compared to the level of VEGF. In some embodiments, methods of treating a cancer with a lower level of FGF2 compared to the level of VEGF are provided, comprising administering to a subject with the cancer an FGFR1 ECD or FGFR1 ECD fusion molecule and at least one anti-angiogenic agent.

In some embodiments, methods of identifying a subject who may benefit from treatment with a fibroblast growth factor receptor 1 (FGFR1) extracellular domain (ECD) or an FGFR1 ECD fusion molecule and at least one anti-angiogenic agent are provided. In some embodiments, the method comprises determining the levels of FGF2 and VEGF in a sample obtained from the subject, wherein the lower level of FGF2 compared to the level of VEGF in the sample indicates that the subject may benefit from treatment with the fibroblast growth factor receptor 1 (FGFR1) extracellular domain (ECD) or an FGFR1 ECD fusion molecule and at least one anti-angiogenic agent.

In some embodiments, methods of predicting responsiveness of a subject with cancer to a fibroblast growth factor receptor 1 (FGFR1) extracellular domain (ECD) or an FGFR1 ECD fusion molecule and at least one anti-angiogenic agent are provided. In some embodiments, the method comprises determining the levels of FGF2 and VEGF in a sample obtained from the subject, wherein a lower level of FGF2 compared to the level of VEGF in the sample indicates that the cancer is predicted to respond to treatment with the fibroblast growth factor receptor 1 (FGFR1) extracellular domain (ECD) or an FGFR1 ECD fusion molecule and at least one anti-angiogenic agent.

In some embodiments, the FGF2 level is FGF2 mRNA level. In some embodiments, the VEGF level is VEGF mRNA level. In some embodiments, the mRNA level is determined by quantitative RT-PCR. In some embodiments, the mRNA level is determined by a method selected from quantitative RT-PCR, microarray, digital PCT, RNA-Seq, RNase Protection Assay (RPA), Northern blot, and in situ hybridization (ISH).

In some embodiments, the FGF2 level is FGF2 protein level. In some embodiments, the VEGF level is VEGF protein level. In some embodiments, the protein level is determined by immunohistochemistry. In some embodiments, the protein level is determined by a method selected from immunohistochemistry, ELISA, mass spectrometry, reverse phase protein array (RPPA), antibody array, nano-immuno assay, Western blot, and capillary protein analysis assay.

In some embodiments, the ratio of FGF2 level to VEGF level is less than 1. In some embodiments, the ratio of FGF2 level to VEGF level is less than 0.9. In some embodiments, the ratio of FGF2 level to VEGF level is less than 0.8. In some embodiments, the ratio of FGF2 level to VEGF level is less than 0.7. In some embodiments, the ratio of FGF2 level to VEGF level is less than 0.6.

In some embodiments, the cancer is selected from kidney cancer (such as renal cell carcinoma), liver cancer (such as hepatocellular carcinoma), lung cancer, colon cancer, liver cancer, breast cancer, stomach cancer, ovarian cancer, endometrial cancer, esophageal cancer, head and neck cancer, glioblastoma, mesothelioma, and prostate cancer. In some embodiments, the cancer is gastrointestinal stromal tumor. In some embodiments, the cancer is selected from kidney cancer (such as renal cell carcinoma), liver cancer (such as hepatocellular carcinoma), and mesothelioma. In some embodiments, the cancer is renal cell carcinoma. In some embodiments, the cancer is hepatocellular carcinoma. In some embodiments, the cancer is mesothelioma.

In some embodiments, methods of treating renal cell carcinoma (RCC) are provided. In some embodiments, the method comprises administering to a subject with RCC a fibroblast growth factor receptor 1 (FGFR1) extracellular domain (ECD) or an FGFR1 ECD fusion molecule and a VEGF antagonist. In some embodiments, the method comprises administering to a subject with RCC an FGFR1 ECD or FGFR1 ECD fusion molecule and a VEGF antagonist selected from axitinib, pazopanib, and sorafenib.

In some embodiments, methods of treating cancer are provided, comprising administering to a subject with cancer an FGFR1 ECD or FGFR1 ECD fusion molecule wherein the subject has previously been treated with at least one therapeutic agent selected from pazopanib, bevacizumab, axitinib, aflibercept, sorafenib, and sunitinib. In some embodiments, the subject has previously been treated with pazopanib. In some embodiments, the subject's cancer has become pazopanib-resistant during or following pazopanib treatment. In some embodiments, methods of treating pazopanib-resistant cancer are provided, comprising administering to a subject with pazopanib-resistant cancer an FGFR1 ECD or FGFR1 ECD fusion molecule. In some embodiments, the method comprises administering pazopanib and an FGFR1 ECD or FGFR1 ECD fusion molecule.

In some embodiments, methods of treating cancer are provided, comprising administering to a subject with cancer an FGFR1 ECD or FGFR1 ECD fusion molecule and axitinib, wherein the subject has previously been treated with at least one therapeutic agent selected from pazopanib, bevacizumab, axitinib, aflibercept, sorafenib, and sunitinib. In some such embodiments, at least one therapeutic agent is selected from pazopanib, axitinib, and sorafenib. In some such embodiments, at least one therapeutic agent is pazopanib. In some embodiments, the cancer is selected from kidney cancer (such as renal cell carcinoma), liver cancer (such as hepatocellular carcinoma), glioblastoma, and mesothelioma.

In some embodiments, methods of treating VEGF-resistant cancers are provided. In some embodiments, methods comprise administering to a subject with a VEGF-resistant cancer an FGFR1 ECD or FGFR1 ECD fusion molecule. In some embodiments, a VEGF-resistant cancer is a cancer with high FGF2 expression and/or with an FGF2/VEGF ratio of greater than 1. In some embodiments, the VEGF-resistant cancer is selected from kidney cancer (such as renal cell carcinoma), liver cancer (such as hepatocellular carcinoma), glioblastoma, and mesothelioma.

In some embodiments, methods of reducing blood vessel density in a solid cancer are provided. In some embodiments, methods of reducing blood vessel density in a solid cancer are provided, wherein the cancer has a higher level of FGF2 compared to the level of VEGF. In some embodiments, methods of reducing blood vessel density in a VEGF-resistant solid cancer are provided. In some embodiments, a method of reducing blood vessel density in a solid cancer comprises administering to a subject with cancer an FGFR1 ECD or FGFR1 ECD fusion molecule. In some embodiments, blood vessel density is measured in the whole tumor sample. In some embodiments, the cancer is selected from kidney cancer (such as renal cell carcinoma), liver cancer (such as hepatocellular carcinoma), lung cancer, colon cancer, liver cancer, breast cancer, stomach cancer, ovarian cancer, endometrial cancer, esophageal cancer, head and neck cancer, glioblastoma, mesothelioma, and prostate cancer. In some embodiments, the cancer is selected from kidney cancer (such as renal cell carcinoma), liver cancer (such as hepatocellular carcinoma), glioblastoma, and mesothelioma. In some embodiments, the cancer is renal cell carcinoma. In some embodiments, the cancer is hepatocellular carcinoma. In some embodiments, the cancer is mesothelioma.

In some embodiments, methods of treating mesothelioma are provided, comprising administering to a subject with mesothelioma an FGFR1 ECD or FGFR1 ECD fusion molecule and at least one therapeutic agent selected from paclitaxel, carboplatin, docetaxel, pemetrexed, and cisplatin. In some embodiments, the method comprises administering an FGFR1 ECD or FGFR1 ECD fusion molecule, paclitaxel and carboplatin. In some embodiments, the method comprises administering an FGFR1 ECD or FGFR1 ECD fusion molecule and docetaxel. In some embodiments, the method comprises administering an FGFR1 ECD or FGFR1 ECD fusion molecule, pemetrexed, and cisplatin. In some embodiments, administration of the FGFR1 ECD or FGFR1 ECD fusion molecule and at least one therapeutic agent reduces blood vessel density in the mesothelioma. In some embodiments, the mesothelioma has a high level of FGF2. In some embodiments, the mesothelioma has a higher level of FGF2 compared to the level of VEGF. In some embodiments, the ratio of FGF2 level to VEGF level is greater than 1.

In any of the methods described herein, the method may comprise administering an FGFR1 ECD. In some embodiments, the FGFR1 ECD comprises an amino acid sequence selected from SEQ ID NOs: 1 to 4.

In any of the methods described herein, the method may comprise administering an FGFR1 ECD fusion molecule. In some embodiments, the FGFR1 ECD fusion molecule comprises an FGFR1 ECD and a fusion partner, and wherein the fusion partner is Fc. In some embodiments, the FGFR1 ECD fusion molecule comprises a sequence selected from SEQ ID NO: 5 and SEQ ID NO: 6.

In one embodiment the present invention provides the use of a therapeutically effective amount of an FGFR1 ECD or an FGFR1 ECD fusion molecule for the treatment of cancer in a subject wherein said cancer has a higher level of FGF2 compared to the level of VEGF wherein a higher level of FGF2 compared to the level of VEGF is indicative of therapeutic responsiveness by the cancer to a fibroblast growth factor receptor 1 (FGFR1) extracellular domain (ECD) or an FGFR1 ECD fusion molecule.

In another embodiment, the present invention provides the use of a therapeutically effective amount of a fibroblast growth factor receptor 1 (FGFR1) extracellular domain (ECD) or an FGFR1 ECD fusion molecule for the treatment of cancer in a subject, wherein, prior to administration of the FGFR1 ECD or FGFR1 ECD fusion molecule, at least a portion of the cells of the cancer have been determined to have a higher level of FGF2 compared to the level of VEGF, and wherein a higher level of FGF2 compared to the level of VEGF in a cancer is indicative of therapeutic responsiveness by the cancer to an FGFR1 ECD or FGFR1 ECD fusion molecule.

In another embodiment, the present invention provides the use of a fibroblast growth factor receptor 1 (FGFR1) extracellular domain (ECD) or an FGFR1 ECD fusion molecule in the manufacture of a medicament for the treatment of cancer in a subject wherein said cancer has a higher level of FGF2 compared to the level of VEGF, wherein a higher level of FGF2 compared to the level of VEGF is indicative of therapeutic responsiveness by the cancer to a fibroblast growth factor receptor 1 (FGFR1) extracellular domain (ECD) or an FGFR1 ECD fusion molecule In another embodiment, the present invention provides the use of a fibroblast growth factor receptor 1 (FGFR1) extracellular domain (ECD) or an FGFR1 ECD fusion molecule in the manufacture of a medicament for the treatment of cancer in a subject wherein, prior to administration of the FGFR1 ECD or FGFR1 ECD fusion molecule, at least a portion of the cells of the cancer have been determined to have a higher level of FGF2 compared to the level of VEGF, and wherein a higher level of FGF2 compared to the level of VEGF in a cancer is indicative of therapeutic responsiveness by the cancer to an FGFR1 ECD or FGFR1 ECD fusion molecule.

In one embodiment the present invention provides the use of a therapeutically effective amount of an FGFR1 ECD or an FGFR1 ECD fusion molecule and a therapeutically effective amount of at least one anti-angiogenic agent for the treatment of cancer in a subject wherein said cancer has a lower level of FGF2 compared to the level of VEGF wherein a lower level of FGF2 compared to the level of VEGF is indicative of therapeutic responsiveness by the cancer to an FGFR1 ECD or FGFR1 ECD fusion molecule and at least one anti-angiogenic agent.

In another embodiment, the present invention provides the use of a therapeutically effective amount of a fibroblast growth factor receptor 1 (FGFR1) extracellular domain (ECD) or an FGFR1 ECD fusion molecule and at least one anti-angiogenic agent for the treatment of cancer in a subject, wherein, prior to administration of the FGFR1 ECD or FGFR1 ECD fusion molecule and at least one anti-angiogenic agent at least a portion of the cells of the cancer have been determined to have a lower level of FGF2 compared to the level of VEGF, and wherein a lower level of FGF2 compared to the level of VEGF in a cancer is indicative of therapeutic responsiveness by the cancer to an FGFR1 ECD or FGFR1 ECD fusion molecule and at least one anti-angiogenic agent.

In another embodiment, the present invention provides the use of a fibroblast growth factor receptor 1 (FGFR1) extracellular domain (ECD) or an FGFR1 ECD fusion molecule and an anti-angiogenic agent in the manufacture of a medicament for the treatment of cancer in a subject wherein said cancer has a lower level of FGF2 compared to the level of VEGF, wherein a lower level of FGF2 compared to the level of VEGF is indicative of therapeutic responsiveness by the cancer to a fibroblast growth factor receptor 1 (FGFR1) extracellular domain (ECD) or an FGFR1 ECD fusion molecule and an anti-angiogenic agent.

In another embodiment, the present invention provides the use of a fibroblast growth factor receptor 1 (FGFR1)

extracellular domain (ECD) or an FGFR1 ECD fusion molecule and an anti-angiogenic agent in the manufacture of a medicament for the treatment of cancer in a subject wherein, prior to administration of the FGFR1 ECD or FGFR1 ECD fusion molecule and an anti-angiogenic agent, at least a portion of the cells of the cancer have been determined to have a lower level of FGF2 compared to the level of VEGF, and wherein a lower level of FGF2 compared to the level of VEGF in a cancer is indicative of therapeutic responsiveness by the cancer to an FGFR1 ECD or FGFR1 ECD fusion molecule and an anti-angiogenic agent.

In one embodiment of the invention is provided an FGFR1 ECD or FGFR1 ECD fusion protein for use in a method of reducing blood vessel density in a solid cancer. In one aspect of this embodiment, said solid cancer has a higher level of FGF2 compared to the level of VEGF.

In one embodiment of the invention is provided the use of an FGFR1 ECD or FGFR1 ECD fusion protein in the manufacture of a medicament for use in a method of reducing blood vessel density in a solid cancer. In one aspect of this embodiment, said solid cancer has a higher level of FGF2 compared to the level of VEGF.

In a further embodiment of the invention is provided an FGFR1 ECD or FGFR1 ECD fusion molecule and at least one therapeutic agent selected from paclitaxel, carboplatin, docetaxel, pemtrexed and cisplatin for use in the treatment of mesothelioma. In one aspect of this embodiment, said treatment involves the use of an FGFR1 ECD or FGFR1 ECD fusion molecule, paclitaxel and carboplatin. In one aspect of this embodiment said treatment involves the use of an FGFR1 ECD or FGFR1 ECD fusion molecule and docetaxel. In one aspect of this embodiment, said treatment involves the use of an FGFR1 ECD or FGFR1 ECD fusion molecule, pemetrexed, and cisplatin. In any of these aspects, administration of the FGFR1 or FGFR1 ECD fusion molecule and at least one therapeutic agent reduces the blood vessel density in said mesothelioma.

In a further embodiment of the invention is provided the use of FGFR1 ECD or FGFR1 ECD fusion molecule and at least one therapeutic agent selected from paclitaxel, carboplatin, docetaxel, pemtrexed and cisplatin in the manufacture of a medicament for use in the treatment of mesothelioma. In one aspect of this embodiment, said medicament comprises an FGFR1 ECD or FGFR1 ECD fusion molecule, paclitaxel and carboplatin. In one aspect of this embodiment said medicament comprises an FGFR1 ECD or FGFR1 ECD fusion molecule and docetaxel. In one aspect of this embodiment, said medicament comprises an FGFR1 ECD or FGFR1 ECD fusion molecule, pemetrexed, and cisplatin. In any of these aspects, administration of said medicament reduces the blood vessel density in said mesothelioma.

In any aspect of these embodiments, the FGF2 level or VEGF level may be mRNA levels. In one feature of this aspect, the mRNA level may be determined by quantitative RT-PCR.

Further, in any aspect of these embodiments, the FGF2 level or VEGF level may be protein levels. In one feature of this aspect, the protein level may be determined by immunohistochemistry.

In any aspect of these embodiments, the anti-angiogenic agent is a VEGF antagonist. In a further feature of this aspect, the VEGF antagonist is selected from pazopanib, bevacizumab, axitinib, aflibercept, sorafenib, or sunitinib.

In any aspect of these embodiments, the cancer is selected from kidney cancer (such as renal cell carcinoma), liver cancer (such as hepatocellular carcinoma), lung cancer, colon cancer, liver cancer, breast cancer, stomach cancer, ovarian cancer, endometrial cancer, esophageal cancer, head and neck cancer, glioblastoma, and prostate cancer.

In any aspect of these embodiments, the composition used in the treatment of cancer or the medicament used in the treatment of cancer comprises an FGFR1 ECD. In one feature of this aspect the FGFR1 ECD comprises an amino acid sequence selected from SEQ ID NOs: 1 to 4.

In any aspect of these embodiments, the composition used in the treatment of cancer or the medicament used in the treatment of cancer comprises an FGFR1 ECD fusion molecule. In one feature of this aspect, the FGFR1 ECD fusion molecule comprises an FGFR1 ECD and a fusion partner, and wherein the fusion partner is Fc. In one further feature of this aspect, the FGFR1 ECD fusion molecule comprises a sequence selected from SEQ ID NO: 5 and SEQ ID NO: 6.

In any aspect of these some embodiments, "at least a portion of the cells" is at least 10%, at least 20%, at least 30%, at least 40%, at least 50%, at least 60%, at least 70%, at least 80%, or at least 90% of the cells of a cancer sample.

In some embodiments, the FGFR1 ECD or FGFR1 ECD fusion molecule is an amount in the range of about 0.5 mg/kg body weight to about 30 mg/kg body weight, such as an amount in the range of about 8 to about 16 mg/kg body weight, calculated using an extinction coefficient of 1.42 mL/mg*cm. See Table 1. In some embodiments, the therapeutically effective amount of the FGFR1 ECD or FGFR1 ECD fusion molecule is a dose of about 8 mg/kg body weight. In some embodiments, the therapeutically effective amount of the FGFR1 ECD or FGFR1 ECD fusion molecule is a dose of about 16 mg/kg body weight. In some embodiments, the therapeutically effective amount of the FGFR1 ECD or FGFR1 ECD fusion molecule is a dose of about 20 mg/kg body weight. In some embodiments, dosages may be administered twice a week, weekly, every other week, at a frequency between weekly and every other week, every three weeks, every four weeks, or every month.

In certain embodiments, the cancer is prostate cancer, breast cancer, colorectal cancer, stomach cancer, lung cancer, brain cancer, ovarian cancer, endometrial cancer, esophageal cancer, head and neck cancer, laryngeal cancer, liver cancer, renal cancer (kidney cancer), glioblastoma, or pancreatic cancer. In certain embodiments, the cancer is breast cancer, esophageal cancer, renal cancer, head and neck cancer, or lung cancer. In certain embodiments, the cancer is lung cancer. In some embodiments, the lung cancer is non-small cell lung cancer. In some embodiments, the lung cancer is small cell lung cancer. In some embodiments, the lung cancer is squamous cell carcinoma. In some embodiments, the cancer is head and neck cancer. In some embodiments, the head and neck cancer is squamous cell carcinoma of the head and neck. In some embodiments, the cancer is selected from kidney cancer (such as renal cell carcinoma), liver cancer (such as hepatocellular carcinoma), and mesothelioma. In some embodiments, the cancer is renal cell carcinoma. In some embodiments, the cancer is hepatocellular carcinoma. In some embodiments, the cancer is mesothelioma.

Any embodiment described herein or any combination thereof applies to any and all methods of the invention described herein.

DETAILED DESCRIPTION

Figure 1:
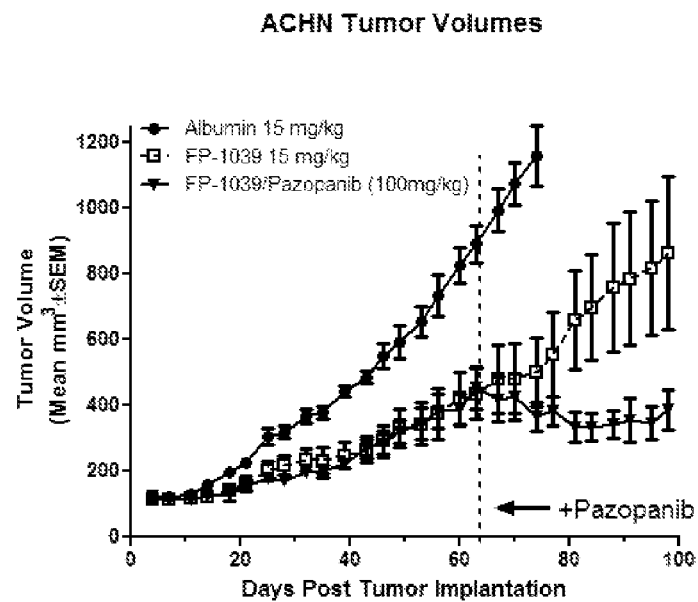
FIG. 1A-C show mean tumor volume at various time points in mice implanted with ACHN cells and treated with FGFR1-ECD.339-Fc ("FP-1039"), FGFR1-ECD.339-Fc ("FP-1039") and pazopanib, or albumin, as described in Example 2.
Figure 1:
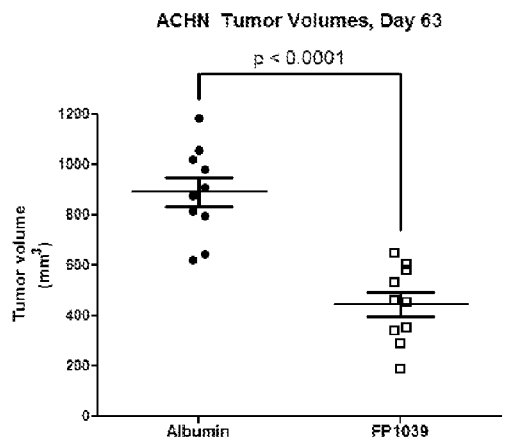
Figure 1:
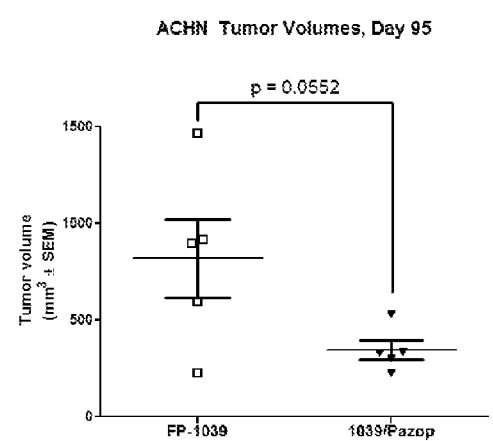

The section headings used herein are for organizational purposes only and are not to be construed as limiting the subject matter described.

Definitions

Unless otherwise defined, scientific and technical terms used in connection with the present invention shall have the meanings that are commonly understood by those of ordinary skill in the art. Further, unless otherwise required by context, singular terms shall include pluralities and plural terms shall include the singular.

Certain techniques used in connection with recombinant DNA, oligonucleotide synthesis, tissue culture and transformation (e.g., electroporation, lipofection), enzymatic reactions, and purification techniques are known in the art. Many such techniques and procedures are described, e.g., in Sambrook et al. *Molecular Cloning: A Laboratory Manual* (2nd ed., Cold Spring Harbor Laboratory Press, Cold Spring Harbor, N.Y. (1989)), among other places. In addition, certain techniques for chemical syntheses, chemical analyses, pharmaceutical preparation, formulation, and delivery, and treatment of patients are also known in the art.

In this application, the use of "or" means "and/or" unless stated otherwise. In the context of a multiple dependent claim, the use of "or" refers back to more than one preceding independent or dependent claim in the alternative only. Also, terms such as "element" or "component" encompass both elements and components comprising one unit and elements and components that comprise more than one subunit unless specifically stated otherwise.

As used herein, all numbers are approximate, and may be varied to account for measurement error and the rounding of significant digits. The use of "about" before certain measured quantities includes variations due to sample impurities, measurement error, human error, and statistical variation, as well as the rounding of significant digits.

As utilized in accordance with the present disclosure, the following terms, unless otherwise indicated, shall be understood to have the following meanings:

The terms "nucleic acid molecule" and "polynucleotide" may be used interchangeably, and refer to a polymer of nucleotides. Such polymers of nucleotides may contain natural and/or non-natural nucleotides, and include, but are not limited to, DNA, RNA, and PNA. "Nucleic acid sequence" refers to the linear sequence of nucleotides that comprise the nucleic acid molecule or polynucleotide.

The terms "polypeptide" and "protein" are used interchangeably to refer to a polymer of amino acid residues, and are not limited to a minimum length. Such polymers of amino acid residues may contain natural or non-natural amino acid residues, and include, but are not limited to, peptides, oligopeptides, dimers, trimers, and multimers of amino acid residues. Both full-length proteins and fragments thereof are encompassed by the definition. The terms also include post-expression modifications of the polypeptide, for example, glycosylation, sialylation, acetylation, phosphorylation, and the like. Furthermore, for purposes of the present invention, a "polypeptide" refers to a protein which includes modifications, such as deletions, additions, and substitutions (generally conservative in nature), to the native sequence, as long as the protein maintains the desired activity. These modifications may be deliberate, as through site-directed mutagenesis, or may be accidental, such as through mutations of hosts which produce the proteins or errors due to PCR amplification. When a polypeptide "consists of" a particular amino acid sequence, it may still contain post-translational modifications, such as glycosylation and sialylation.

The term "FGFR1 extracellular domain" ("FGFR1 ECD") includes full-length FGFR1 ECDs, FGFR1 ECD fragments, and FGFR1 ECD variants. As used herein, the term "FGFR1 ECD" refers to an FGFR1 polypeptide that lacks the intracellular and transmembrane domains, with or without a signal peptide. In some embodiment, the FGFR1 ECD is a human full-length FGFR1 ECD having an amino acid sequence selected from SEQ ID NOs: 1 and 2. The term "full-length FGFR1 ECD", as used herein, refers to an FGFR1 ECD that extends to the last amino acid of the extracellular domain, and may or may not include an N-terminal signal peptide. As defined herein, the last amino acid of the full-length FGFR1 ECD is at position 353. Thus, a human full-length FGFR1 ECD may consist of the amino acid sequence corresponding to SEQ ID NO.: 2 (mature form) or to SEQ ID NO.: 1 (with the signal peptide). As used herein, the term "FGFR1 ECD fragment" refers to an FGFR1 ECD having one or more residues deleted from the N and/or C terminus of the full-length ECD and that retains the ability to bind to FGF-2. The FGFR1 ECD fragment may or may not include an N-terminal signal peptide. In some embodiments, the FGFR1 ECD fragment is a human FGFR1 ECD fragment having an amino acid sequence corresponding to SEQ ID NO.: 4 (mature form) or to SEQ ID NO.: 3 (with the signal peptide).

As used herein, the term "FGFR1 ECD variants" refers to FGFR1 ECDs that contain amino acid additions, deletions, and substitutions and that remain capable of binding to FGF-2. Such variants may be at least 90%, 92%, 95%, 97%, 98%, or 99% identical to the parent FGFR1 ECD. The % identity of two polypeptides can be measured by a similarity score determined by comparing the amino acid sequences of the two polypeptides using the Bestfit program with the default settings for determining similarity. Bestfit uses the local homology algorithm of Smith and Waterman, *Advances in Applied Mathematics* 2:482-489 (1981) to find the best segment of similarity between two sequences. In some embodiments, an FGFR1 ECD variant is at least 95% identical to the sequence of SEQ ID NO: 4.

A polypeptide having an amino acid sequence at least, for example, 95% identical to a reference amino acid sequence of an FGFR1 ECD polypeptide is one in which the amino acid sequence of the polypeptide is identical to the reference sequence except that the polypeptide sequence may include up to five amino acid alterations per each 100 amino acids of the reference polypeptide. In other words, to obtain a polypeptide having an amino acid sequence at least 95% identical to a reference amino acid sequence, up to 5% of the amino acid residues in the reference sequence may be deleted or substituted with another amino acid, or a number of amino acids, up to 5% of the total amino acid residues in the reference sequence, may be inserted into the reference sequence. These alterations of the reference sequence may occur at the N- or C-terminal positions of the reference amino acid sequence or anywhere between those terminal positions, interspersed either individually among residues in the reference sequence, or in one or more contiguous groups within the reference sequence.

As a practical matter, whether any particular polypeptide is at least 70%, 80%, 90%, or 95% identical to, for instance, an amino acid sequence or to a polypeptide sequence encoded by a nucleic acid sequence set forth in the Sequence Listing can be determined conventionally using known computer programs, such the Bestfit program. When using Bestfit or other sequence alignment program to determine whether a particular sequence is, for instance, 95% identical to a reference sequence according to the present invention, the parameters are set, of course, that the percentage of identity is calculated over the full length of the reference amino acid sequence and that gaps in homology of up to 5% of the total number of amino acid residues in the reference sequence are allowed.

As used herein, the terms "hFGFR1-ECD.353" and "hFGFR1.353" may be used interchangeably to refer to the full-length human FGFR1 ECD corresponding to SEQ ID NO: 1 (with signal peptide) or to SEQ ID NO: 2 (without signal peptide; mature form).

As used herein, the terms "hFGFR1-ECD.339" and "hFGFR1.339" may be used interchangeably to refer to the human FGFR1 ECD corresponding to SEQ ID NO: 3 (with signal peptide) or to SEQ ID NO: 4 (without signal peptide; mature form).

Additional hFGFR1 ECDs are described, for example, in U.S. Pat. No. 7,678,890, which is incorporated by reference herein in its entirety for any purpose.

The term "FGFR1 ECD fusion molecule" refers to a molecule comprising an FGFR1 ECD, and one or more "fusion partners." In some embodiments, the FGFR1 ECD and the fusion partner are covalently linked ("fused"). If the fusion partner is also a polypeptide ("the fusion partner polypeptide"), the FGFR1 ECD and the fusion partner polypeptide may be part of a continuous amino acid sequence, and the fusion partner polypeptide may be linked to either the N terminus or the C terminus of the FGFR1 ECD. In such cases, the FGFR1 ECD and the fusion partner polypeptide may be translated as a single polypeptide from a coding sequence that encodes both the FGFR1 ECD and the fusion partner polypeptide (the "FGFR1 ECD fusion protein"). In some embodiments, the FGFR1 ECD and the fusion partner are covalently linked through other means, such as, for example, a chemical linkage other than a peptide bond. Many known methods of covalently linking polypeptides to other molecules (for example, fusion partners) may be used. In other embodiments, the FGFR1 ECD and the fusion partner may be fused through a "linker," which is comprised of at least one amino acid or chemical moiety.

In some embodiments, the FGFR1 ECD polypeptide and the fusion partner are noncovalently linked. In some such embodiments, they may be linked, for example, using binding pairs. Exemplary binding pairs include, but are not limited to, biotin and avidin or streptavidin, an antibody and its antigen, etc.

Exemplary fusion partners include, but are not limited to, an immunoglobulin Fc domain, albumin, and polyethylene glycol. The amino acid sequences of some exemplary Fc domains are shown in SEQ ID NOs: 8 to 10. In some embodiments, an FGFR1 ECD fused to an Fc is referred to as an "hFGFR1 ECD-Fc." In some embodiments, the Fc domain is selected from an IgG1 Fc, an IgG2 Fc, an IgG3 Fc, and an IgG4 Fc.

As used herein, the terms "hFGFR1-ECD.339-Fc", "hFGFR1.339-Fc", and "FP-1039" may be used interchangeably to refer to an amino acid sequence selected from SEQ ID NO: 6 (without signal peptide, mature form) and SEQ ID NO: 5 (with signal peptide). Nonlimiting exemplary cancers that may be treated with hFGFR1-ECD.339-Fc include, but are not limited to, lung cancer, colon cancer, breast cancer, gastric cancer, head and neck cancer, prostate cancer, endometrial cancer, sarcoma, small cell lung cancer, ovarian cancer, Kaposi's sarcoma, Hodgkin's disease, leukemia, non-Hodgkin's lymphoma, neuroblastoma (brain cancer), rhabdomyosarcoma, Wilms' tumor, acute lymphoblastic leukemia, acute lymphoblastic leukemia, bladder cancer, testicular cancer, lymphomas, germ cell tumors, cancers of the colon and rectum, gastrointestinal cancers, gastrointestinal stromal tumor, thyroid cancer, multiple myeloma, pancreatic cancer, mesothelioma, malignant pleural mesothelioma, hematological/lymphatic cancers, malignant peritoneal mesothelioma, esophageal cancer, renal cell carcinoma, glioblastoma multiforme, and liver cancer.

The term "signal peptide" refers to a sequence of amino acid residues located at the N terminus of a polypeptide that facilitates secretion of a polypeptide from a mammalian cell. A signal peptide may be cleaved upon export of the polypeptide from the mammalian cell, forming a mature protein. Signal peptides may be natural or synthetic, and they may be heterologous or homologous to the protein to which they are attached. Exemplary signal peptides include, but are not limited to, FGFR1 signal peptides, such as, for example, the amino acid sequence of SEQ ID NO: 7. Exemplary signal peptides also include signal peptides from heterologous proteins. A "signal sequence" refers to a polynucleotide sequence that encodes a signal peptide. In some embodiments, an FGFR1 ECD lacks a signal peptide. In some embodiments, an FGFR1 ECD includes at least one signal peptide, which may be a native FGFR1 signal peptide or a heterologous signal peptide.

The term "vector" is used to describe a polynucleotide that may be engineered to contain a cloned polynucleotide or polynucleotides that may be propagated in a host cell. A vector may include one or more of the following elements: an origin of replication, one or more regulatory sequences (such as, for example, promoters and/or enhancers) that regulate the expression of the polypeptide of interest, and/or one or more selectable marker genes (such as, for example, antibiotic resistance genes and genes that may be used in colorimetric assays, e.g., β-galactosidase). The term "expression vector" refers to a vector that is used to express a polypeptide of interest in a host cell.

A "host cell" refers to a cell that may be or has been a recipient of a vector or isolated polynucleotide. Host cells may be prokaryotic cells or eukaryotic cells. Exemplary eukaryotic cells include mammalian cells, such as primate or non-primate animal cells; fungal cells; plant cells; and insect cells. Exemplary mammalian cells include, but are not limited to, 293 and CHO cells, and their derivatives, such as 293-6E and DG44 cells, respectively.

The term "isolated" as used herein refers to a molecule that has been separated from at least some of the components with which it is typically found in nature. For example, a polypeptide is referred to as "isolated" when it is separated from at least some of the components of the cell in which it was produced. Where a polypeptide is secreted by a cell after expression, physically separating the supernatant containing the polypeptide from the cell that produced it is considered to be "isolating" the polypeptide. Similarly, a polynucleotide is referred to as "isolated" when it is not part of the larger polynucleotide (such as, for example, genomic DNA or mitochondrial DNA, in the case of a DNA polynucleotide) in which it is typically found in nature, or is separated from at least some of the components of the cell in which it was produced, e.g., in the case of an RNA polynucleotide. Thus, a DNA polynucleotide that is contained in a vector inside a host cell may be referred to as "isolated" so long as that polynucleotide is not found in that vector in nature.

The term "anti-neoplastic composition" refers to a composition useful in treating cancer comprising at least one active therapeutic agent, e.g., an "anti-cancer agent." Examples of therapeutic agents (anti-cancer agents) include, but are not limited to, e.g., chemotherapeutic agents, growth inhibitory agents, cytotoxic agents, agents used in radiation therapy, anti-angiogenic agents, apoptotic agents, anti-tubulin agents, and other agents to treat cancer, such as anti-VEGF antibodies (e.g., bevacizumab, AVASTIN®), anti-HER-2 antibodies (e.g., trastuzumab, HERCEPTIN®), anti-CD20 antibodies (e.g., rituximab, RITUXAN®), an epidermal growth factor receptor (EGFR) antagonist (e.g., a tyrosine kinase inhibitor), HER1/EGFR inhibitors (e.g., erlotinib, TARCEVA®), platelet derived growth factor inhibitors (e.g., GLEEVEC®, imatinib mesylate)), COX-2 inhibitors (e.g., celecoxib), interferons, cytokines, antagonists (e.g., neutralizing antibodies) that bind to one or more of the following targets ErbB2, ErbB3, ErbB4, PDGFR-beta, BlyS, APRIL, BCMA or VEGF receptor(s), TRAIL/Apo2, and other bioactive and organic chemical agents, etc. Combinations thereof are also included in the invention.

A "chemotherapeutic agent" refers to a chemical compound useful in the treatment of cancer. Examples of chemotherapeutic agents include alkylating agents such as thiotepa and cyclophosphamide (CYTOXAN®); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e. g., calicheamicin, especially calicheamicin gamma1I and calicheamicin omega1I (see, e.g., Nicolaou et al., *Angew. Chem Intl. Ed. Engl.*, 33: 183-186 (1994)); CDP323, an oral alpha-4 integrin inhibitor; dynemicin, including dynemicin A; an esperamicin; as well as neocarzinostatin chromophore and related chromoprotein enediyne antibiotic chromophores), aclacinomysins, actinomycin, authramycin, azaserine, bleomycins, cactinomycin, carabicin, carminomycin, carzinophilin, chromomycins, dactinomycin, daunorubicin, detorubicin, 6-diazo-5-oxo-L-norleucine, doxorubicin (including ADRIAMYCIN®, morpholino-doxorubicin, cyanomorpholino-doxorubicin, 2-pyrrolino-doxorubicin, doxorubicin HCl liposome injection (DOXIL®), liposomal doxorubicin TLC D-99 (MYOCET®), pegylated liposomal doxorubicin (CAELYX®), and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate, gemcitabine (GEMZAR®), pemetrexed (ALIMTA®); tegafur (UFTORAL®), capecitabine (XELODA®), an epothilone, and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2'-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoid, e.g., paclitaxel (TAXOL®), albumin-engineered nanoparticle formulation of paclitaxel (ABRAXANE™), and docetaxel (TAXOTERE®); chloranbucil; 6-thioguanine; mercaptopurine; methotrexate; platinum agents such as cisplatin, oxaliplatin (e.g., ELOXATIN®), and carboplatin; vincas, which prevent tubulin polymerization from forming microtubules, including vinblastine (VELBAN®), vincristine (ONCOVIN®), vindesine (ELDISINE®, FILDESIN®), and vinorelbine (NAVELBINE®); etoposide (VP-16); ifosfamide; mitoxantrone; leucovorin; novantrone; edatrexate; daunomycin; aminopterin; ibandronate; topoisomerase inhibitor RFS 2000; difluoromethylornithine (DMFO); retinoids such as retinoic acid, including bexarotene (TARGRETIN®); bisphosphonates such as clodronate (for example, BONEFOS® or OSTAC®), etidronate (DIDROCAL®), NE-58095, zoledronic acid/zoledronate (ZOMETA®), alendronate (FOSAMAX®), pamidronate (AREDIA®), tiludronate (SKELID®), or risedronate (ACTONEL®); troxacitabine (a 1,3-dioxolane nucleoside cytosine analog); antisense oligonucleotides, particularly those that inhibit expression of genes in signaling pathways implicated in aberrant cell proliferation, such as, for example, PKC-alpha, Raf, H-Ras, and epidermal growth factor receptor (EGFR); vaccines such as THERATOPE® vaccine and gene therapy vaccines, for example, ALLOVECTIN® vaccine, LEUVECTIN® vaccine, and VAXID® vaccine; topoisomerase 1 inhibitor (e.g., LURTOTECAN®); rmRH (e.g., ABARELIX®); BAY439006 (sorafenib, NEXAVAR®; Bayer); SU-11248 (sunitinib, SUTENT®, Pfizer); perifosine, COX-2 inhibitor (e.g. celecoxib or etoricoxib), proteosome inhibitor (e.g. PS341) bortezomib (VELCADE®); CCI-779; tipifarnib (R11577); orafenib, ABT510; Bcl-2 inhibitor such as oblimersen sodium (GENASENSE®); pixantrone; EGFR inhibitors (see definition below); tyrosine kinase inhibitors (see definition below); serine-threonine kinase inhibitors such as rapamycin (sirolimus, RAPAMUNE®); farnesyltransferase inhibitors such as lonafarnib (SCH 6636, SARASAR™); and pharmaceutically acceptable salts, acids or derivatives of any of the above; as well as combinations of two or more of the above such as CHOP, an abbreviation for a combined therapy of cyclophosphamide, doxorubicin, vincristine, and prednisolone; and FOLFOX, an abbreviation for a treatment regimen with oxaliplatin (ELOXATIN®) combined with 5-FU and leucovorin.

Chemotherapeutic agents as defined herein include "anti-hormonal agents" or "endocrine therapeutics" which act to regulate, reduce, block, or inhibit the effects of hormones that can promote the growth of cancer. They may be hormones themselves, including, but not limited to: anti-estrogens with mixed agonist/antagonist profile, including, tamoxifen (NOLVADEX®), 4-hydroxytamoxifen, toremifene (FARESTON®), idoxifene, droloxifene, raloxifene (EVISTA®), trioxifene, keoxifene, and selective estrogen receptor modulators (SERMs) such as SERM3; pure anti-estrogens without agonist properties, such as fulvestrant (FASLODEX®), and EM800 (such agents may block estrogen receptor (ER) dimerization, inhibit DNA binding, increase ER turnover, and/or suppress ER levels); aromatase inhibitors, including steroidal aromatase inhibitors such as formestane and exemestane (AROMASIN®), and non-steroidal aromatase inhibitors such as anastrazole (ARIMIDEX®), letrozole (FEMARA®) and aminoglutethimide, and other aromatase inhibitors include vorozole (RIVISOR®), megestrol acetate (MEGASE®), fadrozole, and 4(5)-imidazoles; lutenizing hormone-releasing hormone agonists, including leuprolide (LUPRON® and ELIGARD®), goserelin, buserelin, and tripterelin; sex steroids, including progestins such as megestrol acetate and medroxyprogesterone acetate, estrogens such as diethylstilbestrol and premarin, and androgens/retinoids such as fluoxymesterone, all transretinoic acid and fenretinide; onapristone; anti-progesterones; estrogen receptor down-regulators (ERDs); anti-androgens such as flutamide, nilutamide and bicalutamide; and pharmaceutically acceptable salts, acids or derivatives of any of the above; as well as combinations of two or more of the above.

An "angiogenic factor or agent" refers to a growth factor which stimulates the development of blood vessels, e.g., promote angiogenesis, endothelial cell growth, stability of blood vessels, and/or vasculogenesis, etc. For example, angiogenic factors, include, but are not limited to, e.g., VEGF and members of the VEGF family (VEGF-B, VEGF-C and VEGF-D), PlGF, PDGF family, fibroblast growth factor family (FGFs), TIE ligands (Angiopoietins), ephrins, delta-like ligand 4 (DLL4), del-1, fibroblast growth factors: acidic (aFGF) and basic (bFGF), follistatin, granulocyte colony-stimulating factor (G-CSF), hepatocyte growth factor (HGF)/scatter factor (SF), interleukin-8 (IL-8), leptin, midkine, neuropilins, placental growth factor, platelet-derived endothelial cell growth factor (PD-ECGF), platelet-derived growth factor, especially PDGF-BB or PDGFR-beta, pleiotrophin (PTN), progranulin, proliferin, transforming growth factor-alpha (TGF-alpha), transforming growth factor-beta (TGF-beta), tumor necrosis factor-alpha (TNF-alpha), etc. It would also include factors that accelerate wound healing, such as growth hormone, insulin-like growth factor-I (IGF-I), VIGF, epidermal growth factor (EGF), CTGF and members of its family, and TGF-alpha and TGF-beta. See, e.g., Klagsbrun and D'Amore (1991) *Annu. Rev. Physiol.* 53:217-39; Streit and Detmar (2003) *Oncogene* 22:3172-3179; Ferrara & Alitalo (1999) *Nature Medicine* 5(12):1359-1364; Tonini et al. (2003) *Oncogene*

22:6549-6556 (e.g., Table 1 listing known angiogenic factors); and, Sato (2003) *Int. J. Clin. Oncol.* 8:200-206.

An "anti-angiogenic agent" or "angiogenesis inhibitor" refers to a small molecular weight substance, a polynucleotide (including, e.g., an inhibitory RNA (RNAi or siRNA)), a polypeptide, an isolated protein, a recombinant protein, an antibody, or conjugates or fusion proteins thereof, that inhibits angiogenesis, vasculogenesis, or undesirable vascular permeability, either directly or indirectly. It should be understood that the anti-angiogenic agent includes those agents that bind and block the angiogenic activity of the angiogenic factor or its receptor. For example, an anti-angiogenic agent is an antibody or other antagonist to an angiogenic agent as defined above, e.g., fusion proteins that binds to VEGF such as ZALTRAP™ (Aflibercept), antibodies to VEGF such as AVASTIN® (bevacizumab) or to the VEGF receptor (e.g., KDR receptor or Flt-1 receptor), anti-PDGFR inhibitors such as GLEEVEC® (Imatinib Mesylate), small molecules that block VEGF receptor signaling (e.g., PTK787/ZK2284, SU6668, SUTENT®/SU11248 (sunitinib malate), AMG706, or those described in, e.g., international patent application WO 2004/113304). Anti-angiogenic agents also include native angiogenesis inhibitors, e.g., angiostatin, endostatin, etc. See, e.g., Klagsbrun and D'Amore (1991) *Annu. Rev. Physiol.* 53:217-39; Streit and Detmar (2003) *Oncogene* 22:3172-3179 (e.g., Table 3 listing anti-angiogenic therapy in malignant melanoma); Ferrara & Alitalo (1999) *Nature Medicine* 5(12): 1359-1364; Tonini et al. (2003) *Oncogene* 22:6549-6556 (e.g., Table 2 listing known anti-angiogenic factors); and, Sato (2003) *Int. J. Clin. dOncol.* 8:200-206 (e.g., Table 1 listing anti-angiogenic agents used in clinical trials).

The term "VEGF" or "VEGFA" as used herein refers to the 165-amino acid human vascular endothelial cell growth factor and related 121-, 189-, and 206-amino acid human vascular endothelial cell growth factors, as described by Leung et al. (1989) Science 246:1306, and Houck et al. (1991) Mol. Endocrin, 5:1806, together with the naturally occurring allelic and processed forms thereof. The term "VEGF" also refers to VEGFs from non-human species such as mouse, rat or primate. Sometimes the VEGF from a specific species are indicated by terms such as hVEGF for human VEGF, mVEGF for murine VEGF, and etc. The term "VEGF" is also used to refer to truncated forms of the polypeptide comprising amino acids 8 to 109 or 1 to 109 of the 165-amino acid human vascular endothelial cell growth factor. Reference to any such forms of VEGF may be identified in the present application, e.g., by "VEGF (8-109)," "VEGF (1-109)," "VEGF$_{109}$" or "VEGF165." The amino acid positions for a "truncated" native VEGF are numbered as indicated in the native VEGF sequence. For example, amino acid position 17 (methionine) in truncated native VEGF is also position 17 (methionine) in native VEGF. The truncated native VEGF has binding affinity for the KDR and Flt-1 receptors comparable to native VEGF.

A "VEGF antagonist" refers to a molecule capable of neutralizing, blocking, inhibiting, abrogating, reducing or interfering with VEGF activities including, but not limited to, its binding to one or more VEGF receptors. VEGF antagonists include, without limitation, anti-VEGF antibodies and antigen-binding fragments thereof, receptor molecules and derivatives which bind specifically to VEGF thereby sequestering its binding to one or more receptors, anti-VEGF receptor antibodies, VEGF receptor antagonists such as small molecule inhibitors of the VEGFR tyrosine kinases (e.g., pazopanib) and immunoadhesins that binds to VEGF such as VEGF trap (e.g., aflibercept). The term "VEGF antagonist," as used herein, specifically includes molecules, including antibodies, antibody fragments, other binding polypeptides, peptides, and non-peptide small molecules, that bind to VEGF and are capable of neutralizing, blocking, inhibiting, abrogating, reducing or interfering with VEGF activities. Thus, the term "VEGF activities" specifically includes VEGF mediated biological activities of VEGF.

The term "VEGF trap" as used herein means a protein, such as a fusion molecule, that binds to VEGF and is capable of neutralizing, blocking, inhibiting, abrogating, reducing or interfering with VEGF activities. An example of a VEGF trap is aflibercept.

The term "anti-VEGF antibody" or "an antibody that binds to VEGF" refers to an antibody that is capable of binding to VEGF with sufficient affinity and specificity that the antibody is useful as a diagnostic and/or therapeutic agent in targeting VEGF. Anti-VEGF neutralizing antibodies suppress the growth of a variety of human tumor cell lines in nude mice (Kim et al., *Nature* 362:841-844 (1993); Warren et al., *J. Clin. Invest.* 95:1789-1797 (1995); Borgström et al., *Cancer Res.* 56:4032-4039 (1996); Melnyk et al., *Cancer Res.* 56:921-924 (1996)) and also inhibit intraocular angiogenesis in models of ischemic retinal disorders. Adamis et al., *Arch. Ophthalmol.* 114:66-71 (1996). For example, the anti-VEGF antibody can be used as a therapeutic agent in targeting and interfering with diseases or conditions wherein the VEGF activity is involved. See, e.g., U.S. Pat. Nos. 6,582,959, 6,703,020; WO98/45332; WO 96/30046; WO94/10202, WO2005/044853; EP 0666868B1; US Patent Applications 20030206899, 20030190317, 20030203409, 20050112126, 20050186208, and 20050112126; Popkov et al., *Journal of Immunological Methods* 288:149-164 (2004); and WO2005012359. The antibody selected will normally have a sufficiently strong binding affinity for VEGF. For example, the antibody may bind hVEGF with a $K_d$ value of between 100 nM-1 pM. Antibody affinities may be determined by a surface plasmon resonance based assay (such as the BIAcore assay as described in PCT Application Publication No. WO2005/012359); enzyme-linked immunoabsorbent assay (ELISA); and competition assays (e.g. RIA's), for example. The antibody may be subjected to other biological activity assays, e.g., in order to evaluate its effectiveness as a therapeutic. Such assays are known in the art and depend on the target antigen and intended use for the antibody. Examples include the HUVEC inhibition assay; tumor cell growth inhibition assays (as described in WO 89/06692, for example); antibody-dependent cellular cytotoxicity (ADCC) and complement-mediated cytotoxicity (CDC) assays (U.S. Pat. No. 5,500,362); and agonistic activity or hematopoiesis assays (see WO 95/27062). An anti-VEGF antibody will usually not bind to other VEGF homologues such as VEGF-B, VEGF-C, VEGF-D or VEGF-E, nor other growth factors such as PlGF, PDGF or bFGF.

In one embodiment, anti-VEGF antibodies include a monoclonal antibody that binds to the same epitope as the monoclonal anti-VEGF antibody A4.6.1 produced by hybridoma ATCC HB 10709; a recombinant humanized anti-VEGF monoclonal antibody (see Presta et al. (1997) *Cancer Res.* 57:4593-4599), including but not limited to the antibody known as "bevacizumab" also known as "rhuMAb VEGF" or "AVASTIN®." AVASTIN® is presently commercially available. Nonlimiting exemplary cancers that may be treated with bevacizumab include non-small cell lung cancer, colorectal cancer, breast cancer, renal cancer, ovarian cancer, glioblastoma multiforme, pediatric osteosarcoma, gastric cancer and pancreatic cancer. Bevacizumab comprises mutated human IgG$_1$ framework regions and antigen-binding complementarity-determining regions from the murine antibody A.4.6.1 that blocks binding of human VEGF to its receptors. Bevacizumab and other humanized anti-VEGF antibodies are further described in U.S. Pat. Nos. 6,884,879, and 7,169,901. Additional anti-VEGF antibodies are described in PCT Application Publication Nos. WO2005/012359 and WO2009/073160; U.S. Pat. Nos. 7,060,269, 6,582,959, 6,703,020; 6,054,297; WO98/45332; WO 96/30046; WO94/10202; EP 0666868B1; U.S. Patent Application Publication Nos. 2006009360, 20050186208, 20030206899, 20030190317, 20030203409, and 20050112126; and Popkov et al., *Journal of Immunological Methods* 288:149-164 (2004).

As used herein, "VEGF-resistant tumor" and "VEGF-resistant cancer" refer to a tumor or cancer with a higher level of FGF2 than a reference sample, cell, or tissue. In some embodiments, a VEGF-resistant tumor has a higher level of FGF2 compared to the level of VEGF. In some embodiments, the ratio of FGF2 level to VEGF level in a VEGF-resistant tumor sample is greater than 1. In some embodiments, a subject with a VEGF-resistant tumor has previously been treated with at least one therapeutic agent selected from pazopanib, bevacizumab, axitinib, aflibercept, sorafenib, and sunitinib.

As used herein, "pazopanib-resistant tumor" and "pazopanib-resistant cancer" refer to a tumor or cancer that initially responded to pazopanib but no longer responds or responds to a lesser extent. In some embodiments, a pazopanib-resistant tumor or cancer no longer regresses, or even progresses, in the presence of pazopanib.

The terms "subject" and "patient" are used interchangeably herein to refer to a mammal. In some embodiments, the subject or patient is a human. In other embodiments, methods of treating other mammals, including, but not limited to, rodents, simians, felines, canines, equines, bovines, porcines, ovines, caprines, mammalian laboratory animals, mammalian farm animals, mammalian sport animals, and mammalian pets, are also provided.

The term "sample" or "patient sample" as used herein, refers to a composition that is obtained or derived from a subject of interest that contains a cellular and/or other molecular entity that is to be characterized and/or identified, for example based on physical, biochemical, chemical and/or physiological characteristics. For example, the phrase "disease sample" and variations thereof refers to any sample obtained from a subject of interest that would be expected or is known to contain the cellular and/or molecular entity that is to be characterized. By "tissue or cell sample" is meant a collection of similar cells obtained from a tissue of a subject or patient. The source of the tissue or cell sample may be solid tissue as from a fresh, frozen and/or preserved organ or tissue sample or biopsy or aspirate; blood or any blood constituents; bodily fluids such as cerebral spinal fluid, amniotic fluid, peritoneal fluid, or interstitial fluid; cells from any time in gestation or development of the subject. The tissue sample may also be primary or cultured cells or cell lines. Optionally, the tissue or cell sample is obtained from a disease tissue/organ. The tissue sample may contain compounds which are not naturally intermixed with the tissue in nature such as preservatives, anticoagulants, buffers, fixatives, nutrients, antibiotics, or the like.

A "reference sample", "reference cell", or "reference tissue", as used herein, refers to a sample, cell or tissue obtained from a source known, or believed, not to be afflicted with the disease or condition for which a method or composition of the invention is being used to identify. In some embodiments, a reference sample, reference cell or reference tissue is obtained from a healthy part of the body of the same subject or patient in whom a disease or condition is being identified using a composition or method of the invention. In some embodiments, a reference sample, reference cell or reference tissue is obtained from a healthy part of the body of one or more individuals who are not the subject or patient in whom a disease or condition is being identified using a composition or method of the invention.

"Cancer" and "tumor," as used herein, are interchangeable terms that refer to any abnormal cell or tissue growth or proliferation in an animal. As used herein, the terms "cancer" and "tumor" encompass solid and hematological/lymphatic cancers and also encompass malignant, pre-malignant, and benign growth, such as dysplasia. Examples of cancer include but are not limited to, carcinoma, lymphoma, blastoma, sarcoma, and leukemia. More particular non-limiting examples of such cancers include squamous cell cancer, small-cell lung cancer, pituitary cancer, esophageal cancer, astrocytoma, soft tissue sarcoma, non-small cell lung cancer, adenocarcinoma of the lung, squamous carcinoma of the lung, cancer of the peritoneum, hepatocellular cancer, gastrointestinal cancer, gastrointestinal stromal tumor, pancreatic cancer, glioblastoma, cervical cancer, ovarian cancer, liver cancer, bladder cancer, hepatoma, breast cancer, colon cancer, colorectal cancer, stomach cancer, endometrial or uterine carcinoma, salivary gland carcinoma, kidney cancer, renal cancer, liver cancer, prostate cancer, vulval cancer, thyroid cancer, hepatic carcinoma, brain cancer, endometrial cancer, testis cancer, cholangiocarcinoma, gallbladder carcinoma, gastric cancer, melanoma, mesothelioma, and various types of head and neck cancer.

A "cell with a higher level of FGF2 compared to the level of VEGF" refers to a cell that has a higher level of FGF2 mRNA or protein than the level of VEGF mRNA or protein in the cell. A "cancer with a higher level of FGF2 compared to the level of VEGF" refers to a cancer in which at least a portion of the cells have a higher level of FGF2 mRNA or protein than the level of VEGF mRNA or protein. In some embodiments, "at least a portion of the cells" is at least 10%, at least 20%, at least 30%, at least 40%, at least 50%, at least 60%, at least 70%, at least 80%, or at least 90% of the cells of a cancer sample. In some embodiments, a cell with a higher level of FGF2 compared to the level of VEGF or a cancer in which at least a portion of the cells have a higher level of FGF2 compared to the level of VEGF has a ratio of FGF2 to VEGF of greater than 1. In some embodiments, a cell with a higher level of FGF2 compared to the level of VEGF or a cancer in which at least a portion of the cells have a higher level of FGF2 compared to the level of VEGF has 5%, 7%, 10%, 12%, 15%, 17%, 20%, or 25% more FGF2 than VEGF. In some embodiments, the level of FGF2 and VEGF is an mRNA level. In some such embodiments, the level is determined by a method selected from quantitative RT-PCR, microarray, digital PCT, RNA-Seq, RNase Protection Assay (RPA), Northern blot, and in situ hybridization (ISH). In some embodiments, the level is determined by quantitative RT-PCR. In some embodiments, the level is determined by microarray. In some embodiments, the level of FGF2 and VEGF is a protein level. In some such embodiments, the level is determined by a method selected from immunohistochemistry, ELISA, mass spectrometry, reverse phase protein array (RPPA), antibody array, nano-immuno assay, Western blot, and capillary protein analysis assay. In some embodiments, the level is determined by immunohistochemistry.

A "cell with a lower level of FGF2 compared to the level of VEGF" refers to a cell that has a lower level of FGF2 mRNA or protein than the level of VEGF mRNA or protein in the cell. A "cancer with a lower level of FGF2 compared to the level of VEGF" refers to a cancer in which at least a portion of the cells have a lower level of FGF2 mRNA or protein than the level of VEGF mRNA or protein. In some embodiments, at least 10%, at least 20%, at least 30%, at least 40%, at least 50%, at least 60%, at least 70%, at least 80%, or at least 90% of the cells of a cancer sample have a lower level of FGF2 mRNA or protein compared to the level of VEGF mRNA or protein. In some embodiments, a cell with a lower level of FGF2 compared to the level of VEGF or a cancer in which at least a portion of the cells have a lower level of FGF2 compared to the level of VEGF has a ratio of FGF2 to VEGF of less than 1. In some embodiments, a cell with a lower level of FGF2 compared to the level of VEGF or a cancer in which at least a portion of the cells have a lower level of FGF2 compared to the level of VEGF has 5%, 7%, 10%, 12%, 15%, 17%, 20%, or 25% less FGF2 than VEGF. In some embodiments, the level of FGF2 and VEGF is an mRNA level. In some such embodiments, the level is determined by a method selected from quantitative RT-PCR, microarray, digital PCT, RNA-Seq, RNase Protection Assay (RPA), Northern blot, and in situ hybridization (ISH). In some embodiments, the level is determined by quantitative RT-PCR. In some embodiments, the level is determined by microarray. In some embodiments, the level of FGF2 and VEGF is an protein level. In some such embodiments, the level is determined by a method selected from immunohistochemistry, ELISA, mass spectrometry, reverse phase protein array (RPPA), antibody array, nano-immuno assay, Western blot, and capillary protein analysis assay. In some embodiments, the level is determined by immunohistochemistry.

"Treatment," as used herein, includes any administration or application of a therapeutic for condition in a mammal, including a human, and includes inhibiting the condition or progression of the condition, inhibiting or slowing the condition or its progression, arresting its development, partially or fully relieving the condition, or curing the condition, for example, by causing regression, or restoring or repairing a lost, missing, or defective function; or stimulating an inefficient process. In some embodiments, "treatment" refers to clinical intervention in an attempt to alter the natural course of the individual or cell being treated, and can be performed either for prophylaxis or during the course of clinical pathology. Desirable effects of treatment include preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis.

An "effective amount" or "therapeutically effective amount" of a molecule or a combination of molecules means an amount that is sufficient to treat a condition and/or to inhibit growth of tumor cells in at least a subset of subjects when given alone or in combination with other treatments. In certain embodiments, a therapeutically effective amount refers to an amount effective, at dosages and for periods of time necessary, to achieve the desired therapeutic or prophylactic result. A therapeutically effective amount of FGFR1 fusion protein of the invention may vary according to factors such as the disease state, age, sex, and weight of the individual, and the ability of FGFR1 fusion protein to elicit a desired response in the individual. A therapeutically effective amount is also one in which any toxic or detrimental effects of the FGFR1 fusion proteins are outweighed by the therapeutically beneficial effects. In the case of cancer, the effective amount of the drug may reduce the number of cancer cells; reduce the tumor size; inhibit (i.e., slow to some extent and typically stop) cancer cell infiltration into peripheral organs; inhibit (i.e., slow to some extent and typically stop) tumor metastasis; inhibit, to some extent, tumor growth; allow for treatment of the tumor, and/or relieve to some extent one or more of the symptoms associated with the disorder. To the extent the drug may prevent growth and/or kill existing cancer cells, it may be cytostatic and/or cytotoxic.

A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount will be less than the therapeutically effective amount.

The terms "inhibition" or "inhibit" refer to a decrease or cessation of any phenotypic characteristic or to the decrease or cessation in the incidence, degree, or likelihood of that characteristic. Nonlimiting exemplary inhibition includes inhibition of tumor growth.

The terms "benefit", "clinical benefit", "responsiveness", and "therapeutic responsiveness" as used herein in the context of benefiting from or responding to administration of a therapeutic agent, can be measured by assessing various endpoints, e.g., inhibition, to some extent, of disease progression, including slowing down and complete arrest; reduction in the number of disease episodes and/or symptoms; reduction in lesion size; inhibition (i.e., reduction, slowing down or complete stopping) of disease cell infiltration into adjacent peripheral organs and/or tissues; inhibition (i.e. reduction, slowing down or complete stopping) of disease spread; decrease of auto-immune response, which may, but does not have to, result in the regression or ablation of the disease lesion; relief, to some extent, of one or more symptoms associated with the disorder; increase in the length of disease-free presentation following treatment, e.g., progression-free survival; increased overall survival; higher response rate; and/or decreased mortality at a given point of time following treatment.

Administration "in combination with" one or more further therapeutic agents includes concurrent (including simultaneous) and consecutive (i.e., sequential) administration in any order.

A "pharmaceutically acceptable carrier" refers to a non-toxic solid, semisolid, or liquid filler, diluent, encapsulating material, formulation auxiliary, or carrier conventional in the art for use with a therapeutic agent that together comprise a "pharmaceutical composition" for administration to a subject. A pharmaceutically acceptable carrier is non-toxic to recipients at the dosages and concentrations employed and is compatible with other ingredients of the formulation. The pharmaceutically acceptable carrier is appropriate for the formulation employed. For example, if the therapeutic agent is to be administered orally, the carrier may be a gel capsule. If the therapeutic agent is to be administered subcutaneously, the carrier ideally is not irritable to the skin and does not cause injection site reaction.

Therapeutic Compositions and Methods

Methods of Treating Cancer Using FGFR1 ECDs and/or FGFR1 ECD Fusion Molecules

In some embodiments, the invention provides methods of treating cancers in which at least a portion of the cancer cells have a higher level of FGF2 compared to the level of VEGF. In some embodiments, at least 10%, at least 20%, at least 30%, at least 40%, at least 50%, at least 60%, at least 70%, at least 80%, or at least 90% of the cells of a cancer sample have a higher level of FGF2 mRNA or protein compared to the level of VEGF mRNA or protein. Such cancers have been found, in some embodiments, to be particularly responsive to treatment with a fibroblast growth factor receptor 1 (FGFR1) extracellular domain (ECD) or FGFR1 ECD fusion molecule. Accordingly, in some embodiments, a method of treating cancer having a higher level of FGF2 compared to the level of VEGF comprises administering a therapeutically effective amount of an FGFR1 ECD or an FGFR1 ECD fusion molecule to the subject. In some embodiments, a method of treating cancer in a subject comprises administering a therapeutically effective amount of a fibroblast growth factor receptor 1 (FGFR1) extracellular domain (ECD) or an FGFR1 ECD fusion molecule to the subject, wherein, prior to administration of the FGFR1 ECD or FGFR1 ECD fusion molecule, at least a portion of the cells of the cancer have been determined to have a higher level of FGF2 compared to the level of VEGF. In some embodiments, at least 10%, at least 20%, at least 30%, at least 40%, at least 50%, at least 60%, at least 70%, at least 80%, or at least 90% of the cells of a cancer sample have been determined to have a higher level of FGF2 mRNA or protein compared to the level of VEGF mRNA or protein. In such methods, a higher level of FGF2 compared to the level of VEGF in a cancer is indicative of therapeutic responsiveness by the cancer to an FGFR1 ECD or FGFR1 ECD fusion molecule. In some embodiments, a method comprises administering a therapeutically effective amount of an FGFR1 ECD or an FGFR1 ECD fusion molecule and a therapeutically effective amount of at least one anti-angiogenic agent to the subject. In some embodiments, the anti-angiogenic agent is a VEGF antagonist. In some embodiments, the VEGF antagonist is selected from pazopanib, bevacizumab, axitinib, aflibercept, sorafenib, or sunitinib. In some embodiments, the VEGF antagonist is selected from pazopanib, sorafenib, and axitinib.

In some embodiments, the invention provides methods of treating cancers in which at least a portion of the cancer cells have a lower level of FGF2 compared to the level of VEGF. In some embodiments, at least 10%, at least 20%, at least 30%, at least 40%, at least 50%, at least 60%, at least 70%, at least 80%, or at least 90% of the cells of a cancer sample have a lower level of FGF2 mRNA or protein compared to the level of VEGF mRNA or protein. In some embodiments, the level is mRNA level. In some embodiments, the level is protein level. In some embodiments, a method of treating cancer having a lower level of FGF2 compared to the level of VEGF comprises administering a therapeutically effective amount of an FGFR1 ECD or an FGFR1 ECD fusion molecule and a therapeutically effective amount of at least one anti-angiogenic agent to the subject. In some embodiments, a method of treating cancer in a subject comprises administering a therapeutically effective amount of a fibroblast growth factor receptor 1 (FGFR1) extracellular domain (ECD) or an FGFR1 ECD fusion molecule and a therapeutically effective amount of at least one anti-angiogenic agent to the subject, wherein, prior to administration of the FGFR1 ECD or FGFR1 ECD fusion molecule and at least one anti-angiogenic agent, at least a portion of the cells of the cancer have been determined to have a lower level of FGF2 compared to the level of VEGF. In some embodiments, at least 10%, at least 20%, at least 30%, at least 40%, at least 50%, at least 60%, at least 70%, at least 80%, or at least 90% of the cells of a cancer sample have been determined to have a lower level of FGF2 mRNA or protein compared to the level of VEGF mRNA or protein. In some embodiments, the anti-angiogenic agent is a VEGF antagonist. In some embodiments, the VEGF antagonist is selected from pazopanib, bevacizumab, axitinib, aflibercept, sorafenib, or sunitinib. In some embodiments, the VEGF antagonist is selected from pazopanib, sorafenib, and axitinib.

In some embodiments, the cancer is selected from prostate cancer, breast cancer, colorectal cancer, stomach cancer, lung cancer, brain cancer, ovarian cancer, endometrial cancer, head and neck cancer, laryngeal cancer, liver cancer, renal cancer, glioblastoma, and pancreatic cancer. In certain embodiments, the cancer is selected from breast cancer, esophageal cancer, and lung cancer. In some embodiments, the cancer is renal cancer, such as renal cell carcinoma. In some embodiments, the cancer is liver cancer, such as hepatocellular carcinoma. In some embodiments, the cancer is lung cancer. In some embodiments, the lung cancer is selected from non-small cell lung cancer and small cell lung cancer. In some embodiments, the lung cancer is squamous cell carcinoma. In some embodiments, the cancer is head and neck cancer. In some embodiments, the head and neck cancer is squamous cell carcinoma of the head and neck. In some embodiments, the cancer is selected from kidney cancer (such as renal cell carcinoma), liver cancer (such as hepatocellular carcinoma), glioblastoma, and mesothelioma. In some embodiments, the cancer is renal cell carcinoma. In some embodiments, the cancer is hepatocellular carcinoma. In some embodiments, the cancer is mesothelioma. In some embodiments, the cancer is glioblastoma.

In some embodiments, the FGFR1 ECD has an amino acid sequence selected from SEQ ID NOs: 1 to 4. In some embodiments, the FGFR1 ECD has an amino acid sequence selected from SEQ ID NOs: 2 and 4. In some embodiments, the FGFR1 ECD fusion molecule has an amino acid sequence selected from SEQ ID NOs: 5 and 6. In some embodiments, the FGFR1 ECD fusion molecule is FGFR1 ECD.339-Fc with an amino acid sequence of SEQ ID NO: 6.

In some embodiments, an FGFR1 ECD or FGFR1 ECD fusion molecule is administered with one or more additional anti-cancer therapies. Examples of the additional anti-cancer therapies include, without limitation, surgery, radiation therapy (radiotherapy), biotherapy, immunotherapy, and chemotherapy or a combination of these therapies. In addition, cytotoxic agents, anti-angiogenic and anti-proliferative agents can be used in combination with the FGFR1 ECD or FGFR1 ECD fusion molecule. In certain aspects of any of the methods and uses, the invention provides treating cancer by administering therapeutically effective amounts of an FGFR1 ECD and/or FGFR1 ECD fusion molecule and one or more chemotherapeutic agents to a subject. In some embodiments, the subject's cancer has not previously been treated. A variety of chemotherapeutic agents may be used in the combined treatment methods and uses of the invention. An exemplary and non-limiting list of chemotherapeutic agents contemplated is provided herein under "Definitions."

In some embodiments, the invention provides methods of treating cancer, by administering therapeutically effective amounts of an FGFR1 ECD and/or FGFR1 ECD fusion molecule and one or more anti-angiogenic agent(s) to a subject. In some embodiments, the invention provides treating cancer, by administering therapeutically effective amounts of an FGFR1 ECD and/or FGFR1 ECD fusion molecule and one or more VEGF antagonists to a subject. In some embodiments, the invention provides treating cancer, by administering therapeutically effective amounts of an FGFR1 ECD and/or FGFR1 ECD fusion molecule and one or more VEGF antagonists in combination with one or more chemotherapeutic agents to a subject. In some embodiments, the one or more VEGF antagonists are anti-VEGF antibodies and/or VEGF traps. In some embodiments, the VEGF antagonist is selected from pazopanib, bevacizumab, axitinib, aflibercept, sorafenib, or sunitinib. In some embodiments, the VEGF antagonist is selected from pazopanib, sorafenib, and axitinib.

In some embodiments, methods of treating cancer comprising administering to a subject an FGFR1 ECD and/or FGFR1 ECD fusion molecule in combination with at least one additional therapeutic agent selected from docetaxel, paclitaxel, vincristine, carboplatin, cisplatin, oxaliplatin, doxorubicin, 5-fluorouracil (5-FU), leucovorin, pemetrexed, sorafenib, sunitinib, axitinib, pazopanib, etoposide, topotecan, a VEGF antagonist, an anti-VEGF antibody, a VEGF trap, aflibercept, and bevacizumab are provided. In another example, methods of treating cancer comprising administering to a subject an FGFR1-ECD.339-Fc in combination with at least one additional therapeutic agent selected from docetaxel, paclitaxel, vincristine, carboplatin, cisplatin, oxaliplatin, doxorubicin, 5-fluorouracil (5-FU), leucovorin, pemetrexed, sorafenib, sunitinib, axitinib, pazopanib, etoposide, topotecan, a VEGF antagonist, an anti-VEGF antibody, a VEGF trap, aflibercept, and bevacizumab are provided. In some embodiments, methods of treating cancer comprising administering to a subject an FGFR1-ECD.339-Fc and docetaxel are provided. In some embodiments, methods of treating cancer comprising administering to a subject an FGFR1-ECD.339-Fc, paclitaxel, and carboplatin are provided. In some embodiments, methods of treating cancer comprising administering to a subject an FGFR1-ECD.339-Fc, pemetrexed, and cisplatin are provided. In some embodiments, the cancer is selected from liver cancer (including hepatocellular carcinoma), kidney cancer (including renal cell carcinoma), glioblastoma, and mesothelioma. In some embodiments, the cancer is renal cell carcinoma. In some embodiments, the cancer is hepatocellular carcinoma. In some embodiments, the cancer is mesothelioma. In some embodiments, the cancer is glioblastoma.

In some embodiments, methods of treating cancer are provided, comprising administering to a subject with cancer an FGFR1 ECD or FGFR1 ECD fusion molecule, wherein the subject has previously been treated with at least one therapeutic agent selected from pazopanib, bevacizumab, axitinib, aflibercept, sorafenib, and sunitinib. In some embodiments, the subject has previously been treated with at least one therapeutic agent selected from axitinib, pazopanib, and sorafenib. In some embodiments, the subject has previously been treated with pazopanib. In some embodiments, the subject's cancer has become pazopanib-resistant during or following pazopanib treatment. In some embodiments, methods of treating pazopanib-resistant cancer are provided, comprising administering to a subject with pazopanib-resistant cancer an FGFR1 ECD or FGFR1 ECD fusion molecule. In some embodiments, the method comprises administering pazopanib and an FGFR1 ECD or FGFR1 ECD fusion molecule.

In some such embodiments, the subject has a VEGF-resistant cancer. A VEGF-resistant cancer, in some embodiments, expresses a high level of FGF2 and/or has an FGF2/VEGF ratio of greater than 1. In some embodiments, the subject with a VEGF-resistant cancer has previously been treated with at least one therapeutic agent selected from pazopanib, bevacizumab, axitinib, aflibercept, sorafenib, and sunitinib. In some embodiments, at least one therapeutic agent is selected from pazopanib and sorafenib In some embodiments, the FGFR1 ECD or FGFR1 ECD fusion molecule is administered in combination with axitinib.

In some embodiments, a subject is considered to have been previously treated with an agent when the subject has received a full or partial course of treatment with the agent, alone or in combination with one or more additional agents. In some such embodiments, the subject may not have responded to the agent or combination of agents, or may have initially responded to the agent or combination of agents, but may have become less responsive, or may have become nonresponsive, to the agent or combination of agents. Responsiveness may be determined, for example, according to the growth and/or metastasis of the cancer being treated.

In some embodiments, the cancer (including a VEGF-resistant cancer) is selected from prostate cancer, breast cancer, colorectal cancer, stomach cancer, lung cancer, brain cancer, ovarian cancer, endometrial cancer, head and neck cancer, laryngeal cancer, liver cancer, renal cancer, glioblastoma, mesothelioma, and pancreatic cancer. In some embodiments, the cancer (including a VEGF-resistant cancer) is renal cancer, such as renal cell carcinoma. In some embodiments, the cancer (including a VEGF-resistant cancer) is liver cancer, such as hepatocellular carcinoma. In some embodiments, the cancer (including a VEGF-resistant cancer) is mesothelioma.

In some embodiments, methods of reducing blood vessel density in a solid cancer are provided, comprising administering to a subject with the cancer an FGFR1 ECD or FGFR1 ECD fusion molecule. In some embodiments, methods of reducing blood vessel density in a solid cancer are provided, wherein the cancer has a higher level of FGF2 compared to the level of VEGF, wherein the method comprises administering to a subject with the cancer an FGFR1 ECD or FGFR1 ECD fusion molecule. In some embodiments, methods of reducing blood vessel density in a VEGF-resistant solid cancer are provided, comprising administering to a subject with the cancer an FGFR1 ECD or FGFR1 ECD fusion molecule. In some embodiments, the cancer is selected from kidney cancer (such as renal cell carcinoma), liver cancer (such as hepatocellular carcinoma), lung cancer, colon cancer, liver cancer, breast cancer, stomach cancer, ovarian cancer, endometrial cancer, esophageal cancer, head and neck cancer, glioblastoma, mesothelioma, and prostate cancer. In some embodiments, the cancer is selected from kidney cancer (such as renal cell carcinoma), liver cancer (such as hepatocellular carcinoma), glioblastoma, and mesothelioma. In some embodiments, the cancer is renal cell carcinoma. In some embodiments, the cancer is hepatocellular carcinoma. In some embodiments, the cancer is mesothelioma.

In some embodiments, blood vessel density is determined by methods in the art. In some embodiments, blood vessel density is determined as described in Example 11. In some embodiments, blood vessel density is determined in the whole tumor sample.

Pharmaceutical compositions comprising FGFR1 ECD and/or FGFR1 ECD fusion molecules (e.g., FGFR1-ECD.339-Fc) are administered in a therapeutically effective amount for the specific indication. The therapeutically effective amount is typically dependent on the weight of the subject being treated, his or her physical or health condition, the extensiveness of the condition to be treated, and/or the age of the subject being treated. In general, an FGFR1 ECD and/or FGFR1 ECD fusion molecule (e.g., FGFR1-ECD.339-Fc) is to be administered in an amount in the range of about 50 µg/kg body weight to about 100 mg/kg body weight per dose. Optionally, the FGFR1 ECD and/or FGFR1 ECD fusion molecule (e.g., FGFR1-ECD.339-Fc) can be administered in an amount in the range of about 100 µg/kg body weight to about 30 mg/kg body weight per dose. Further optionally, the FGFR1 ECD and/or FGFR1 ECD fusion molecule (e.g., FGFR1-ECD.339-Fc) can be administered in an amount in the range of about 0.5 mg/kg body weight to about 20 mg/kg body weight per dose, calculated using an extinction coefficient of 1.42 mL/mg*cm. In certain embodiments, the FGFR1 ECD and/or FGFR1 ECD fusion molecule (e.g., FGFR1-ECD.339-Fc) is administered at a dose of about 8 mg/kg body weight to about 20 mg/kg body weight, calculated using an extinction coefficient of 1.42 mL/mg*cm. In some embodiments, the FGFR1 ECD and/or FGFR1 ECD fusion molecule (e.g., FGFR1-ECD.339-Fc) is administered at a dose of about 8 mg/kg body weight to about 16 mg/kg body weight (or about 10 mg/kg body weight to about 20 mg/kg body weight when calculated using an extinction coefficient of 1.11 mL/mg*cm). In some embodiments, the FGFR1 ECD and/or FGFR1 ECD fusion molecule (e.g., FGFR1-ECD.339-Fc) is administered at a dose of about 8 mg/kg body weight, about 10 mg/kg body weight, about 11 mg/kg body weight, about 12 mg/kg body weight, about 13 mg/kg body weight, about 14 mg/kg body weight, about 15 mg/kg body weight, about 16 mg/kg body weight, about 17 mg/kg body weight, about 18 mg/kg body weight, about 19 mg/kg body weight, or about 20 mg/kg body weight, calculated using an extinction coefficient of 1.42 mL/mg*cm. In some embodiments, the FGFR1 fusion protein is administered at a dose of about 10 mg/kg body weight as calculated using an extinction coefficient of 1.11 mL/mg*cm. In other embodiments, the FGFR1 fusion protein is administered at a dose of about 20 mg/kg body weight as calculated using an extinction coefficient of 1.11 mL/mg*cm. The FGFR1 ECD and/or FGFR1 ECD fusion molecules may also be administered at ranges from one of the above doses to another. In some embodiments, dosages may be administered twice a week, weekly, every other week, at a frequency between weekly and every other week, every three weeks, every four weeks, or every month.

In certain embodiments, dosages of the FGFR1 ECD and/or FGFR1 ECD fusion molecules can be calculated in two ways depending on the extinction coefficient (EC) used. The extinction coefficient differs depending on whether the glycosylation of the proteins is taken into account. In one embodiment, the extinction coefficient based on the amino acid composition of FGFR1-ECD.339-Fc, for example, is 1.42 mL/mg*cm. In another embodiment, when the carbohydrate portion as well as the amino acid portion of FGFR1-ECD.339-Fc is accounted for, the extinction coefficient is 1.11 mL/mg*cm. Calculation of the FGFR1-ECD.339-Fc dose using an EC of 1.11 mL/mg*cm increases the calculated dose by 28%, as shown in Table 1. Although the doses calculated using the two extinction coefficients are different, the molar concentrations, or the actual amounts of drug administered, are identical. Unless otherwise noted, the doses disclosed herein are each calculated using the extinction coefficient that does not take account of glycosylation. How these dosages compare to those calculated using the extinction coefficient that takes account of glycosylation for FGFR1-ECD.339-Fc is shown in Table 1. As can be seen from Table 1, a dosage of about 8 mg/kg (e.g., 7.8 and 8.0) using an EC of 1.42 mL/mg*cm herein corresponds to a dosage of about 10 mg/kg (e.g. 10.0 and 10.2) when calculated using an EC of 1.11 mL/mg*cm. A dosage of about 16 mg/kg (e.g. 15.6 and 16.0 mg/kg) using an EC of 1.42 mL/mg*cm herein corresponds to a dosage of about 20 mg/kg (e.g. 20.0 and 20.5) when calculated using an EC of 1.11 mL/mg*cm. As noted in the "Definitions" section above, measured numbers provided herein are approximate and encompass values having additional significant digits that are rounded off. For instance, 8 mg/kg encompasses values with two significant digits such as 7.6, 7.8, 8.0, 8.2, 8.4, and 8.45, each of which round to 8. Likewise, a value such as 16 mg/kg encompasses values with three significant digits that round to 16, such as, for example 15.6 and 16.0.

TABLE 1

Conversion of FGFR1-ECD.339-FC Dose

| Dose[a] EC = 1.42 mL/mg * cm | Dose[a] EC = 1.11 mL/mg * cm |
|---|---|
| 0.5 | 0.6 |
| 0.75 | 1.0 |
| 1.0 | 1.3 |
| 2.0 | 2.6 |
| 3.0 | 3.8 |
| 4.0 | 5.1 |
| 5.0 | 6.4 |
| 6.0 | 7.7 |
| 7.0 | 9.0 |
| 7.8 | 10.0 |
| 8.0 | 10.2 |
| 9.0 | 11.5 |
| 10.0 | 12.8 |
| 11.0 | 14.1 |
| 12.0 | 15.4 |
| 13.0 | 16.6 |
| 14.0 | 17.9 |
| 15.0 | 19.2 |
| 15.6 | 20.0 |
| 16.0 | 20.5 |
| 17.0 | 21.8 |
| 18.0 | 23.0 |
| 19.0 | 24.3 |
| 20.0 | 25.6 |
| 30.0 | 38.4 |

[a]Doses shown in mg/kg.

The pharmaceutical compositions comprising FGFR1 ECDs, FGFR1 ECD fusion molecules, and/or at least one additional therapeutic agent can be administered as needed to subjects. In certain embodiments, an effective dose of a therapeutic molecule is administered to a subject one or more times. In various embodiments, an effective dose of a therapeutic molecule is administered to the subject at least once every two months, at least once a month, at least twice a month, once a week, twice a week, or three times a week. In various embodiments, an effective dose of a therapeutic molecule is administered to the subject for at least a week, at least a month, at least three months, at least six months, or at least a year.

In certain embodiments, the combined administration of an FGFR1 ECDs, FGFR1 ECD fusion molecule and at least one additional therapeutic agent includes concurrent administration, including simultaneous administration, using separate formulations or a single pharmaceutical formulation, as well as consecutive administration in any order. Optionally there is a time period while both (or all) active agents simultaneously exert their biological activities. Therapeutically effective amounts of therapeutic agents administered in combination with the FGFR1 ECD and/or FGFR1 ECD fusion molecule (e.g., FGFR1-ECD.339-Fc) will be at the physician's or veterinarian's discretion. Dosage administration and adjustment is done to achieve maximal management of the conditions to be treated. The dose will additionally depend on such factors as the type of therapeutic agent to be used, the specific patient being treated, the stage of the disease, and the desired aggressiveness of the treatment regime.

In certain embodiments, a patient is treated with a combination of the FGFR1 ECD and/or FGFR1 ECD fusion molecule (e.g., FGFR1-ECD.339-Fc) and an anti-angiogenic agent. In some embodiments, the anti-angiogenic agent is a VEGF antagonist. In some embodiments, the VEGF antagonist is a VEGF trap (e.g., aflibercept). In some embodiments, the VEGF antagonist is a tyrosine kinase inhibitor (e.g., pazopanib, axitinib, sorafenib, or sunitinib). In some embodiments, the VEGF antagonist is an anti-VEGF antibody. In some embodiments, the VEGF antibody is bevacizumab. One exemplary dosage of bevacizumab is in the range from about 0.05 mg/kg to about 20 mg/kg. Thus, one or more doses of about 0.5 mg/kg, 2.0 mg/kg, 4.0 mg/kg, 7.5 mg/kg, 10 mg/kg or 15 mg/kg (or any combination thereof) may be administered to the patient. Such doses may be administered intermittently, e.g., every week, every two, or every three weeks.

In some embodiments, the FGFR1 ECD and/or FGFR1 ECD fusion molecule (e.g., FGFR1-ECD.339-Fc) is administered in combination with another therapeutic agent, such as chemotherapeutic agent or anti-angiogenic agent, at the recommended or prescribed dosage and/or frequency of the therapeutic agent.

In some embodiments, an additional therapeutic agent is administered at a dosage approved by an agency responsible for approving therapeutic treatments, such as the Food and Drug Administration, or at the manufacturer's recommended dosage.

Routes of Administration and Carriers

In some embodiments, an FGFR1 ECD and/or FGFR1 ECD fusion molecule can be administered intravenously and/or subcutaneously. In some embodiments, an FGFR1 ECD and/or FGFR1 ECD fusion molecule can be administered by another route, such as intra-arterial, parenteral, intranasal, intramuscular, intracardiac, intraventricular, intratracheal, buccal, rectal, intraperitoneal, intradermal, topical, transdermal, or intrathecal, or otherwise by implantation or inhalation. In various embodiments, at least one additional therapeutic agent can be administered in vivo by a variety of routes, including intravenous, intra-arterial, subcutaneous, parenteral, intranasal, intramuscular, intracardiac, intraventricular, intratracheal, buccal, rectal, intraperitoneal, intradermal, topical, transdermal, and intrathecal, or otherwise by implantation or inhalation. Each of the subject compositions can be formulated alone or in combination into preparations in solid, semi-solid, liquid, or gaseous forms, such as tablets, capsules, powders, granules, ointments, solutions, suppositories, enemas, injections, inhalants, and aerosols.

In various embodiments, compositions comprising an FGFR1 ECD, FGFR1 ECD fusion molecule, and/or at least one additional therapeutic agent are provided in formulation with pharmaceutically acceptable carriers, a wide variety of which are known in the art (see, e.g., Gennaro, *Remington: The Science and Practice of Pharmacy with Facts and Comparisons: Drugfacts Plus,* 20th ed. (2003); Ansel et al., *Pharmaceutical Dosage Forms and Drug Delivery Systems,* 7*th* ed., Lippencott Williams and Wilkins (2004); Kibbe et al., *Handbook of Pharmaceutical Excipients,* 3*rd* ed., Pharmaceutical Press (2000)). Various pharmaceutically acceptable carriers, which include vehicles, adjuvants, carriers, and diluents, are available to the public. Moreover, various pharmaceutically acceptable auxiliary substances, such as pH adjusting and buffering agents, tonicity adjusting agents, stabilizers, wetting agents and the like, are also available to the public. Certain non-limiting exemplary carriers include saline, buffered saline, dextrose, water, glycerol, ethanol, and combinations thereof. In some embodiments, a therapeutic agent is formulated as the brand-name drug indicated above in the Definitions section, or a generic equivalent. In some embodiments, docetaxel is formulated as Taxotere® (Sanofi Aventis) or a generic equivalent.

In various embodiments, compositions comprising FGFR1 ECDs, FGFR1 ECD fusion molecules, and/or at least one additional therapeutic agent can be formulated for injection by dissolving, suspending, or emulsifying them in an aqueous or nonaqueous solvent, such as vegetable or other oils, synthetic aliphatic acid glycerides, esters of higher aliphatic acids, or propylene glycol; and if desired, with conventional additives such as solubilizers, isotonic agents, suspending agents, emulsifying agents, stabilizers and preservatives. In various embodiments, the compositions may be formulated for inhalation, for example, using pressurized acceptable propellants such as dichlorodifluoromethane, propane, nitrogen, and the like. The compositions may also be formulated, in various embodiments, into sustained release microcapsules, such as with biodegradable or non-biodegradable polymers. A non-limiting exemplary biodegradable formulation includes poly lactic acid-glycolic acid polymer. A non-limiting exemplary non-biodegradable formulation includes a polyglycerin fatty acid ester. Certain methods of making such formulations are described, for example, in EP 1 125 584 A1.

Pharmaceutical dosage packs comprising one or more containers, each containing one or more doses of an FGFR1 ECD, an FGFR1 ECD fusion molecule, and/or at least one additional therapeutic agent are also provided. In certain embodiments, a unit dosage is provided wherein the unit dosage contains a predetermined amount of a composition comprising an FGFR1 ECD, an FGFR1 ECD fusion molecule, and/or at least one additional therapeutic agent with or without one or more additional agents. In certain embodiments, such a unit dosage is supplied in single-use prefilled syringe for injection. In various embodiments, the composition contained in the unit dosage may comprise saline, sucrose, or the like; a buffer, such as phosphate, or the like; and/or be formulated within a stable and effective pH range. Alternatively, in certain embodiments, the composition may be provided as a lyophilized powder that can be reconstituted upon addition of an appropriate liquid, for example, sterile water. In certain embodiments, a composition comprises one or more substances that inhibit protein aggregation, including, but not limited to, sucrose and arginine. In certain embodiments, a composition of the invention comprises heparin and/or a proteoglycan.

In some embodiments, a dosage pack comprises instructions to determine whether a cancer has a higher level of FGF2 compared to the level of VEGF, and/or instructions to determine whether the cancer has a lower level of FGF2 compared to the level of VEGF prior to administering an FGFR1 ECD and/or an FGFR1 ECD fusion molecule, and/or at least one anti-angiogenic agent, as appropriate. In some such embodiments, the instructions indicate that a higher level of FGF2 compared to the level of VEGF is indicative of therapeutic responsiveness to an FGFR1 ECD and/or an FGFR1 ECD fusion molecule.

The term "instructions," as used herein includes, but is not limited to, labels, package inserts, instructions available in electronic form such as on a computer readable medium (e.g., a diskette, compact disk, or DVD), instructions available remotely such as over the internet, etc. A dosage pack is considered to include the instructions when the dosage pack provides access to the instructions, a link to the instructions (such as a uniform resource locator, or url), or other mechanism for obtaining a copy of the instructions (such as a return reply card, a physical address from which instructions may be requested, an e-mail address from which instructions may be requested, a phone number that may be called to obtain instructions, etc.).

FGFR1 ECDs and FGFR1 ECD Fusion Molecules

Nonlimiting exemplary FGFR1 ECDs include full-length FGFR1 ECDs, FGFR1 ECD fragments, and FGFR1 ECD variants. FGFR1 ECDs may include or lack a signal peptide. Exemplary FGFR1 ECDs include, but are not limited to, FGFR1 ECDs having amino acid sequences selected from SEQ ID NOs.: 1, 2, 3, and 4.

Non-limiting exemplary FGFR1 ECD fragments include human FGFR1 ECD ending at amino acid 339 (counting from the first amino acid of the mature form, without the signal peptide). In some embodiments, an FGFR1 ECD fragment ends at an amino acid between amino acid 339 and amino acid 360 (counting from the first amino acid of the mature form, without the signal peptide). Exemplary FGFR1 ECD fragments include, but are not limited to, FGFR1 ECD fragments having amino acid sequences selected from SEQ ID NOs.: 3 and 4.

In some embodiments, an FGFR1 ECD comprises a sequence selected from SEQ ID NOs: 1 to 4. In some embodiments, an FGFR1 ECD consists of a sequence selected from SEQ ID NOs: 1 to 4. When an FGFR1 ECD "consists of" a sequence selected from SEQ ID NOs: 1 to 4, the FGFR1 ECD may or may not contain various post-translational modifications, such as glycosylation and sialylation. In other words, when an FGFR1 ECD consists of a particular amino acid sequence, it does not contain additional amino acids in the contiguous amino acid sequence, but may contain modifications to amino acid side chains, the N-terminal amino group, and/or the C-terminal carboxy group.

In some embodiments, an FGFR1 ECD fusion molecule comprises a signal peptide. In some embodiments, an FGFR1 ECD fusion molecule lacks a signal peptide. In some embodiments, the FGFR1 ECD portion of an FGFR1 ECD fusion molecule comprises a sequence selected from SEQ ID NOs: 1 to 4. In some embodiments, the FGFR1 ECD portion of an FGFR1 ECD fusion molecule consists of a sequence selected from SEQ ID NOs: 1 to 4. When an FGFR1 ECD portion of an FGFR1 ECD fusion molecule "consists of" a sequence selected from SEQ ID NOs: 1 to 4, the FGFR1 ECD portion of an FGFR1 ECD fusion molecule may or may not contain various post-translational modifications, such as glycosylation and sialylation. In other words, when an FGFR1 ECD portion of an FGFR1 ECD fusion molecule consists of a particular amino acid sequence, it does not contain additional amino acids from FGFR1 in the contiguous amino acid sequence, but may contain modifications to amino acid side chains, the N-terminal amino group, and/or the C-terminal carboxy group. Further, because the FGFR1 ECD is linked to a fusion molecule, there may be additional amino acids at the N- and/or C-terminus of the FGFR1 ECD, but those amino acids are not from the FGFR1 sequence, but may be from, for example, a linker sequence, or a fusion partner sequence.

In some embodiments, the fusion partner portion of an FGFR1 ECD fusion molecule is selected from Fc, albumin, and polyethylene glycol. Nonlimiting exemplary fusion partners are discussed herein.

The inventors have found that administration of an FGFR1 ECD and/or an FGFR1 ECD fusion molecule and at least one anti-angiogenic agent is more effective in cancers in which at least a portion of the cancer cells have a lower level of FGF2 compared to the level of VEGF than treatment with an anti-angiogenic agent alone. The inventors have further found that administration of an FGFR1 ECD and/or an FGFR1 ECD fusion molecule is effective in cancers in which at least a portion of the cancer cells have a higher level of FGF2 compared to the level of VEGF. In some embodiments, administration of an FGFR1 ECD and/or an FGFR1 ECD fusion molecule is effective in such cancers as a monotherapy.

Cancers with a higher level of FGF2 compared to the level of VEGF may, in some embodiments, have elevated levels of both FGF2 and VEGF compared to a reference sample, cell, or tissue, although the level of FGF2 is higher than the level of VEGF. Cancers with a lower level of FGF2 compared to the level of VEGF may, in some embodiments, have elevated levels of both FGF2 and VEGF compared to a reference sample, cell, or tissue, although the level of FGF2 is lower than the level of VEGF.

In some embodiments, in a cancer with a higher level of FGF2 compared to the level of VEGF, the level of FGF2 may be higher or lower than the FGF2 level in a reference cell and the level of VEGF may be higher or lower than the VEGF level in a reference cell, so long as the level of FGF2 is higher than the level of VEGF. Similarly, in some embodiments, in a cancer with a lower level of FGF2 compared to the level of VEGF, the level of FGF2 may be higher or lower than the FGF2 level in a reference cell and the level of VEGF may be higher or lower than the VEGF level in a reference cell, so long as the level of FGF2 is lower than the level of VEGF.

Fusion Partners and Conjugates

As discussed herein, an FGFR1 ECD may be combined with at least one fusion partner, resulting in an FGFR1 ECD fusion molecule. These fusion partners may facilitate purification, and the FGFR1 ECD fusion molecules may show an increased half-life in vivo. Suitable fusion partners of an FGFR1 ECD include, for example, polymers, such as water soluble polymers, the constant domain of immunoglobulins; all or part of human serum albumin (HSA); fetuin A; fetuin B; a leucine zipper domain; a tetranectin trimerization domain; mannose binding protein (also known as mannose binding lectin), for example, mannose binding protein 1; and an Fc region, as described herein and further described in U.S. Pat. No. 6,686,179. Nonlimiting exemplary FGFR1 ECD fusion molecules are described, e.g., in U.S. Pat. No. 7,678,890.

An FGFR1 ECD fusion molecule may be prepared by attaching polyaminoacids or branch point amino acids to the FGFR1 ECD. For example, the polyaminoacid may be a carrier protein that serves to increase the circulation half life of the FGFR1 ECD (in addition to the advantages achieved via a fusion molecule). For the therapeutic purpose of the present invention, such polyaminoacids should ideally be those that have or do not create neutralizing antigenic responses, or other adverse responses. Such polyaminoacids may be chosen from serum albumin (such as HSA), an additional antibody or portion thereof, for example the Fc region, fetuin A, fetuin B, leucine zipper nuclear factor erythroid derivative-2 (NFE2), neuroretinal leucine zipper, tetranectin, or other polyaminoacids, for example, lysines. As described herein, the location of attachment of the polyaminoacid may be at the N terminus or C terminus, or other places in between, and also may be connected by a chemical linker moiety to the selected molecule.

Polymers

Polymers, for example, water soluble polymers, may be useful as fusion partners to reduce precipitation of the FGFR1 ECD fusion molecule in an aqueous environment, such as typically found in a physiological environment. Polymers employed in the invention will be pharmaceutically acceptable for the preparation of a therapeutic product or composition.

Suitable, clinically acceptable, water soluble polymers include, but are not limited to, polyethylene glycol (PEG), polyethylene glycol propionaldehyde, copolymers of ethylene glycol/propylene glycol, monomethoxy-polyethylene glycol, carboxymethylcellulose, dextran, polyvinyl alcohol (PVA), polyvinyl pyrrolidone, poly-1,3-dioxolane, poly-1,3,6-trioxane, ethylene/maleic anhydride copolymer, poly (β-amino acids) (either homopolymers or random copolymers), poly(n-vinyl pyrrolidone) polyethylene glycol, polypropylene glycol homopolymers (PPG) and other polyakylene oxides, polypropylene oxide/ethylene oxide copolymers, polyoxyethylated polyols (POG) (e.g., glycerol) and other polyoxyethylated polyols, polyoxyethylated sorbitol, or polyoxyethylated glucose, colonic acids or other carbohydrate polymers, Ficoll, or dextran and mixtures thereof.

As used herein, polyethylene glycol (PEG) is meant to encompass any of the forms that have been used to derivative other proteins, such as mono-($C_1$-$C_{10}$) alkoxy- or aryloxy-polyethylene glycol. Polyethylene glycol propionaldehyde may have advantages in manufacturing due to its stability in water.

Polymers used herein, for example water soluble polymers, may be of any molecular weight and may be branched or unbranched. In some embodiments, the polymers have an average molecular weight of between about 2 kDa to about 100 kDa (the term "about" indicating that in preparations of a polymer, some molecules will weigh more, some less, than the stated molecular weight). The average molecular weight of each polymer may be between about 5 kDa and about 50 kDa, or between about 12 kDa and about 25 kDa. Generally, the higher the molecular weight or the more branches, the higher the polymer:protein ratio. Other sizes may also be used, depending on the desired therapeutic profile; for example, the duration of sustained release; the effects, if any, on biological activity; the ease in handling; the degree or lack of antigenicity; and other known effects of a polymer on an FGFR1 ECD.

Polymers employed in the present invention are typically attached to an FGFR1 ECD with consideration of effects on functional or antigenic domains of the polypeptide. In general, chemical derivatization may be performed under any suitable condition used to react a protein with an activated polymer molecule. Activating groups which can be used to link the polymer to the active moieties include sulfone, maleimide, sulfhydryl, thiol, triflate, tresylate, azidirine, oxirane, and 5-pyridyl.

Polymers of the invention are typically attached to a heterologous polypeptide at the alpha (α) or epsilon (ε) amino groups of amino acids or a reactive thiol group, but it is also contemplated that a polymer group could be attached to any reactive group of the protein that is sufficiently reactive to become attached to a polymer group under suitable reaction conditions. Thus, a polymer may be covalently bound to an FGFR1 ECD via a reactive group, such as a free amino or carboxyl group. The amino acid residues having a free amino group may include lysine residues and the N-terminal amino acid residue. Those having a free carboxyl group may include aspartic acid residues, glutamic acid residues, and the C-terminal amino acid residue. Those having a reactive thiol group include cysteine residues.

Methods for preparing fusion molecules conjugated with polymers, such as water soluble polymers, will each generally involve (a) reacting an FGFR1 ECD with a polymer under conditions whereby the polypeptide becomes attached to one or more polymers and (b) obtaining the reaction product. Reaction conditions for each conjugation may be selected from any of those known in the art or those subsequently developed, but should be selected to avoid or limit exposure to reaction conditions such as temperatures, solvents, and pH levels that would inactivate the protein to be modified. In general, the optimal reaction conditions for the reactions will be determined case-by-case based on known parameters and the desired result. For example, the larger the ratio of polymer:polypeptide conjugate, the greater the percentage of conjugated product. The optimum ratio (in terms of efficiency of reaction in that there is no excess unreacted polypeptide or polymer) may be determined by factors such as the desired degree of derivatization (e.g., mono-, di-, tri-, etc.), the molecular weight of the polymer selected, whether the polymer is branched or unbranched and the reaction conditions used. The ratio of polymer (for example, PEG) to a polypeptide will generally range from 1:1 to 100:1. One or more purified conjugates may be prepared from each mixture by standard purification techniques, including among others, dialysis, salting-out, ultrafiltration, ion-exchange chromatography, gel filtration chromatography, and electrophoresis.

One may specifically desire an N-terminal chemically modified FGFR1 ECD. One may select a polymer by molecular weight, branching, etc., the proportion of polymers to FGFR1 ECD molecules in the reaction mix, the type of reaction to be performed, and the method of obtaining the selected N-terminal chemically modified FGFR1 ECD. The method of obtaining the N-terminal chemically modified FGFR1 ECD preparation (separating this moiety from other monoderivatized moieties if necessary) may be by purification of the N-terminal chemically modified FGFR1 ECD material from a population of chemically modified protein molecules.

Selective N-terminal chemical modification may be accomplished by reductive alkylation which exploits differential reactivity of different types of primary amino groups (lysine versus the N-terminal) available for derivatization in a particular protein. Under the appropriate reaction conditions, substantially selective derivatization of the protein at the N terminus with a carbonyl group-containing polymer is achieved. For example, one may selectively attach a polymer to the N terminus of the protein by performing the reaction at a pH that allows one to take advantage of the pKa differences between the ε-amino group of the lysine residues and that of the α-amino group of the N-terminal residue of the protein. By such selective derivatization, attachment of a polymer to a protein is controlled: the conjugation with the polymer takes place predominantly at the N terminus of the protein and no significant modification of other reactive groups, such as the lysine side chain amino groups, occurs. Using reductive alkylation, the polymer may be of the type described above and should have a single reactive aldehyde for coupling to the protein. Polyethylene glycol propionaldehyde, containing a single reactive aldehyde, may also be used.

In one embodiment, the present invention contemplates the chemically derivatized FGFR1 ECD to include mono- or poly- (e.g., 2-4) PEG moieties. Pegylation may be carried out by any of the pegylation reactions available. Methods for preparing a pegylated protein product will generally include (a) reacting a polypeptide with polyethylene glycol (such as a reactive ester or aldehyde derivative of PEG) under conditions whereby the protein becomes attached to one or more PEG groups; and (b) obtaining the reaction product(s). In general, the optimal reaction conditions will be determined case by case based on known parameters and the desired result.

There are a number of PEG attachment methods known in the art. See, for example, EP 0 401 384; Malik et al., *Exp. Hematol.*, 20:1028-1035 (1992); Francis, *Focus on Growth Factors*, 3(2):4-10 (1992); EP 0 154 316; EP 0 401 384; WO 92/16221; WO 95/34326; and the other publications cited herein that relate to pegylation.

Pegylation may be carried out, e.g., via an acylation reaction or an alkylation reaction with a reactive polyethylene glycol molecule. Thus, protein products according to the present invention include pegylated proteins wherein the PEG group(s) is (are) attached via acyl or alkyl groups. Such products may be mono-pegylated or poly-pegylated (for example, those containing 2-6 or 2-5 PEG groups). The PEG groups are generally attached to the protein at the α- or ε-amino groups of amino acids, but it is also contemplated that the PEG groups could be attached to any amino group attached to the protein that is sufficiently reactive to become attached to a PEG group under suitable reaction conditions.

Pegylation by acylation generally involves reacting an active ester derivative of polyethylene glycol (PEG) with an FGFR1 ECD. For acylation reactions, the polymer(s) selected typically have a single reactive ester group. Any known or subsequently discovered reactive PEG molecule may be used to carry out the pegylation reaction. An example of a suitable activated PEG ester is PEG esterified to N-hydroxysuccinimide (NHS). As used herein, acylation is contemplated to include, without limitation, the following types of linkages between the therapeutic protein and a polymer such as PEG: amide, carbamate, urethane, and the like, see for example, Chamow, *Bioconjugate Chem.*, 5:133-140 (1994). Reaction conditions may be selected from any of those currently known or those subsequently developed, but should avoid conditions such as temperature, solvent, and pH that would inactivate the polypeptide to be modified.

Pegylation by acylation will generally result in a poly-pegylated protein. The connecting linkage may be an amide. The resulting product may be substantially only (e.g., >95%) mono-, di-, or tri-pegylated. However, some species with higher degrees of pegylation may be formed in amounts depending on the specific reaction conditions used. If desired, more purified pegylated species may be separated from the mixture (particularly unreacted species) by standard purification techniques, including among others, dialysis, salting-out, ultrafiltration, ion-exchange chromatography, gel filtration chromatography, and electrophoresis.

Pegylation by alkylation generally involves reacting a terminal aldehyde derivative of PEG with a polypeptide in the presence of a reducing agent. For the reductive alkylation reaction, the polymer(s) selected should have a single reactive aldehyde group. An exemplary reactive PEG aldehyde is polyethylene glycol propionaldehyde, which is water stable, or mono $C_1$-$C_{10}$ alkoxy or aryloxy derivatives thereof, see for example, U.S. Pat. No. 5,252,714.

Markers

Moreover, FGFR1 ECDs of the present invention may be fused to marker sequences, such as a peptide that facilitates purification of the fused polypeptide. The marker amino acid sequence may be a hexa-histidine peptide such as the tag provided in a pQE vector (Qiagen, Mississauga, Ontario, Canada), among others, many of which are commercially available. As described in Gentz et al., *Proc. Natl. Acad. Sci.* 86:821-824 (1989), for instance, hexa-histidine provides for convenient purification of the fusion protein. Another peptide tag useful for purification, the hemagglutinin (HA) tag, corresponds to an epitope derived from the influenza HA protein. (Wilson et al., *Cell* 37:767 (1984)). Any of these above fusions may be engineered using the FGFR1 ECDs described herein.

Oligomerization Domain Fusion Partners

In various embodiments, oligomerization offers some functional advantages to a fusion protein, including, but not limited to, multivalency, increased binding strength, and the combined function of different domains. Accordingly, in some embodiments, a fusion partner comprises an oligomerization domain, for example, a dimerization domain. Exemplary oligomerization domains include, but are not limited to, coiled-coil domains, including alpha-helical coiled-coil domains; collagen domains; collagen-like domains; and certain immunoglobulin domains. Exemplary coiled-coil polypeptide fusion partners include, but are not limited to, the tetranectin coiled-coil domain; the coiled-coil domain of cartilage oligomeric matrix protein; angiopoietin coiled-coil domains; and leucine zipper domains. Exemplary collagen or collagen-like oligomerization domains include, but are not limited to, those found in collagens, mannose binding lectin, lung surfactant proteins A and D, adiponectin, ficolin, conglutinin, macrophage scavenger receptor, and emilin.

Antibody Fc Immunoglobulin Domain Fusion Partners

Many Fc domains that may be used as fusion partners are known in the art. In some embodiments, a fusion partner is an Fc immunoglobulin domain. An Fc fusion partner may be a wild-type Fc found in a naturally occurring antibody, a variant thereof, or a fragment thereof. Non-limiting exemplary Fc fusion partners include Fcs comprising a hinge and the CH2 and CH3 constant domains of a human IgG, for example, human IgG1, IgG2, IgG3, or IgG4. Additional exemplary Fc fusion partners include, but are not limited to, human IgA and IgM. In some embodiments, an Fc fusion partner comprises a C237S mutation, for example, in an IgG1 (see, for example, SEQ ID NO: 8). In some embodiments, an Fc fusion partner comprises a hinge, CH2, and CH3 domains of human IgG2 with a P331S mutation, as described in U.S. Pat. No. 6,900,292. Certain exemplary Fc domain fusion partners are shown in SEQ ID NOs: 8 to 10.

Albumin Fusion Partners and Albumin-Binding Molecule Fusion Partners

In some embodiments, a fusion partner is an albumin. Exemplary albumins include, but are not limited to, human serum album (HSA) and fragments of HSA that are capable of increasing the serum half-life or bioavailability of the polypeptide to which they are fused. In some embodiments, a fusion partner is an albumin-binding molecule, such as, for example, a peptide that binds albumin or a molecule that conjugates with a lipid or other molecule that binds albumin. In some embodiments, a fusion molecule comprising HSA is prepared as described, e.g., in U.S. Pat. No. 6,686,179.

Exemplary Attachment of Fusion Partners

The fusion partner may be attached, either covalently or non-covalently, to the N terminus or the C terminus of the FGFR1 ECD. The attachment may also occur at a location within the FGFR1 ECD other than the N terminus or the C terminus, for example, through an amino acid side chain (such as, for example, the side chain of cysteine, lysine, serine, or threonine).

In either covalent or non-covalent attachment embodiments, a linker may be included between the fusion partner and the FGFR1 ECD. Such linkers may be comprised of at least one amino acid or chemical moiety. Exemplary methods of covalently attaching a fusion partner to an FGFR1 ECD include, but are not limited to, translation of the fusion partner and the FGFR1 ECD as a single amino acid sequence and chemical attachment of the fusion partner to the FGFR1 ECD. When the fusion partner and an FGFR1 ECD are translated as single amino acid sequence, additional amino acids may be included between the fusion partner and the FGFR1 ECD as a linker. In some embodiments, the linker is selected based on the polynucleotide sequence that encodes it, to facilitate cloning the fusion partner and/or FGFR1 ECD into a single expression construct (for example, a polynucleotide containing a particular restriction site may be placed between the polynucleotide encoding the fusion partner and the polynucleotide encoding the FGFR1 ECD, wherein the polynucleotide containing the restriction site encodes a short amino acid linker sequence). When the fusion partner and the FGFR1 ECD are covalently coupled by chemical means, linkers of various sizes may typically be included during the coupling reaction.

Exemplary methods of non-covalently attaching a fusion partner to an FGFR1 ECD include, but are not limited to, attachment through a binding pair. Exemplary binding pairs include, but are not limited to, biotin and avidin or streptavidin, an antibody and its antigen, etc.

Co-Translational and Post-Translational Modifications

The invention encompasses administration of FGFR1 ECDs and FGFR1 ECD fusion molecules that are differentially modified during or after translation, for example by glycosylation, acetylation, phosphorylation, amidation, derivatization by known protecting/blocking groups, proteolytic cleavage, or linkage to an antibody molecule or other cellular ligand. Any of numerous chemical modifications may be carried out by known techniques, including, but not limited to, specific chemical cleavage by cyanogen bromide, trypsin, chymotrypsin, papain, V8 protease; $NABH_4$; acetylation; formylation; oxidation; reduction; and/or metabolic synthesis in the presence of tunicamycin.

Additional post-translational modifications encompassed by the invention include, for example, for example, N-linked or O-linked carbohydrate chains, processing of N-terminal or C-terminal ends), attachment of chemical moieties to the amino acid backbone, chemical modifications of N-linked or O-linked carbohydrate chains, and addition or deletion of an N-terminal methionine residue as a result of prokaryotic host cell expression. A nonlimiting discussion of various post-translational modifications of FGFR1 ECDs and FGFR1 ECD fusion molecules can be found, e.g., in U.S. Pat. No. 7,678,890.

FGFR1 ECD and FGFR1 ECD Fusion Molecule Expression and Production Vectors

Vectors comprising polynucleotides that encode FGFR1 ECDs are provided. Vectors comprising polynucleotides that encode FGFR1 ECD fusion molecules are also provided. Such vectors include, but are not limited to, DNA vectors, phage vectors, viral vectors, retroviral vectors, etc.

In some embodiments, a vector is selected that is optimized for expression of polypeptides in CHO or CHO-derived cells. Exemplary such vectors are described, e.g., in Running Deer et al., *Biotechnol. Prog.* 20:880-889 (2004).

In some embodiments, a vector is chosen for in vivo expression of FGFR1 ECDs and/or FGFR1 ECD fusion molecules in animals, including humans. In some such embodiments, expression of the polypeptide is under the control of a promoter that functions in a tissue-specific manner. For example, liver-specific promoters are described, e.g., in PCT Publication No. WO 2006/076288. A nonlimiting discussion of various expression vectors can be found, e.g., in U.S. Pat. No. 7,678,890.

Host Cells

In various embodiments, FGFR1 ECDs or FGFR1 ECD fusion molecules may be expressed in prokaryotic cells, such as bacterial cells; or in eukaryotic cells, such as fungal cells, plant cells, insect cells, and mammalian cells. Such expression may be carried out, for example, according to procedures known in the art. Exemplary eukaryotic cells that may be used to express polypeptides include, but are not limited to, COS cells, including COS 7 cells; 293 cells, including 293-6E cells; CHO cells, including CHO-S and DG44 cells; and NSO cells. In some embodiments, a particular eukaryotic host cell is selected based on its ability to make certain desired post-translational modifications to the FGFR1 ECDs or FGFR1 ECD fusion molecules. For example, in some embodiments, CHO cells produce FGFR1 ECDs and/or FGFR1 ECD fusion molecules that have a higher level of sialylation than the same polypeptide produced in 293 cells.

Introduction of a nucleic acid into a desired host cell may be accomplished by any method known in the art, including but not limited to, calcium phosphate transfection, DEAE-dextran mediated transfection, cationic lipid-mediated transfection, electroporation, transduction, infection, etc. Non-limiting exemplary methods are described, e.g., in Sambrook et al., *Molecular Cloning, A Laboratory Manual*, $3^{rd}$ ed. Cold Spring Harbor Laboratory Press (2001). Nucleic acids may be transiently or stably transfected in the desired host cells, according to methods known in the art. A nonlimiting discussion of host cells and methods of polypeptides in host cells can be found, e.g., in U.S. Pat. No. 7,678,890.

In some embodiments, a polypeptide may be produced in vivo in an animal that has been engineered or transfected with a nucleic acid molecule encoding the polypeptide, according to methods known in the art.

Purification of FGFR1 ECD Polypeptides

FGFR1 ECDs or FGFR1 ECD fusion molecules may be purified by various methods known in the art. Such methods include, but are not limited to, the use of affinity matrices or hydrophobic interaction chromatography. Suitable affinity ligands include any ligands of the FGFR1 ECD or of the fusion partner. Suitable affinity ligands in the case of an antibody that binds FGFR1 include, but are not limited to, FGFR1 itself and fragments thereof. Further, a Protein A, Protein G, Protein A/G, or an antibody affinity column may be used to bind to an Fc fusion partner to purify an FGFR1 ECD fusion molecule. Antibodies to FGFR1 ECD may also be used to purify FGFR1 ECD or FGFR1 ECD fusion molecules. Hydrophobic interactive chromatography, for example, a butyl or phenyl column, may also suitable for purifying some polypeptides. Many methods of purifying polypeptides are known in the art. A nonlimiting discussion of various methods of purifying polypeptides can be found, e.g., in U.S. Pat. No. 7,678,890.

Methods of Identifying Patients Who would Benefit from FGFR1 ECDs and/or FGFR1 ECD Fusion Molecules In some embodiments, methods of identifying patients with cancer who may benefit from administration of an FGFR1 ECD or FGFR1 ECD fusion molecule are provided. In some such embodiments, the method comprises determining whether at least a portion of the cancer cells comprise a higher level of FGF2 compared to the level of VEGF in a sample obtained from the subject. In some embodiments, at least 10%, at least 20%, at least 30%, at least 40%, at least 50%, at least 60%, at least 70%, at least 80%, or at least 90% of the cells of a cancer sample are determined to have a higher level of FGF2 mRNA or protein compared to the level of VEGF mRNA or protein. In some embodiments, a higher level of FGF2 compared to the level of VEGF is indicative of therapeutic responsiveness by the cancer to an FGFR1 ECD or FGFR1 ECD fusion molecule. In some embodiments, a sample is taken from a patient having or suspected of having cancer. A finding of a higher level of FGF2 compared to the level of VEGF in at least a portion of the cancer cells indicates that the patient having or suspected of having cancer may benefit from an FGFR1 ECD or FGFR1 ECD fusion molecule therapy. In some embodiments, the patient has or is suspected of having kidney cancer, liver cancer, glioblastoma, or mesothelioma.

In some embodiments, methods of identifying patients with cancer who may benefit from administration of an FGFR1 ECD or FGFR1 ECD fusion molecule and at least one anti-angiogenic agent are provided. In some such embodiments, the method comprises determining whether at least a portion of the cancer cells comprise a lower level of FGF2 compared to the level of VEGF in a sample obtained from the subject. In some embodiments, at least 10%, at least 20%, at least 30%, at least 40%, at least 50%, at least 60%, at least 70%, at least 80%, or at least 90% of the cells of a cancer sample are determined to have a lower level of FGF2 mRNA or protein compared to the level of VEGF mRNA or protein. In some embodiments, a sample is taken from a patient having or suspected of having cancer. A finding of a lower level of FGF2 compared to the level of VEGF in at least a portion of the cancer cells indicates that the patient having or suspected of having cancer may benefit from an FGFR1 ECD or FGFR1 ECD fusion molecule and at least one anti-angiogenic agent therapy. In some embodiments, the patient has or is suspected of having kidney cancer, liver cancer, glioblastoma, or mesothelioma.

In some embodiments, the level of FGF2 and/or the level of VEGF is determined by a laboratory. A laboratory may be a hospital laboratory or a laboratory independent of a hospital. In some embodiments, following a determination of the level of FGF2 and/or the level of VEGF, the results of the determination are communicated to a medical professional. In some embodiments, the level of FGF2 is compared to the level of VEGF and the results of the comparison are communicated to the medical professional (such as, for example, "FGF2 higher than VEGF", "FGF2 lower than VEGF", "FGF2/VEGF>1", "FGF2/VEGF<1", etc.) In some embodiments, the results are communicated for the purpose of determining whether a patient should benefit from, or be responsive to, an FGFR1 ECD or FGFR1 ECD fusion molecule therapy. In some embodiments, the results are communicated for the purpose of determining whether a patient should benefit from, or be responsive to, an FGFR1 ECD or FGFR1 ECD fusion molecule and at least one anti-angiogenic agent therapy. In some embodiments, medical professionals include, but are not limited to, doctors, nurses, hospital administration and staff, etc.

Any suitable method of determining protein levels may be used. In certain embodiments, the level of proteins in a sample is examined using immunohistochemistry ("IHC") and staining protocols. Immunohistochemical staining of tissue sections has been shown to be a reliable method of assessing or detecting presence of proteins in a sample. Immunohistochemistry techniques utilize an antibody to probe and visualize cellular antigens in situ, generally by chromogenic or fluorescent methods.

The tissue sample may be fixed (i.e. preserved) by conventional methodology (See e.g., "Manual of Histological Staining Method of the Armed Forces Institute of Pathology," 3$^{rd}$ edition (1960) Lee G. Luna, HT (ASCP) Editor, The Blakston Division McGraw-Hill Book Company, New York; The Armed Forces Institute of Pathology Advanced Laboratory Methods in Histology and Pathology (1994) Ulreka V. Mikel, Editor, Armed Forces Institute of Pathology, American Registry of Pathology, Washington, D.C.). One of skill in the art will appreciate that the choice of a fixative is determined by the purpose for which the sample is to be histologically stained or otherwise analyzed. One of skill in the art will also appreciate that the length of fixation depends upon the size of the tissue sample and the fixative used. By way of example, neutral buffered formalin, Bouin's or paraformaldehyde, may be used to fix a sample.

Generally, the sample is first fixed and is then dehydrated through an ascending series of alcohols, infiltrated and embedded with paraffin or other sectioning media so that the tissue sample may be sectioned. Alternatively, one may section the tissue and fix the sections obtained. By way of example, the tissue sample may be embedded and processed in paraffin by conventional methodology (See e.g., "Manual of Histological Staining Method of the Armed Forces Institute of Pathology", supra). Examples of paraffin that may be used include, but are not limited to, Paraplast, Broloid, and Tissuemay. Once the tissue sample is embedded, the sample may be sectioned by a microtome or the like (See e.g., "Manual of Histological Staining Method of the Armed Forces Institute of Pathology", supra). By way of example for this procedure, sections may range from about three microns to about five microns in thickness. Once sectioned, the sections may be attached to slides by several standard methods. Examples of slide adhesives include, but are not limited to, silane, gelatin, poly-L-lysine and the like. By way of example, the paraffin embedded sections may be attached to positively charged slides and/or slides coated with poly-L-lysine.

If paraffin has been used as the embedding material, the tissue sections are generally deparaffinized and rehydrated to water. The tissue sections may be deparaffinized by several conventional standard methodologies. For example, xylenes and a gradually descending series of alcohols may be used (See e.g., "Manual of Histological Staining Method of the Armed Forces Institute of Pathology", supra). Alternatively, commercially available deparaffinizing non-organic agents such as Hemo-De7 (CMS, Houston, Tex.) may be used.

In some embodiments, subsequent to the sample preparation, a tissue section may be analyzed using IHC. IHC may be performed in combination with additional techniques such as morphological staining and/or fluorescence in-situ hybridization. Two general methods of IHC are available; direct and indirect assays. According to the first assay, binding of antibody to the target antigen is determined directly. This direct assay uses a labeled reagent, such as a fluorescent tag or an enzyme-labeled primary antibody, which can be visualized without further antibody interaction. In a typical indirect assay, unconjugated primary antibody binds to the antigen and then a labeled secondary antibody binds to the primary antibody. Where the secondary antibody is conjugated to an enzymatic label, a chromogenic or fluorogenic substrate is added to provide visualization of the antigen. Signal amplification occurs because several secondary antibodies may react with different epitopes on the primary antibody.

The primary and/or secondary antibody used for immunohistochemistry typically will be labeled with a detectable moiety. Numerous labels are available which can be generally grouped into the following categories: (a) Radioisotopes, such as $^{35}S$, $^{14}C$, $^{125}I$, $^{3}H$ and $^{131}I$. The antibody can be labeled with the radioisotope using the techniques described in Current Protocols in Immunology, Volumes 1 and 2, Coligen et al., Ed. Wiley-Interscience, New York, N.Y., Pubs. (1991) for example and radioactivity can be measured using scintillation counting. (b) Colloidal gold particles. (c) Fluorescent labels including, but are not limited to, rare earth chelates (europium chelates), Texas Red, rhodamine, fluorescein, dansyl, Lissamine, umbelliferone, phycoerytherin, phycocyanin, or commercially available fluorophores such SPECTRUM ORANGE7 and SPECTRUM GREEN7 and/or derivatives of any one or more of the above. The fluorescent labels can be conjugated to the antibody using the techniques disclosed in Current Protocols in Immunology, supra, for example. Fluorescence can be quantified using a fluorimeter. (d) Various enzyme-substrate labels are available and U.S. Pat. No. 4,275,149 provides a review of some of these. The enzyme generally catalyzes a chemical alteration of the chromogenic substrate that can be measured using various techniques. For example, the enzyme may catalyze a color change in a substrate, which can be measured spectrophotometrically. Alternatively, the enzyme may alter the fluorescence or chemiluminescence of the substrate. Techniques for quantifying a change in fluorescence are described above. The chemiluminescent substrate becomes electronically excited by a chemical reaction and may then emit light which can be measured (using a chemiluminometer, for example) or donates energy to a fluorescent acceptor. Examples of enzymatic labels include luciferases (e.g., firefly luciferase and bacterial luciferase; U.S. Pat. No. 4,737,456), luciferin, 2,3-dihydrophthalazinediones, malate dehydrogenase, urease, peroxidase such as horseradish peroxidase (HRPO), alkaline phosphatase, .beta.-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like. Techniques for conjugating enzymes to antibodies are described in O'Sullivan et al., Methods for the Preparation of Enzyme-Antibody Conjugates for use in Enzyme Immunoassay, in Methods in Enzym. (ed. J. Langone & H. Van Vunakis), Academic press, New York, 73:147-166 (1981).

Examples of enzyme-substrate combinations include, for example: (i) Horseradish peroxidase (HRPO) with hydrogen peroxidase as a substrate, wherein the hydrogen peroxidase oxidizes a dye precursor (e.g., orthophenylene diamine (OPD) or 3,3',5,5'-tetramethyl benzidine hydrochloride (TMB)); (ii) alkaline phosphatase (AP) with para-Nitrophenyl phosphate as chromogenic substrate; and (iii) .beta.-D-galactosidase (.beta.-D-Gal) with a chromogenic substrate (e.g., p-nitrophenyl-.beta.-D-galactosidase) or fluorogenic substrate (e.g., 4-methylumbelliferyl-.beta.-D-galactosidase).

Numerous other enzyme-substrate combinations are available to those skilled in the art. For a general review of these, see U.S. Pat. Nos. 4,275,149 and 4,318,980. Sometimes, the label is indirectly conjugated with the antibody. The skilled artisan will be aware of various techniques for achieving this. For example, the antibody can be conjugated with biotin and any of the four broad categories of labels mentioned above can be conjugated with avidin, or vice versa. Biotin binds selectively to avidin and thus, the label can be conjugated with the antibody in this indirect manner. Alternatively, to achieve indirect conjugation of the label with the antibody, the antibody is conjugated with a small hapten and one of the different types of labels mentioned above is conjugated with an anti-hapten antibody. Thus, indirect conjugation of the label with the antibody can be achieved.

Aside from the sample preparation procedures discussed above, further treatment of the tissue section prior to, during or following IHC may be desired. For example, epitope retrieval methods, such as heating the tissue sample in citrate buffer may be carried out (see, e.g., Leong et al. *Appl. Immunohistochem.* 4(3):201 (1996)).

Following an optional blocking step, the tissue section is exposed to primary antibody for a sufficient period of time and under suitable conditions such that the primary antibody binds to the target protein antigen in the tissue sample. Appropriate conditions for achieving this can be determined by routine experimentation. The extent of binding of antibody to the sample is determined by using any one of the detectable labels discussed above. In some embodiments, the label is an enzymatic label (e.g. HRPO) which catalyzes a chemical alteration of the chromogenic substrate such as 3,3'-diaminobenzidine chromogen. In one embodiment, the enzymatic label is conjugated to antibody which binds specifically to the primary antibody (e.g. the primary antibody is rabbit polyclonal antibody and secondary antibody is goat anti-rabbit antibody).

Specimens thus prepared may be mounted and coverslipped. Slide evaluation is then determined, e.g., using a microscope, and staining intensity criteria, routinely used in the art, may be employed.

In some embodiments, when IHC is used, a tiered system of staining is used to determine the level of FGF2 and/or VEGF in a cell or collection of cells. For example, in some embodiments, a four-tiered system is used in which the tiers are no staining, 1+, 2+, and 3+, where 1+, 2+, and 3+ indicate increasing levels of staining, respectively. In some embodiments, a higher level of FGF2 compared to VEGF is found where the FGF2 staining is at a higher tier than the VEGF staining. In some embodiments, a higher level of FGF2 compared to VEGF is found where the FGF2 staining and VEGF staining are at the same tier, but the histologist determines that a greater area of the tumor has FGF2 staining than VEGF staining. In some embodiments, a lower level of FGF2 compared to VEGF is found where the FGF2 staining is at a lower tier than the VEGF staining. In some embodiments, a lower level of FGF2 compared to VEGF is found where the FGF2 staining and VEGF staining are at the same tier, but the histologist determines that a greater area of the tumor has VEGF staining than FGF2 staining. One skilled in the art can determine the staining levels that indicate a higher or lower level of FGF2 compared to VEGF depending on the particular IHC assay (including the particular antibody), the cell type, etc.

Any suitable method of determining mRNA levels may be used. Methods for the evaluation of mRNAs in cells are well known and include, for example, hybridization assays using complementary DNA probes (such as in situ hybridization using labeled riboprobes specific for FGF2 or VEGF, Northern blot and related techniques) and various nucleic acid amplification assays (such as RT-PCR using complementary primers specific for FGF2 and/or VEGF and other amplification type detection methods, such as, for example, branched DNA, SISBA, TMA and the like).

Tissue or cell samples from mammals can be conveniently assayed for mRNAs using Northern, dot blot or PCR analysis. For example, RT-PCR assays such as quantitative PCR assays are well known in the art. In some embodiments, mRNA levels are levels quantified using real-time qRT-PCR. In some embodiments of the invention, a method for detecting a target mRNA in a biological sample comprises producing cDNA from the sample by reverse transcription using at least one primer; amplifying the cDNA so produced using a target polynucleotide as sense and antisense primers to amplify target cDNAs therein; and detecting the presence of the amplified target cDNA. In addition, such methods can include one or more steps that allow one to determine the levels of target mRNA in a biological sample (e.g., by simultaneously examining the levels a comparative control mRNA sequence of a "housekeeping" gene such as an actin family member). Optionally, the sequence of the amplified target cDNA can be determined.

Optional methods of the invention include protocols which examine or detect mRNAs, such as target mRNAs, in a tissue or cell sample by microarray technologies. Using nucleic acid microarrays, test and control mRNA samples from test and control tissue samples are reverse transcribed and labeled to generate cDNA probes. The probes are then hybridized to an array of nucleic acids immobilized on a solid support. The array is configured such that the sequence and position of each member of the array is known. Hybridization of a labeled probe with a particular array member indicates that the sample from which the probe was derived expresses that gene. Differential gene expression analysis of disease tissue can provide valuable information. Microarray technology utilizes nucleic acid hybridization techniques and computing technology to evaluate the mRNA expression profile of thousands of genes within a single experiment. (see, e.g., WO 01/75166 published Oct. 11, 2001; (see, for example, U.S. Pat. No. 5,700,637, U.S. Pat. No. 5,445,934, and U.S. Pat. No. 5,807,522, Lockart, Nature Biotechnology, 14:1675-1680 (1996); Cheung, V. G. et al., Nature Genetics 21(Suppl):15-19 (1999) for a discussion of array fabrication). DNA microarrays are miniature arrays containing gene fragments that are either synthesized directly onto or spotted onto glass or other substrates. Thousands of genes are usually represented in a single array. A typical microarray experiment involves the following steps: 1) preparation of fluorescently labeled target from RNA isolated from the sample, 2) hybridization of the labeled target to the microarray, 3) washing, staining, and scanning of the array, 4) analysis of the scanned image and 5) generation of gene expression profiles. Currently two main types of DNA microarrays are being used: oligonucleotide (usually 25 to 70 mers) arrays and gene expression arrays containing PCR products prepared from cDNAs. In forming an array, oligonucleotides can be either prefabricated and spotted to the surface or directly synthesized on to the surface (in situ). In some embodiments, a DNA microarray is a single-nucleotide polymorphism (SNP) microarrays, e.g., Affymetrix® SNP Array 6.0.

The Affymetrix GeneChip® system is a commercially available microarray system which comprises arrays fabricated by direct synthesis of oligonucleotides on a glass surface. Probe/Gene Arrays: Oligonucleotides, usually 25 mers, are directly synthesized onto a glass wafer by a combination of semiconductor-based photolithography and solid phase chemical synthesis technologies. Each array contains up to 400,000 different oligos and each oligo is present in millions of copies. Since oligonucleotide probes are synthesized in known locations on the array, the hybridization patterns and signal intensities can be interpreted in terms of gene identity and relative levels by the Affymetrix Microarray Suite software. Each gene is represented on the array by a series of different oligonucleotide probes. Each probe pair consists of a perfect match oligonucleotide and a mismatch oligonucleotide. The perfect match probe has a sequence exactly complimentary to the particular gene and thus measures the expression of the gene. The mismatch probe differs from the perfect match probe by a single base substitution at the center base position, disturbing the binding of the target gene transcript. This helps to determine the background and nonspecific hybridization that contributes to the signal measured for the perfect match oligo. The Microarray Suite software subtracts the hybridization intensities of the mismatch probes from those of the perfect match probes to determine the absolute or specific intensity value for each probe set. Probes are chosen based on current information from Genbank and other nucleotide repositories. The sequences are believed to recognize unique regions of the 3' end of the gene. A GeneChip Hybridization Oven ("rotisserie" oven) is used to carry out the hybridization of up to 64 arrays at one time. The fluidics station performs washing and staining of the probe arrays. It is completely automated and contains four modules, with each module holding one probe array. Each module is controlled independently through Microarray Suite software using preprogrammed fluidics protocols. The scanner is a confocal laser fluorescence scanner which measures fluorescence intensity emitted by the labeled cRNA bound to the probe arrays. The computer workstation with Microarray Suite software controls the fluidics station and the scanner. Microarray Suite software can control up to eight fluidics stations using preprogrammed hybridization, wash, and stain protocols for the probe array. The software also acquires and converts hybridization intensity data into a presence/absence call for each gene using appropriate algorithms. Finally, the software detects changes in gene expression between experiments by comparison analysis and formats the output into .txt files, which can be used with other software programs for further data analysis.

In some embodiments, for example when quantitative RT-PCR is used, the threshold cycle number is compared between FGF2 and VEGF, and the lower threshold indicates a higher level of the respective mRNA. As a nonlimiting example, in some embodiments, if FGF2 mRNA and VEGF mRNA levels are analyzed and the threshold cycle number (Ct) for FGF2 is 28 and the Ct for VEGF is 30, then FGF2 is at a higher level compared to VEGF. In various embodiments, similar comparisons may be carried out for any type of quantitative or semi-quantitative analytical method.

In some embodiments, the level of FGF2 and the level of VEGF are both normalized prior to comparison. In some embodiments, such normalization may allow comparison of FGF2 level to the VEGF level when the levels are not determined simultaneously and/or in the same assay reaction. One skilled in the art can select a suitable normalization mRNA, protein, or other factor, depending on the assay.

EXAMPLES

The examples discussed below are intended to be purely exemplary of the invention and should not be considered to limit the invention in any way. The examples are not intended to represent that the experiments below are all or the only experiments performed. It is understood that various other embodiments may be practiced, given the general description provided above. Efforts have been made to ensure accuracy with respect to numbers used (for example, amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1: FGF2 and VEGF Levels in Cancer Cell Lines

Relative levels of FGF2 and VEGF in human hepatocellular carcinoma (HCC) and renal cell carcinoma (RCC) cell lines was assessed using data from the Broad-Novartis Cancer Cell Line Encyclopedia (CCLE; www.broadinstitute.org/ccle/home). The CCLE is a publicly-available database providing genomic and transcriptomic data for over 1000 human cancer cell lines. Gene expression values were generated by performing Affymetrix U133 Plus 2.0 microarrays, Raw Affymetrix CEL files were converted to a single value for each probe set using Robust Multi-array Average (RMA), and values were normalized using quantile normalization. For FGF2, the average expression value across all cancer cells examined was 6.0 with a median value of 5.4. Kidney cancer cell lines demonstrated an average FGF2 expression value of 8.36 with a median of 8.47. Examining RCC cell lines that are known to grow in vivo, ACHN and Caki-1 were selected as having "high" FGF2 levels with values of 9.79 and 10.67, respectively. RCC cell lines Caki-2 and 786-0 had values of 8.26 and 7.20 and were therefore considered to represent "low" FGF2 levels. A498 had an FGF2 expression value of 9.85, which is above the average value for this tissue type, but this line also demonstrated high expression of VEGF and had an FGF2/VEGF ratio of <1 (discussed below). For liver cancer cell lines, the average and median expression values of FGF2 are 6.53 and 6.81, respectively.

HCC cell line SK-Hep-1 has an FGF2 value of 9.45, and was therefore considered as having "high" FGF2 level.

Relative expression values for VEGF were similarly assessed using the CCLE. The average VEGF value across all cancer cells examined was 8.13 with a median value of 8.06. Kidney cancer cell lines had an average VEGF value of 9.24 with a median of 9.38. RCC cell lines A498 and 786-0 have VEGF values of 9.77 and 9.39, and were therefore considered as having "high" VEGF levels. RCC cell lines ACHN and Caki-1 have VEGF values of 7.19 and 7.53, and are therefore considered as having "low" VEGF levels.

HCC lines demonstrated an average VEGF value of 8.40 with a median of 8.17. HCC cell line SK-Hep-1 cells have a VEGF value of 7.03, and was therefore considered as having "low" VEGF level.

In addition, we utilized the CCLE expression values to calculate the ratio of FGF2 to VEGF in these RCC and HCC cell lines. Cell lines with an FGF2/VEGF ratio of >1 included RCC lines ACHN and Caki-1 and HCC cell line SK-Hep-1, while cell lines with ratios at or below a value of 1 included RCC cell lines A498, Caki-2, and 786-0.

Tables 2 and 3 show the FGF2 and VEGF mRNA levels in each of the cancer cell lines, and the ratio of FGF2/VEGF levels. The cell lines in Table 2 are derived from human renal cell carcinomas and the cell lines in Table 3 are derived from human hepatocellular carcinomas.

TABLE 2

| RCC cell lines | | | |
|---|---|---|---|
| Cell line | FGF2 | VEGF | FGF2/VEGF |
| Caki-1 | 10.67 | 7.53 | 1.42 |
| ACHN | 9.79 | 7.19 | 1.36 |
| A-498 | 9.85 | 9.77 | 1.01 |
| Caki-2 | 8.26 | 8.61 | 0.96 |
| 786-0 | 7.20 | 9.39 | 0.77 |
| RCC Average | 8.36 | 9.24 | 0.93 |
| CCLE Average | 6.00 | 8.13 | 0.75 |

TABLE 3

| HCC cell lines | | | |
|---|---|---|---|
| Cell line | FGF2 | VEGF | FGF2/VEGF |
| SK-Hep-1 | 9.45 | 7.03 | 1.34 |
| SNU182 | 9.32 | 5.86 | 1.59 |
| HLF | 9.74 | 7.9 | 1.23 |
| Hep3B | 5.17 | 8.33 | 0.62 |
| PLC/PRF/5 | 4.76 | 7.78 | 0.61 |
| HepG2 | 4.62 | 8.60 | 0.54 |
| Huh7 | 4.19 | 7.83 | 0.53 |
| HCC Average | 6.53 | 8.40 | 0.80 |
| CCLE Average | 6.00 | 8.13 | 0.75 |

The cell lines were divided into two groups, cell lines with a ratio of FGF2/VEGF of >1 (in some embodiments, considered to be "high FGF2, low VEGF"), and cell lines with a ratio of FGF2/VEGF of <1 (in some embodiments, considered to be "low FGF2, high VEGF").

Example 2: Administration of FGFR1-ECD.339-Fc as a Single Agent, and in Combination with Pazopanib, in ACHN Xenograft Model Six week old female CB17 SCID mice were purchased from Charles River Laboratories (Wilmington, Mass.) and were acclimated for 1 week before the start of the study. Human clear cell renal carcinoma (RCC) cell line ACHN was purchased from ATCC (Manassas, Va.; Cat. No. CRL-1611). The cells were cultured for three passages in complete growth medium to expand for implantation. ACHN cells were cultured in Eagle's Minimum Essential Medium (EMEM). Medium was supplemented with 10% heat-inactivated Fetal Bovine Serum (FBS) and Antibiotic-Antimycotic solution. Cells were grown at 37° C. in a humidified atmosphere with 5% $CO_2$.

When the cultured cells reached 85-90% confluence, cells were harvested and resuspended in cold $Ca^{2+}$ and $Mg^{2+}$ free phosphate buffered saline (PBS) containing 50% Matrigel at $5 \times 10^7$ cells per milliliter. The cells were implanted subcutaneously over the right flank of the mice at $5 \times 10^6$ cells/100 μl/mouse. Mice were monitored twice weekly following cell implantation for tumor growth. Once ACHN tumors reached an average size of 100 $mm^3$, according to the formula Tumor size $(mm^3)=(width\ (mm) \times length\ (mm))^2/2$, mice were sorted and randomized (n=10) and treatment was initiated.

FGFR1-ECD.339-Fc (FP-1039) or albumin as a negative control was dosed at 15 mg/kg via intraperitoneal injection twice per week. Pazopanib (Votrient®) was dosed at 100 mg/kg via oral gavage daily, with vehicle serving as the negative control. FP-1039 treatment was initiated when tumors were 100 $mm^3$; subsequently, half of the FP-1039 treated tumor group was initiated for pazopanib co-treatment when tumors reached approximately 450 $mm^3$. Upon initiation of therapy, tumor sizes were measured in each mouse twice weekly. The length and width of each tumor was measured using calipers and the tumor size calculated according to the formula above. Mice were euthanized when the subcutaneous tumor volumes exceeded 2000 mm$^3$ or when the tumors became excessively necrotic.

Comparisons of tumor volume as a consequence of treatment with FP-1039 and/or pazopanib were determined to be statistically significant if P<0.05. P-values were calculated using unpaired, two-tailed t-test analyses of the calculated tumor volumes.

FIG. 1 shows the results of this experiment. The ACHN xenograft model (high FGF2, low VEGF; FGF2/VEGF=1.36; see Table 2) responded to FGFR1-ECD.339-Fc ("FP-1039") as a single therapy. Administration of pazopanib beginning at day 63 appeared to result in greater inhibition of tumor growth. See FIG. 1A. As shown in FIG. 1B, FGFR1-ECD.339-Fc ("FP-1039") alone resulted in 51% tumor growth inhibition (p<0.0001) at day 63. The combination of pazopanib and FGFR1-ECD.339-Fc ("FP-1039") appeared to result in greater tumor growth inhibition than FGFR1-ECD.339-Fc ("FP-1039") alone, although that result did not reach statistical significance (p=0.0552). See FIG. 1C. This analysis demonstrated that FGFR1-ECD.339-Fc alone significantly reduced tumor growth in the ACHN xenograft model, which has high FGF2 and low VEGF (ratio=1.36, see Table 2).

Example 3: Administration of FGFR1-ECD.339-Fc as a Single Agent, and in Combination with Pazopanib, in 786-0 Xenograft Model Six week old female CB17 SCID mice were purchased from Charles River Laboratories (Wilmington, Mass.) and were acclimated for 1 week before the start of the study. Human clear cell renal carcinoma (RCC) cell line 786-0 was purchased from ATCC (Manassas, Va.; Cat. No. CRL-1932). The cells were cultured for three passages in complete growth medium to expand for implantation. 786-0 was cultured in RPMI-1640 medium supplemented with 10% heat-inactivated Fetal Bovine Serum (FBS) and Antibiotic-Antimycotic solution. Cells were grown at 37° C. in a humidified atmosphere with 5% CO$_2$.

When the cultured cells reached 85-90% confluence, cells were harvested and resuspended in cold Ca$^{2+}$ and Mg$^{2+}$ free phosphate buffered saline (PBS) containing 50% Matrigel at 5×10$^7$ cells per milliliter. The cells were implanted subcutaneously over the right flank of the mice at 5×10$^6$ cells/100 µl/mouse. Mice were monitored twice weekly following cell implantation for tumor growth. Once 786-0 tumors reached an average size of 100 mm$^3$, according to the formula Tumor size (mm$^3$)=(width (mm)×length (mm))$^2$/2, mice were sorted and randomized (n=10) and treatment was initiated.

FGFR1-ECD.339-Fc (FP-1039) or albumin as a negative control was dosed at 15 mg/kg via intraperitoneal injection twice per week. Pazopanib (Votrient®) was dosed at 100 mg/kg via oral gavage daily, with vehicle serving as the negative control. FP-1039 and pazopanib dosing were initiated at the same time. Upon initiation of therapy, tumor sizes were measured in each mouse twice weekly. The length and width of each tumor was measured using calipers and the tumor size calculated according to the formula above. Mice were euthanized when the subcutaneous tumor volumes exceeded 2000 mm$^3$ or when the tumors became excessively necrotic.

Comparisons of tumor volume as a consequence of treatment with FP-1039 and/or pazopanib were determined to be statistically significant if P<0.05. P-values were calculated using unpaired, two-tailed t-test analyses of the calculated tumor volumes.

Figure 2:
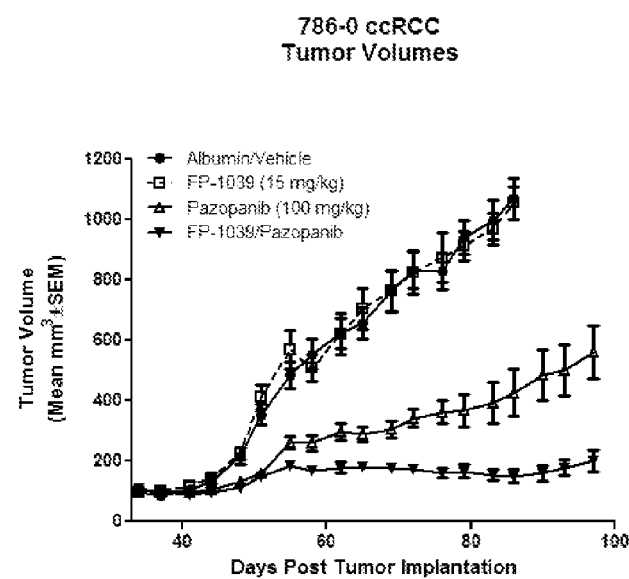
FIG. 2A-C show mean tumor volume at various time points in mice implanted with 786-0 cells and treated with FGFR1-ECD.339-Fc ("FP-1039"), pazopanib, FGFR1-ECD.339-Fc ("FP-1039") and pazopanib, or albumin, as described in Example 3.
Figure 2:
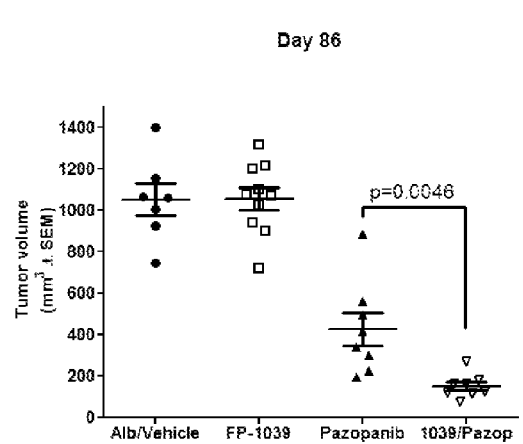
Figure 2:
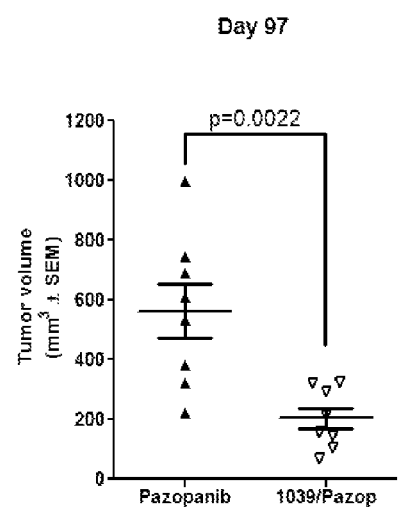

FIG. 2 shows the results of this experiment. The 786-0 xenograft model (low FGF2, high VEGF; FGF2/VEGF=0.77; see Table 2) did not respond to FGFR1-ECD.339-Fc ("FP-1039") as a single therapy. See FIGS. 2A and 2B. In contrast, the 786-0 xenograft model responded to pazopanib as a single therapy. See FIG. 2A-C. Surprisingly, the combination of FGFR1-ECD.339-Fc ("FP-1039") and pazopanib showed greater efficacy than pazopanib alone (p=0.0046 at day 86 and p=0.0022 at day 97). See id. This analysis demonstrated that FGFR1-ECD.339-Fc alone did not inhibit tumor growth in the 786-0 xenograft model, which has low FGF2 and high VEGF (ratio=0.77, see Table 2), while pazopanib was effective in that model. FGFR1-ECD.339-Fc in combination with pazopanib, however, showed even greater inhibition of tumor growth in the 786-0 xenograft model than pazopanib alone.

Example 4: Administration of FGFR1-ECD.339-Fc as a Single Agent, and in Combination with Pazopanib, in A498 Xenograft Model Six week old female CB17 SCID mice were purchased from Charles River Laboratories (Wilmington, Mass.) and were acclimated for 1 week before the start of the study. Human clear cell renal carcinoma (RCC) cell line A498 was purchased from ATCC (Manassas, Va.; Cat. No. HTB-44). The cells were cultured for three passages in complete growth medium to expand for implantation. A498 cells were cultured in Eagle's Minimum Essential Medium (EMEM) supplemented with 10% heat-inactivated Fetal Bovine Serum (FBS) and Antibiotic-Antimycotic solution. Cells were grown at 37° C. in a humidified atmosphere with 5% CO$_2$.

When the cultured cells reached 85-90% confluence, cells were harvested and resuspended in cold Ca$^{2+}$ and Mg$^{2+}$ free phosphate buffered saline (PBS) containing 50% Matrigel at 5×10$^7$ cells per milliliter. The cells were implanted subcutaneously over the right flank of the mice at 5×10$^6$ cells/100 µl/mouse. Mice were monitored twice weekly following cell implantation for tumor growth. Once A498 tumors reached an average size of 100 mm$^3$, according to the formula Tumor size (mm$^3$)=(width (mm)×length (mm))$^2$/2, mice were sorted and randomized (n=10) and treatment was initiated.

FGFR1-ECD.339-Fc (FP-1039) or albumin as a negative control was dosed at 15 mg/kg via intraperitoneal injection twice per week. Pazopanib (Votrient®) was dosed at 100 mg/kg via oral gavage daily, with vehicle serving as the negative control. FP-1039 and pazopanib dosing was initiated at the same time. Upon initiation of therapy, tumor sizes were measured in each mouse twice weekly. The length and width of each tumor was measured using calipers and the tumor size calculated according to the formula above. Mice were euthanized when the subcutaneous tumor volumes exceeded 2000 mm$^3$ or when the tumors became excessively necrotic. On day 89 (post tumor cell inoculation), the pazopanib-treated tumor group (average tumor volume of 410 mm$^3$) was separated into two individual groups for further treatment and analysis. One group continued receiving daily pazopanib treatment alone, and the second group received daily pazopanib treatment in addition to intraperitoneal injections of FGFR1-ECD.339-Fc twice per week. Tumors continued to be measured twice weekly according to the method above.

Comparisons of tumor volume as a consequence of treatment with FP-1039 and/or pazopanib were determined to be statistically significant if P<0.05. P-values were calculated using unpaired, two-tailed t-test analyses of the calculated tumor volumes.

Figure 3:
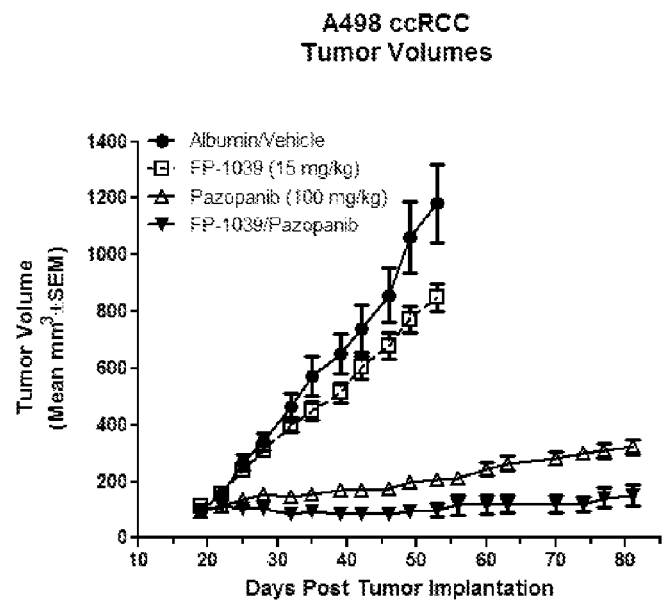
FIG. 3A-C show mean tumor volume at various time points in mice implanted with A498 cells and treated with FGFR1-ECD.339-Fc ("FP-1039"), pazopanib, FGFR1-ECD.339-Fc ("FP-1039") and pazopanib, or albumin, as described in Example 4.
Figure 3:
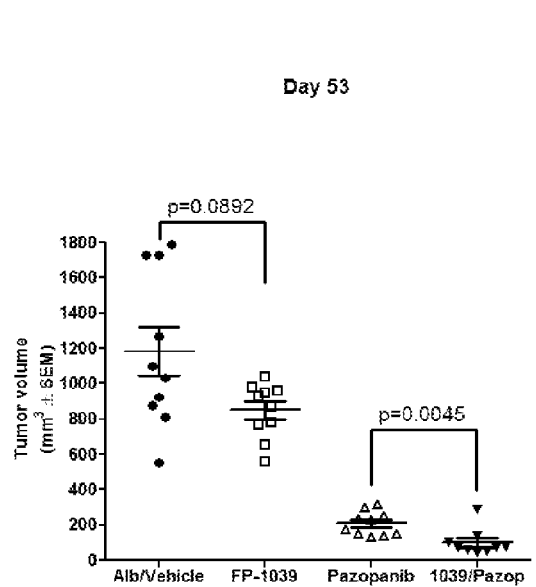
Figure 3:
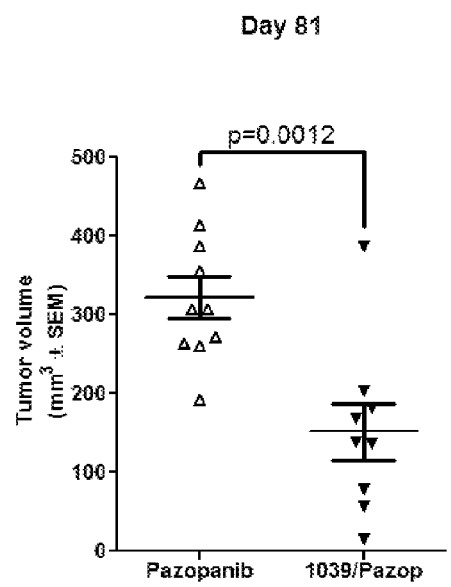

FIG. 3 shows the results of the first phase of the experiment. The A498 xenograft model (low FGF2, high VEGF; FGF2/VEGF=1.01; see Table 2) showed little response to FGFR1-ECD.339-Fc ("FP-1039") as a single therapy. See FIG. 3A. In contrast, the A498 xenograft model responded to pazopanib as a single therapy. See FIG. 3A-C. Surprisingly, the combination of FGFR1-ECD.339-Fc ("FP-1039") and pazopanib showed greater efficacy than pazopanib alone (p=0.0045 at day 53 and p=0.0012 at day 81). See id. This analysis demonstrated that FGFR1-ECD.339-Fc alone did not inhibit tumor growth in the A498 xenograft model, which has low FGF2 and high VEGF (ratio=1.01, see Table 2), while pazopanib was effective in that model. FGFR1-ECD.339-Fc in combination with pazopanib, however, showed even greater inhibition of tumor growth in the A498 xenograft model than pazopanib alone.

Figure 14:
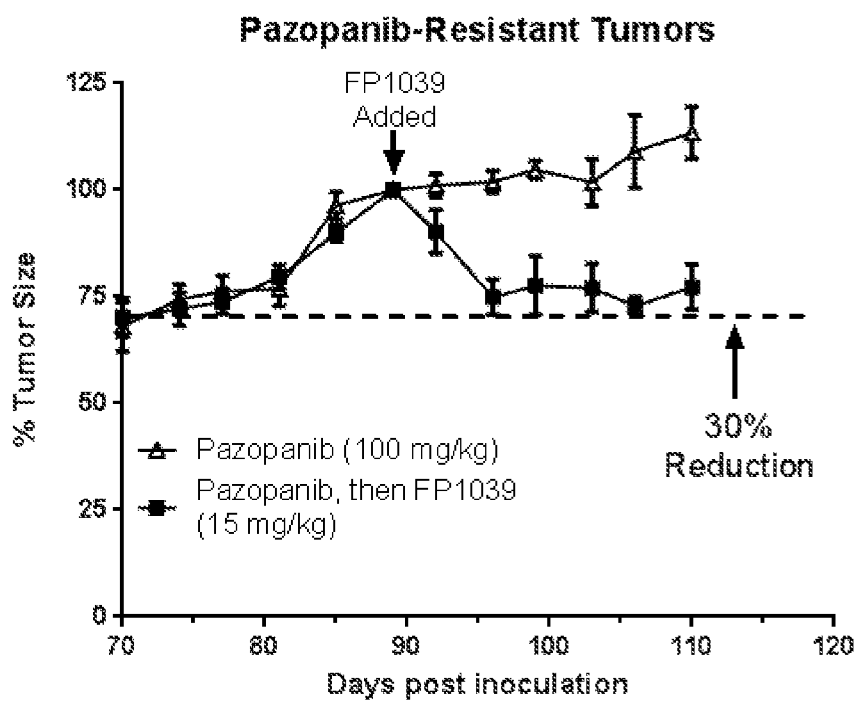
FIG. 14A-B show (A) percent tumor size in mice implanted with A498 cells and treated with pazopanib alone or pazopanib and FGFR1-ECD.339-Fc ("FP-1039") beginning on day 89, relative to tumor size in pazopanib-treated A498 xenograft model mice on day 89; and (B) percent tumor size at day 110, as described in Example 4.
Figure 14:
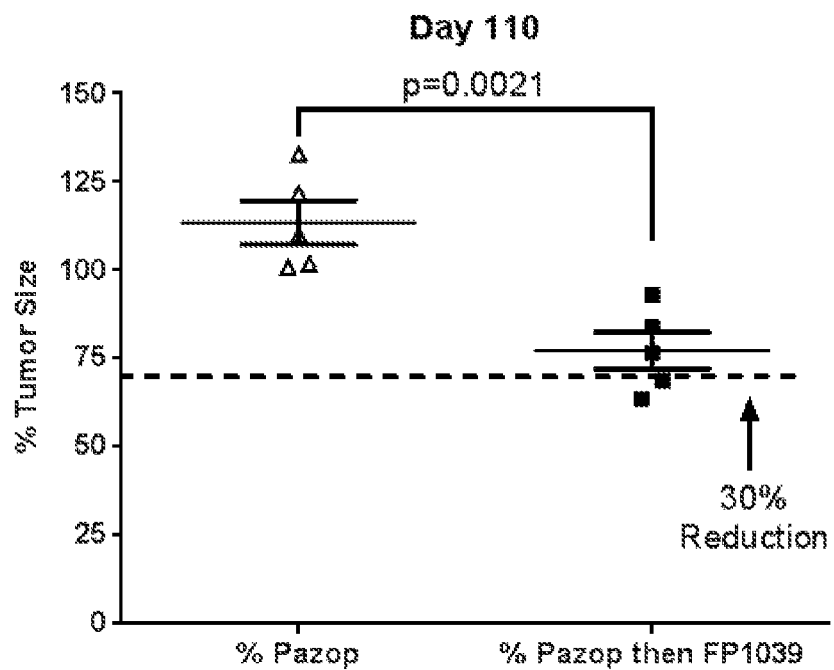

FIG. 14 shows the results of the second phase of the experiment. The change in tumor size is shown by graphing the percent tumor volume relative to the day upon which animals were re-grouped (day 89). See FIG. 14A. Percent tumor volume was calculated for each individual animal using the formula % Tumor Size=100×(volume ($mm^3$)/volume on day 89 ($mm^3$)) Comparisons of percent tumor size as a consequence of treatment with FGFR1-ECD.339-Fc ("FP-1039") and/or pazopanib were determined to be statistically significant if P<0.05. P-values were calculated using unpaired, two-tailed t-test analyses of the calculated percent tumor size on the final day upon which tumors were measured (Day 110). As shown in FIG. 14B, administration of pazopanib+FGFR1-ECD.339-Fc to mice whose tumors had become resistant to pazopanib treatment resulted in a significant reduction of tumor size relative to continued pazopanib treatment alone.

Example 5: Administration of FGFR1-ECD.339-Fc as a Single Agent, and in Combination with Pazopanib, in Caki-2 Xenograft Model Six week old female CB17 SCID mice were purchased from Charles River Laboratories (Wilmington, Mass.) and were acclimated for 1 week before the start of the study. Human clear cell renal carcinoma (RCC) cell line Caki-2 was purchased from ATCC (Manassas, Va.; Cat. No. HTB-47). The cells were cultured for three passages in complete growth medium to expand for implantation. Caki-2 was cultured in McCoy's 5a Medium Modified supplemented with 10% heat-inactivated Fetal Bovine Serum (FBS) and Antibiotic-Antimycotic solution. Cells were grown at 37° C. in a humidified atmosphere with 5% $CO_2$.

When the cultured cells reached 85-90% confluence, cells were harvested and resuspended in cold $Ca^{2+}$ and $Mg^{2+}$ free phosphate buffered saline (PBS) containing 50% Matrigel at $5\times10^7$ cells per milliliter. The cells were implanted subcutaneously over the right flank of the mice at $5\times10^6$ cells/100 µl/mouse. Mice were monitored twice weekly following cell implantation for tumor growth. For Caki-2 tumors, treatment was initiated once tumors reached an average size of 200 $mm^3$, according to the formula Tumor size ($mm^3$)=(width (mm)×length $(mm))^2/2$, mice were sorted and randomized (n=10) and treatment was initiated.

FGFR1-ECD.339-Fc (FP-1039) or albumin as a negative control was dosed at 15 mg/kg via intraperitoneal injection twice per week. Pazopanib (Votrient®) was dosed at 100 mg/kg via oral gavage daily, with vehicle serving as the negative control. FP-1039 and pazopanib dosing was initiated at the same time. Upon initiation of therapy, tumor sizes were measured in each mouse twice weekly. The length and width of each tumor was measured using calipers and the tumor size calculated according to the formula above. Mice were euthanized when the subcutaneous tumor volumes exceeded 2000 $mm^3$ or when the tumors became excessively necrotic.

Comparisons of tumor volume as a consequence of treatment with FP-1039 and/or pazopanib were determined to be statistically significant if P<0.05. P-values were calculated using unpaired, two-tailed t-test analyses of the calculated tumor volumes.

Figure 4:
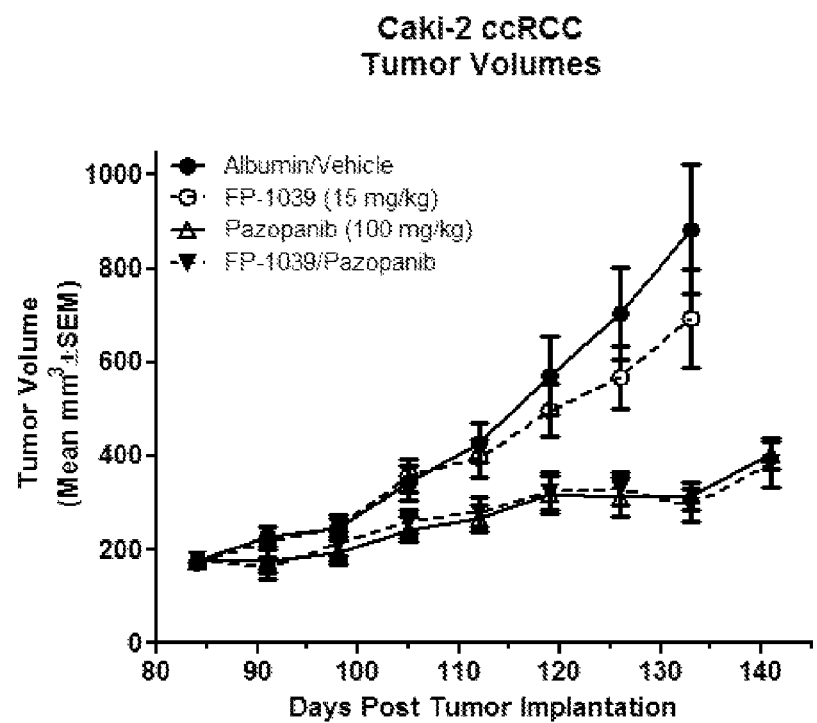
FIG. 4A-B show mean tumor volume at various time points in mice implanted with Caki-2 cells and treated with FGFR1-ECD.339-Fc ("FP-1039"), pazopanib, FGFR1-ECD.339-Fc ("FP-1039") and pazopanib, or albumin, as described in Example 5.
Figure 4:
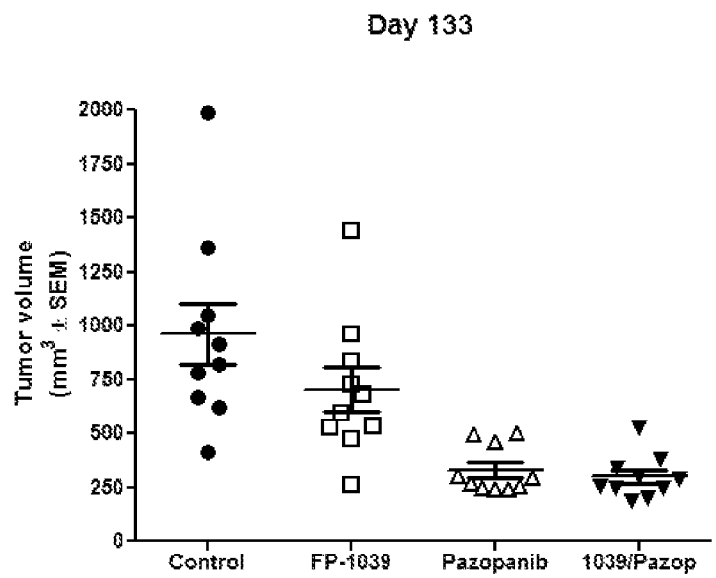

FIG. 4 shows the results of this experiment. The Caki-2 xenograft model (low FGF2, high VEGF; FGF2/VEGF=0.96; see Table 2) showed little response to FGFR1-ECD.339-Fc ("FP-1039") as a single therapy. See FIG. 4A. In contrast, the Caki-2 xenograft model showed a strong response to pazopanib as a single therapy. See FIGS. 4A and 4B. In this experiment, the combination of FGFR1-ECD.339-Fc ("FP-1039") and pazopanib was as effective as pazopanib as a single therapy. See id. This analysis demonstrated that FGFR1-ECD.339-Fc alone did not inhibit tumor growth in the Caki-2 xenograft model, which has low FGF2 and high VEGF (ratio=0.96, see Table 2), while pazopanib was effective in that model. FGFR1-ECD.339-Fc in combination with pazopanib showed similar inhibition as pazopanib alone, which may be a reflection of the particular sensitivity of this model to pazopanib. According to the Pharmacology/Toxicology Review and Evaluation for New Drug Application (NDA) No. 22-465 for pazopanib, submitted Dec. 19, 2008, to the Center for Drug Evaluation and Research, Caki-2 tumor xenografts in CB-17 SCID mice show tumor inhibition of 90%, 77%, and 99% at 10, 30, and 100 mg/kg pazopanib, respectively.

Example 6: Administration of FGFR1-ECD.339-Fc as a Single Agent, and in Combination with Pazopanib, in SK-Hep-1 Xenograft Model Six week old female CB17 SCID mice were purchased from Charles River Laboratories (Wilmington, Mass.) and were acclimated for 1 week before the start of the study. Human hepatocellular carcinoma (HCC) cell line SK-Hep-1 was purchased from ATCC (Cat. No. HTB-52). The cells were cultured for three passages in complete growth medium to expand for implantation. SK-Hep-1 cells were cultured in Eagle's Minimum Essential Medium (EMEM) supplemented with 10% heat-inactivated Fetal Bovine Serum (FBS) and Antibiotic-Antimycotic solution. Cells were grown at 37° C. in a humidified atmosphere with 5% $CO_2$.

When the cultured cells reached 85-90% confluence, cells were harvested and resuspended in cold $Ca^{2+}$ and $Mg^{2+}$ free phosphate buffered saline (PBS) containing 50% Matrigel at $5\times10^7$ cells per milliliter. The cells were implanted subcutaneously over the right flank of the mice at $5\times10^6$ cells/100 µl/mouse. Mice were monitored twice weekly following cell implantation for tumor growth. Once SK-Hep-1 tumors reached an average size of 100 $mm^3$, according to the formula Tumor size ($mm^3$)=(width (mm)×length $(mm))^2/2$, mice were sorted and randomized (n=10) and treatment was initiated.

FGFR1-ECD.339-Fc (FP-1039) or albumin as a negative control was dosed at 15 mg/kg via intraperitoneal injection twice per week. Pazopanib (Votrient®) was dosed at 100 mg/kg via oral gavage daily, with vehicle serving as the negative control. FP-1039 treatment was initiated when tumors were 100 mm3; subsequently, half of the FP-1039 treated tumor group was initiated for pazopanib co-treatment when tumors reached approximately 550 mm$^3$. Upon initiation of therapy, tumor sizes were measured in each mouse twice weekly. The length and width of each tumor was measured using calipers and the tumor size calculated according to the formula above. Mice were euthanized when the subcutaneous tumor volumes exceeded 2000 mm$^3$ or when the tumors became excessively necrotic.

Comparisons of tumor volume as a consequence of treatment with FP-1039 and/or pazopanib were determined to be statistically significant if P<0.05. P-values were calculated using unpaired, two-tailed t-test analyses of the calculated tumor volumes.

Figure 5:
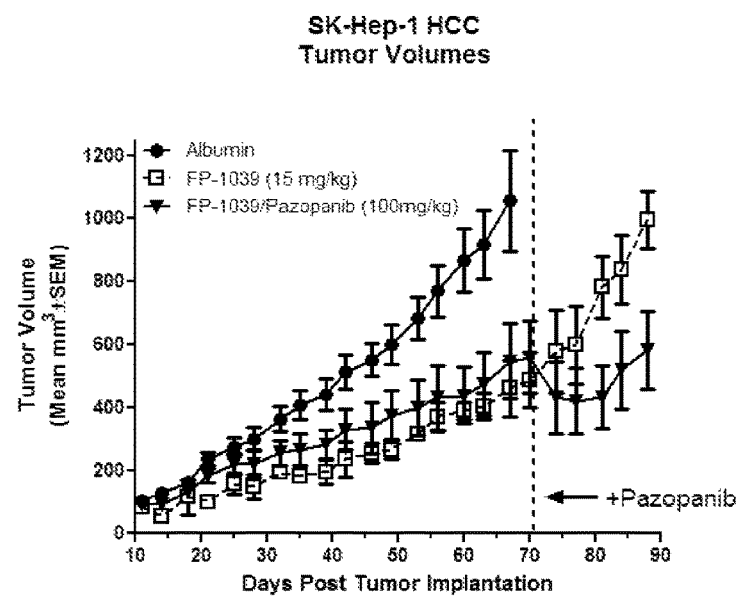
FIG. 5A-C show mean tumor volume at various time points in mice implanted with SK-Hep-1 cells and treated with FGFR1-ECD.339-Fc ("FP-1039"), pazopanib, FGFR1-ECD.339-Fc ("FP-1039") and pazopanib, or albumin, as described in Example 6.
Figure 5:
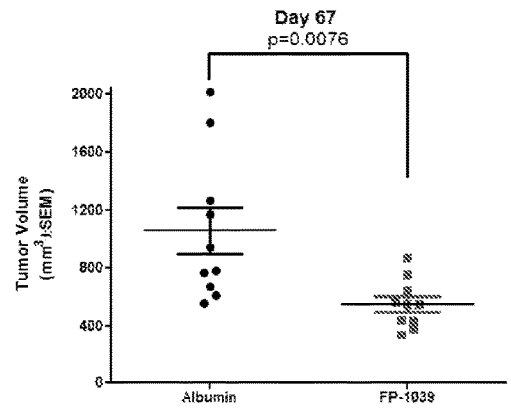
Figure 5:
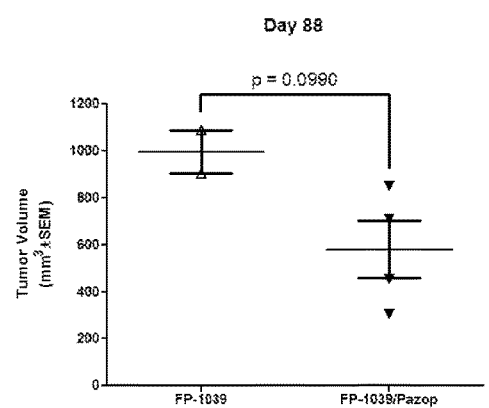

FIG. 5 shows the results of this experiment. The SK-Hep-1 xenograft model (high FGF2, low VEGF; FGF2/VEGF=1.34; see Table 3) responded to FGFR1-ECD.339-Fc ("FP-1039") as a single therapy (p=0.0076). See FIGS. 5A and 5B. Addition of pazopanib did not significantly increase tumor growth inhibition in that experiment. See FIG. 5C. This analysis demonstrated that FGFR1-ECD.339-Fc alone inhibited tumor growth in the SK-Hep-1 xenograft model, which has high FGF2 and low VEGF (ratio=1.34, see Table 3).

Example 7: Administration of FGFR1-ECD.339-Fc as a Single Agent in HepG2, Huh7, and Hep3B Xenograft Models Six week old female CB17 SCID mice were purchased from Charles River Laboratories (Wilmington, Mass.) and were acclimated for 1 week before the start of the study. Human hepatocellular carcinoma (HCC) cell lines HepG2 and Hep3B were purchased from ATCC (Manassas, Va.) and Huh7 was purchased from JCRB (Japanese Collection of Research Bioresources). The cells were cultured for three passages in complete growth medium to expand for implantation. HepG2 and Hep3B cells were cultured in Dulbecco's Modified Eagle Medium (DMEM) supplemented with 10% Fetal Bovine Serum (FBS), 2 mM L-Glutamine, and Penicillin-Streptomycin antibiotic solution. Huh7 cells were cultured in Dulbecco's Modified Eagle Medium (DMEM) supplemented with 10% Fetal Bovine Serum (FBS) and Penicillin-Streptomycin antibiotic solution. Cells were grown at 37° C. in a humidified atmosphere with 5% $CO_2$.

When the cultured cells reached 85-90% confluence, cells were harvested and resuspended in cold $Ca^{2+}$ and $Mg^{2+}$ free phosphate buffered saline (PBS) containing 50% Matrigel. The cells were implanted subcutaneously over the right flank of the mice at $5 \times 10^6$ cells/100 µl/mouse for HepG2 and Hep3B and $1 \times 10^6$ cells/100 µl/mouse for Huh7. Mice were monitored twice weekly following cell implantation for tumor growth.

FGFR1-ECD.339-Fc (FP-1039) or albumin as a negative control was dosed at 15 mg/kg via intraperitoneal injection twice per week. For Huh7 xenograft, vehicle was used as a negative control. For HepG2 and Hep3B, dosing was initiated one day after tumor cell inoculation. Huh7 tumors were allowed to reach 90 mm$^3$+/−20 mm$^3$, at which point they were stratified into groups and dosing was initiated. Upon initiation of therapy, tumor sizes were measured in each mouse twice weekly. The length and width of each tumor was measured using calipers and the tumor size calculated according to the formula Tumor size (mm$^3$)=(width (mm)× length (mm))$^2$/2. Mice were euthanized when the subcutaneous tumor volumes exceeded 500 mm$^3$ for HepG2, 600 mm$^3$ for Hep3B, or 2000 mm$^3$ for Huh7.

Comparisons of tumor volume as a consequence of treatment with FP-1039 were determined to be statistically significant if P<0.05. P-values were calculated using unpaired, two-tailed t-test analyses of the calculated tumor volumes.

Figure 6:
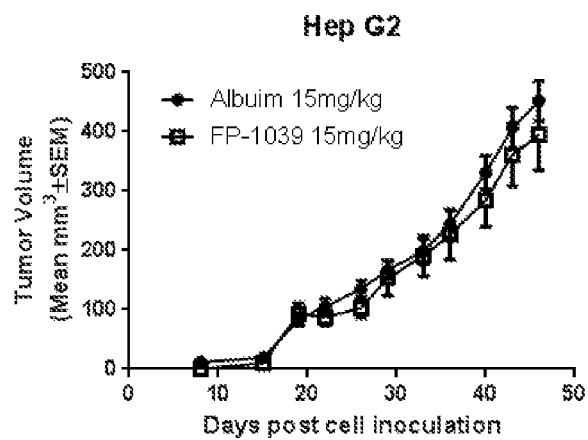
FIG. 6A-C show mean tumor volume at various time points in mice implanted with (A) HepG2 cells, (B) Huh7 cells, and (C) Hep3B cells and treated with FGFR1-ECD.339-Fc ("FP-1039") or albumin or vehicle, as described in Example 7.
Figure 6:
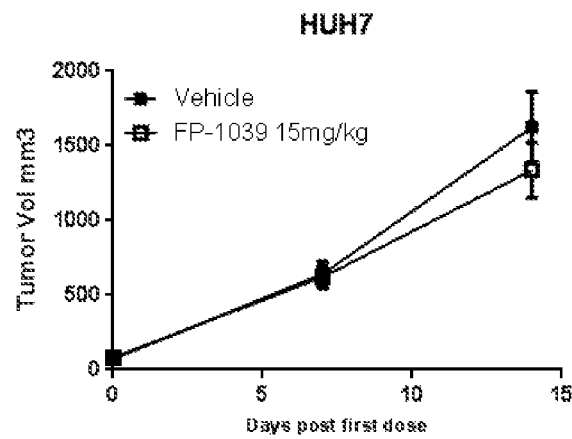
Figure 6:
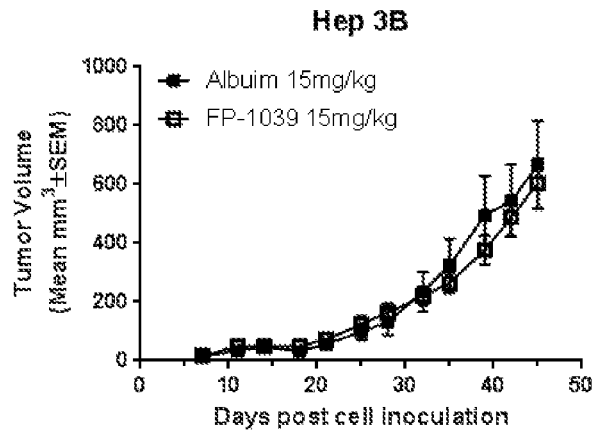

FIG. 6 shows the results of this experiment. There was no single agent efficacy using FP-1039 observed in HepG2 cells, Hep3B cells, or Huh7 cells, each of which has an FGF2/VEGF ratio of <1. See Table 3.

Example 8: Administration of FGFR1-ECD.339-Fc as a Single Agent, and in Combination with Sorafenib, in SK-Hep-1 Xenograft Model Six week old female CB17 SCID mice were purchased from Charles River Laboratories (Wilmington, Mass.) and were acclimated for 1 week before the start of the study. Human hepatocellular carcinoma (HCC) cell line SK-Hep-1 was purchased from ATCC (Cat. No. HTB-52). The cells were cultured for three passages in complete growth medium to expand for implantation. SK-Hep-1 cells were cultured in Eagle's Minimum Essential Medium (EMEM) supplemented with 10% heat-inactivated Fetal Bovine Serum (FBS) and Antibiotic-Antimycotic solution. Cells were grown at 37° C. in a humidified atmosphere with 5% $CO_2$.

When the cultured cells reached 85-90% confluence, cells were harvested and resuspended in cold $Ca^{2+}$ and $Mg^{2+}$ free phosphate buffered saline (PBS) containing 50% Matrigel at $5 \times 10^7$ cells per milliliter. The cells were implanted subcutaneously over the right flank of the mice at $5 \times 10^6$ cells/100 µl/mouse. Mice were monitored twice weekly following cell implantation for tumor growth. Once SK-Hep-1 tumors reached an average size of 100 mm$^3$, according to the formula Tumor size (mm$^3$)=(width (mm)×length (mm))$^2$/2, mice were sorted and randomized (n=10) and treatment was initiated.

FGFR1-ECD.339-Fc (FP-1039) or albumin as a negative control was dosed at 15 mg/kg via intraperitoneal (IP) injection twice per week. Sorafenib (Nexavar®) was dosed at 20 mg/kg via oral gavage daily, five times per week. As a control for sorafenib treatment, animals were dosed via daily gavage with vehicle (1% DMSO/19% 1:1 Cremophor/Ethanol/80% Water). FP-1039 treatment was initiated when tumors were 100 mm$^3$. Upon initiation of therapy, tumor sizes were measured in each mouse twice weekly. The length and width of each tumor was measured using calipers and the tumor size calculated according to the formula above. Mice were euthanized when the subcutaneous tumor volumes exceeded 1000 mm$^3$, when the tumors became excessively necrotic, or when animal health became compromised.

Comparisons of tumor volume as a consequence of treatment with FP-1039 and/or sorafenib were determined to be statistically significant if P<0.05. P-values were calculated using unpaired, two-tailed t-test analyses of the calculated tumor volumes on the final day upon which tumors were measured.

Figure 7:
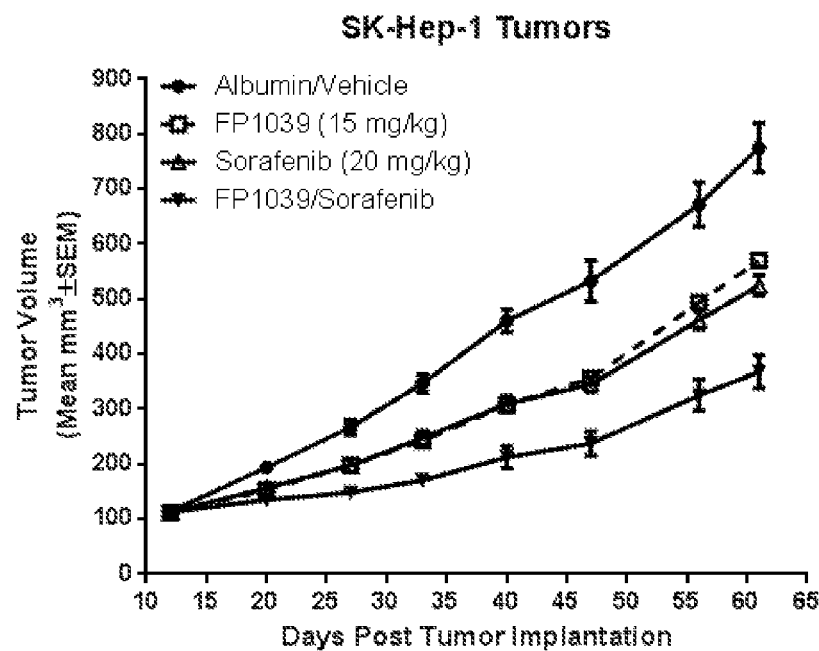
FIG. 7A-C show (A) mean tumor volume at various time points, and (B) final tumor volume and (C) final tumor weight, in mice implanted with SK-Hep-1 cells and treated with FGFR1-ECD.339-Fc ("FP-1039"), sorafenib, FGFR1-ECD.339-Fc ("FP-1039") and sorafenib, or albumin, as described in Example 8.
Figure 7:
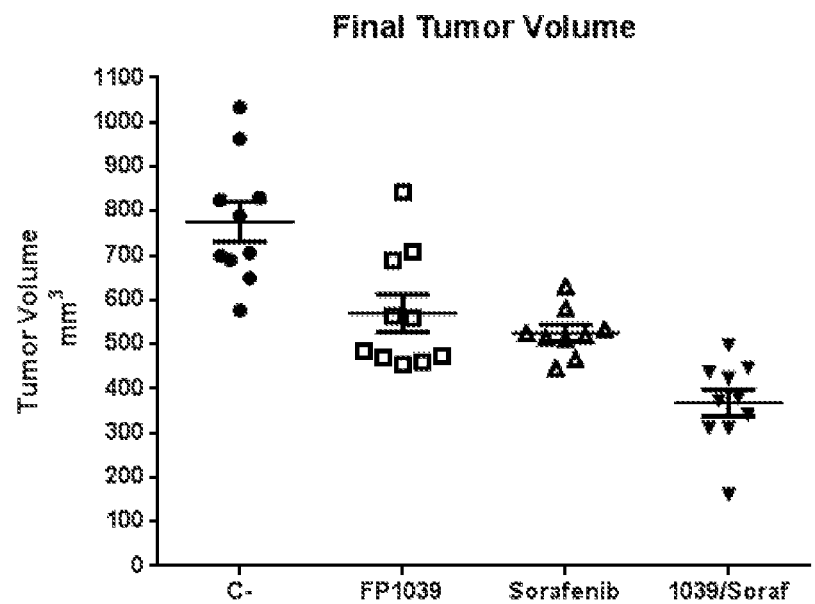
Figure 7:
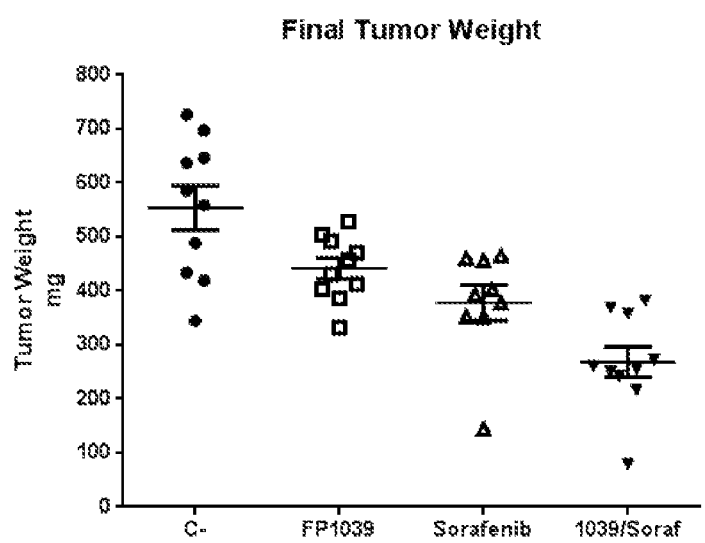

FIG. 7 shows the results of this experiment. The SK-Hep-1 xenograft model (high FGF2, low VEGF; FGF2/VEGF=1.34; see Table 3) responded to FGFR1-ECD.339-Fc ("FP-1039") as a single therapy (p=0.0036 at 61 days), and also responded to sorafenib as a single agent therapy (p<0.0001 at 61 days). See FIGS. 7A, B, and C. The combination of FGFR1-ECD.339-Fc and sorafenib significantly increased tumor growth inhibition over sorafenib alone (p=0.0004 at 61 days) or over FGFR1-ECD.339-Fc alone (p=0.001). See id. This analysis demonstrated that FGFR1-ECD.339-Fc alone inhibited tumor growth in the SK-Hep-1 xenograft model, which has high FGF2 and low VEGF, and that the combination of FGFR1-ECD.339-Fc and sorafenib had an additive effect, significantly increasing tumor growth inhibition over sorafenib or FGFR1-ECD.339-Fc alone.

FGFR1-ECD.339-Fc as a single agent, and in combination with sorafenib, was also tested in a HepG2 xenograft model. HepG2 cells have a low FGF2/VEGF ratio of 0.54, and FGFR1-ECD.339-Fc was not effective as a single agent. See Example 7. While sorafenib as a single agent inhibits tumor growth in a HepG2 xenograft model, the combination of FGFR1-ECD.339-Fc and sorafenib was not found to be more effective than sorafenib alone.

Example 9: Predictors of FGFR1-ECD.339-Fc Response

The RNA expression of a panel of genes including FGF ligands, FGF receptors, FGF binding proteins, FGF signaling molecules, and a group of angiogenesis-related targets was determined in a set of 35 tumor cell lines and xenografts using qRT-PCR. RNA was extracted from cell lines grown in vitro or tumor xenografts grown in vivo using the RNAeasy® mini kit (Qiagen, Germany). Extracted RNA was treated with DNAse I prior to creating cDNA with random hexamer priming and reverse transcriptase using the QuantiTect Reverse Transcription Kit (Qiagen, Germany) Human and mouse RNA expression was determined using QuantiTect Primer Assays (Qiagen, Germany) employing a human GUSB control reference QuantiTect Primer Assay (Qiagen, Germany). QuantiTect SYBR Green PCR Kits (Qiagen, Germany) were used to quantify mRNA expression levels using real-time qRT-PCR and an ABI Prism ViiA™ 7 Real-Time PCR System (Applied Biosystems, Foster City, Calif.). Relative gene expression quantification was calculated according to the comparative Ct method using human GUSB as a reference and commercial RNA controls (Stratagene, La Jolla, Calif.). Relative quantification was determined according to the formula: $2^{-(\Delta Ct\ sample - \Delta Ct\ calibrator)}$.

The tumor cell lines and xenografts used in this experiment are shown in Table 4. Also shown in Table 4 are the dosing schedule for FGFR1-ECD.339-Fc in a mouse xenograft model, the percent tumor growth inhibition (TGI (%)) and the statistical significance of the tumor growth inhibition (P Value), as well as whether the FGFR1 gene is amplified in the cell line.

TABLE 4

Anti-tumor activity of FGFR1-ECD.339-Fc in a panel of xenograft models

| Tumor type | Xenograft model | Cell line/PDX | Dosing route | Dose | Dose sched. | TGI (%) | P Value | FGFR1 amp. status |
|---|---|---|---|---|---|---|---|---|
| Colon | HCT116 | Cell Line | IP | 15 mg/kg | BIW | 0% | ns | Non-amplified |
| | Colo205 | Cell Line | IV | 5 mg/kg | BIW | 38% | P < 0.001 | Non-amplified |
| | Colo201 | Cell Line | IP | 15 mg/kg | BIW | 0% | ns | Non-amplified |
| Renal | G-401 | Cell Line | IP | 15 mg/kg | BIW | 36% | P < 0.05 | Non-amplified |
| | A498 | Cell Line | IP | 15 mg/kg | BIW | 7% | ns | Non-amplified |
| | Caki-1 | Cell Line | IV | 10 mg/kg | BIW | 81% | P < 0.001 | Non-amplified |
| Lung | A549 | Cell Line | IP | 10 mg/kg | BIW | 38% | P < 0.05 | Non-amplified |
| | NCI-H460 | Cell Line | IP | 10 mg/kg | BIW | 35% | P < 0.05 | Non-amplified |
| | NCI-H226 | Cell Line | IP | 15 mg/kg | 3x/w | 55% | P < 0.001 | Non-amplified |
| | NCI-H520 | Cell Line | IP | 20 mg/kg | BIW | 47% | P < 0.05 | Amplified |
| | NCI-H1703 | Cell Line | IP | 15 mg/kg | BIW | 31% | P < 0.05 | Amplified |
| | NCI-H2126 | Cell Line | IP | 15 mg/kg | BIW | 0% | ns | Non-amplified |
| | NCI-H441 | Cell Line | IP | 15 mg/kg | BIW | 0% | ns | Non-amplified |
| | NCI-H358 | Cell Line | IP | 15 mg/kg | BIW | 0% | ns | Non-amplified |
| | NCI-H522 | Cell Line | IP | 10 mg/kg | BIW | 42% | P < 0.05 | Non-amplified |
| | NCI-H1581 | Cell Line | IP | 15 mg/kg | BIW | 74% | P = 0.002 | Amplified |
| | DMS53 | Cell Line | IP | 15 mg/kg | BIW | 64% | 0.003 | Amplified |
| | DMS114 | Cell Line | IP | 15 mg/kg | BIW | 64% | P < 0.001 | Amplified |
| | Calu-1 | Cell Line | IP | 15 mg/kg | BIW | 0% | ns | Non-amplified |
| | D35087 | PDX | IP | 15 mg/kg | BIW | 57% | P < 0.01 | Non-amplified |
| | D37638 | PDX | IP | 15 mg/kg | BIW | 0% | ns | Non-amplified |
| | D35376 | PDX | IP | 15 mg/kg | BIW | 0% | ns | Non-amplified |
| | LXFA-737 | PDX | IP | 15 mg/kg | BIW | 0% | ns | Non-amplified |
| | LXFA-629 | PDX | IP | 15 mg/kg | BIW | 65% | P = 0.007 | Non-amplified |
| Mesothelioma | MSTO-211H | Cell Line | IP | 15 mg/kg | BIW | 64% | P < 0.0001 | Non-amplified |
| Glioblastoma | U-87 | Cell Line | IP | 15 mg/kg | BIW | 0% | ns | Non-amplified |
| | U-118 | Cell Line | IP | 15 mg/kg | BIW | 36% | ns | Non-amplified |
| | U-251 | Cell Line | IP | 15 mg/kg | BIW | 48% | P = 0.0078 | Non-amplified |
| Retinoblastoma | Y79 | Cell Line | IP | 10 mg/kg | BIW | 0% | ns | Non-amplified |
| Prostate | Du145 | Cell Line | IP | 0.15 mg/kg | 3x/w | 31% | ns | Non-amplified |
| Endometrial | MFE-280 | Cell Line | IP | 15 mg/kg | BIW | 96% | P < 0.001 | Non-amplified |
| | HEC-1B | Cell Line | IP | 15 mg/kg | BIW | 30% | P < 0.05 | Non-amplified |
| | MFE-319 | Cell Line | IP | 15 mg/kg | BIW | 0% | ns | Non-amplified |
| Breast | MDA-MB-231 | Cell Line | IP | 15 mg/kg | BIW | 0% | ns | Non-amplified |
| | JIMT1 | Cell Line | IP | 1 mg/kg | BIW | 28% | P < 0.05 | Non-amplified |

An exemplary xenograft experiment is as follows. For Caki-1 and MSTO-211H, five million cells were implanted subcutaneously over the right flank of SCID mice (N=10 per group). FGFR1-ECD.339-Fc or albumin was administered i.p. twice a week at the dose indicated in Table 4. In the renal cell carcinoma (RCC) Caki-1 model, administration of FGFR1-ECD.339-Fc at 10 mg/kg twice a week for 6 weeks resulted in 81% (P<0.001) tumor growth inhibition (TGI). In the MSTO-211H mesothelioma model, FGFR1-ECD.339-Fc administration reduced tumor growth by 64% (P<0.0001). In responding tumors, FGFR1-ECD.339-Fc significantly reduced tumor volume as assessed by area-under-the-curve (AUC) analysis. Responses were observed in 19/35 (54%) of the models examined, with a range of 25-96% inhibition (see Table 4).

RNA expression of a panel of genes including FGF ligands, FGF receptors, FGF binding proteins and FGF signaling molecules was examined using qRT-PCR in certain xenograft models from Table 4. Gene expression was then correlated to FGFR1-ECD.339-Fc response to determine RNA expression signatures positively and negatively correlated with anti-tumor activity.

Figure 8:
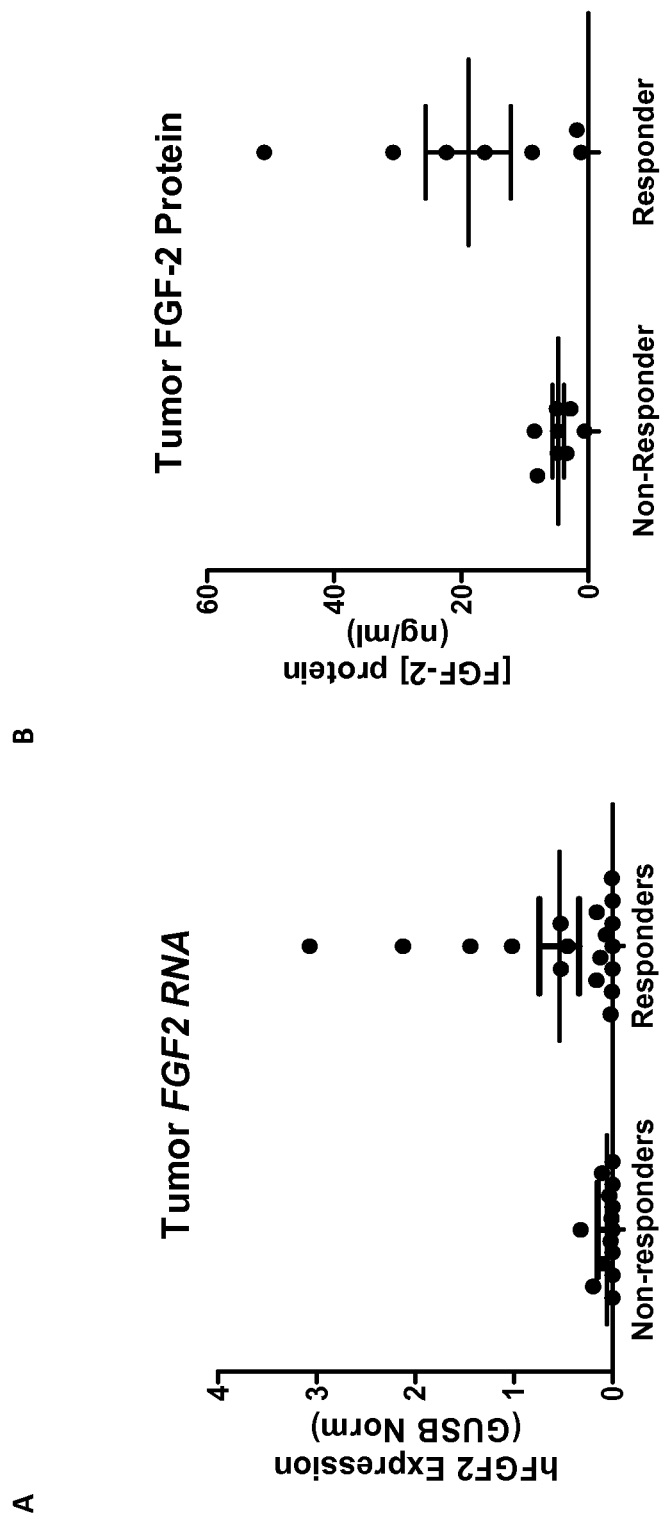
FIG. 8A-B show (A) FGF2 mRNA (normalized to GUSB) and (B) FGF2 protein expression (normalized to total protein) in FGFR1-ECD.339-Fc responder and non-responder xenografts, as described in Example 9.

FIG. 8 shows (A) FGF2 mRNA (normalized to GUSB) and (B) FGF2 protein expression in FGFR1-ECD.339-Fc responder and non-responder xenografts. Expression of FGF2 (P=0.03569) was positively associated with FGFR1-ECD.339-Fc response. FGF2 displayed a high ratio (247.7-fold) of mRNA gene expression between FGFR1-ECD.339-Fc responder and non-responder xenografts. FGF2 protein levels were also confirmed to correlate with FGFR1-ECD.339-Fc response.

Figure 9:
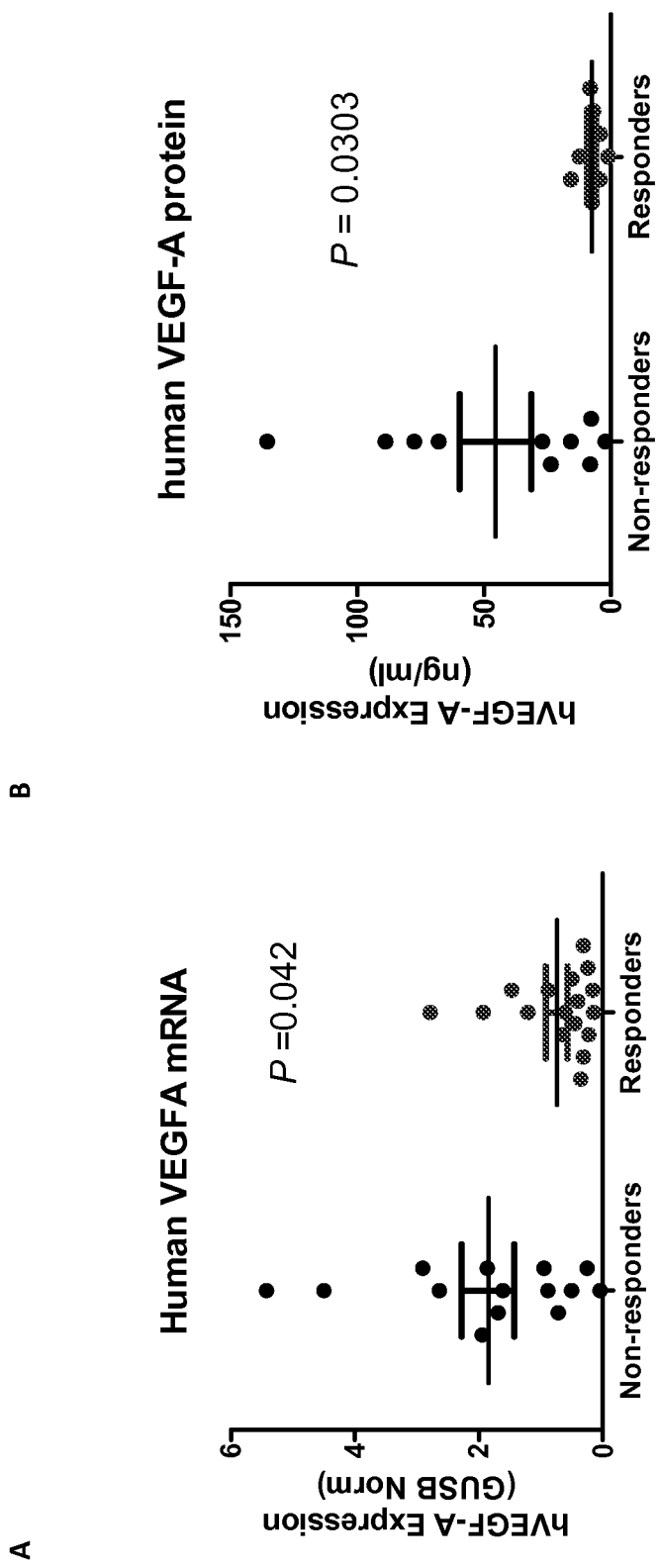
FIG. 9A-B show (A) VEGFA mRNA (normalized to GUSB) and (B) VEGFA protein expression (normalized to total protein) in FGFR1-ECD.339-Fc responder and non-responder xenografts, as described in Example 9.

FIG. 9 shows (A) VEGFA mRNA (normalized to GUSB) and (B) VEGFA protein expression in FGFR1-ECD.339-Fc responder and non-responder xenografts. Expression of VEGFA (P=0.042) was negatively associated with FGFR1-ECD.339-Fc response. VEGFA protein levels were also confirmed to negatively correlate with FGFR1-ECD.339-Fc response (p=0.0303).

Example 10: FGF2 and VEGF Levels in Mesothelioma Cell Lines

FGF2 and VEGF mRNA expression level data was acquired from the Cancer Cell Line Encyclopedia (CCLE; www.broadinstitute.org/ccle/home) and compiled for 12 mesothelioma cell lines. CCLE mRNA data was derived using Affymetrix U133+2 arrays. Raw Affymetrix CEL files were converted to a single value for each probe set using Robust Multi-array Average (RMA) and normalized using quantile normalization. See, e.g., Irizarry, R. A. et al. Exploration, normalization, and summaries of high density oligonucleotide array probe level data. *Biostatistics* 4, 249-264, (2003); Bolstad, B. M., Irizarry, R. A., Astrand, M. & Speed, T. P. A comparison of normalization methods for high density oligonucleotide array data based on variance and bias. *Bioinformatics* 19, 185-193, (2003). The specific probe set IDs for each gene are as follows: FGF2 (2247_at); VEGF (7422_at). In the CCLE, mesothelioma cell lines have one of the highest levels of FGF2 mRNA compared to other cancer cell lines. (Data not shown) Further, as shown in Table 5, FGF2 mRNA levels are higher than VEGF levels in 11 out of 12 mesothelioma cell lines analyzed.

TABLE 5

FGF2 and VEGF levels from CCLE for mesothelioma cell lines

| Mesothelioma cell line | FGF2 mRNA | VEGF mRNA |
|---|---|---|
| MSTO-211H | 10.67467 | 7.594727 |
| RS5 | 10.60627 | 9.440938 |
| ISTMES1 | 10.30963 | 7.107872 |
| MPP89 | 10.12146 | 7.619482 |
| NCI-H226 | 9.905197 | 7.045242 |
| NCI-H2052 | 9.808463 | 6.856421 |
| NCI-H2452 | 9.446462 | 7.908656 |
| JL1 | 9.411504 | 8.830768 |
| ISTMES2 | 9.098945 | 7.419612 |
| DM3 | 8.865603 | 7.968453 |
| ACCMESO1 | 8.663109 | 7.583632 |
| NCI-H28 | 8.01711 | 9.426254 |

Example 11: Administration of FGFR1-ECD.339-Fc in Mesothelioma Tumor Xenograft Models Seven week old female SCID mice (Taconic, Hudson, N.Y.) were implanted subcutaneously with NCI-H226 cells (ATCC, Manassas, Va.) at $5 \times 10^6$ cells/mouse and tumor-bearing mice were randomized into 4 groups (n=8/group) when tumors reached ~176-277 mm³ in size. Mice were treated with FGFR1-ECD.339-Fc at three different concentrations (1.024, 5.12 or 25.6 mg/kg) three times a week (t.i.w.) for 29 days. Tumor size and body weights were measured twice a week.

Figure 10:
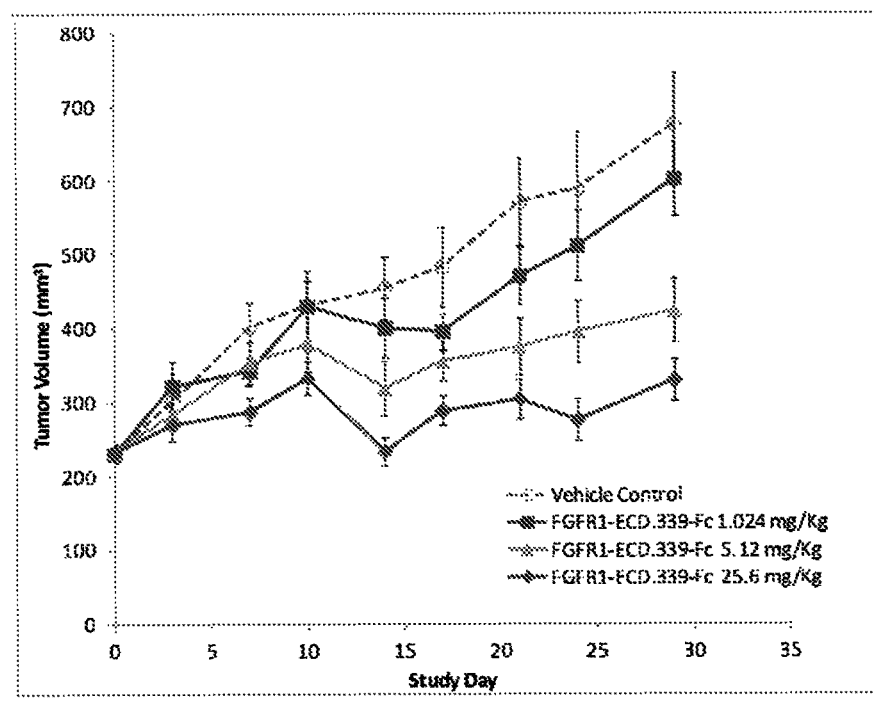
FIG. 10 show mean tumor volume at various time points in mice implanted with NCI-H226 cells and treated with FGFR1-ECD.339-Fc, as described in Example 11.

As shown in FIG. 10, tumor growth inhibition (TGI) was observed at day 29 in mice treated with of FGFR1-ECD.339-Fc at 1.024 mg/kg (16.2% TGI), 5.12 mg/kg (56.8% TGI) and 25.6 mg/kg (77.8% TGI).

Five to six week old female SCID mice were implanted subcutaneously with MSTO-211H cells (ATCC, Manassas, Va.) at $5 \times 10^6$ cells/mouse and tumor-bearing mice were randomized into 3 groups (n=10/group) when tumors reached ~150-225 mm³ in size. Mice were treated with FGFR1-ECD.339-Fc at two different concentrations (5.12 or 25.6 mg/kg) three times a week (t.i.w.) for 29 days. Tumor size and body weights were measured twice a week.

Figure 11:
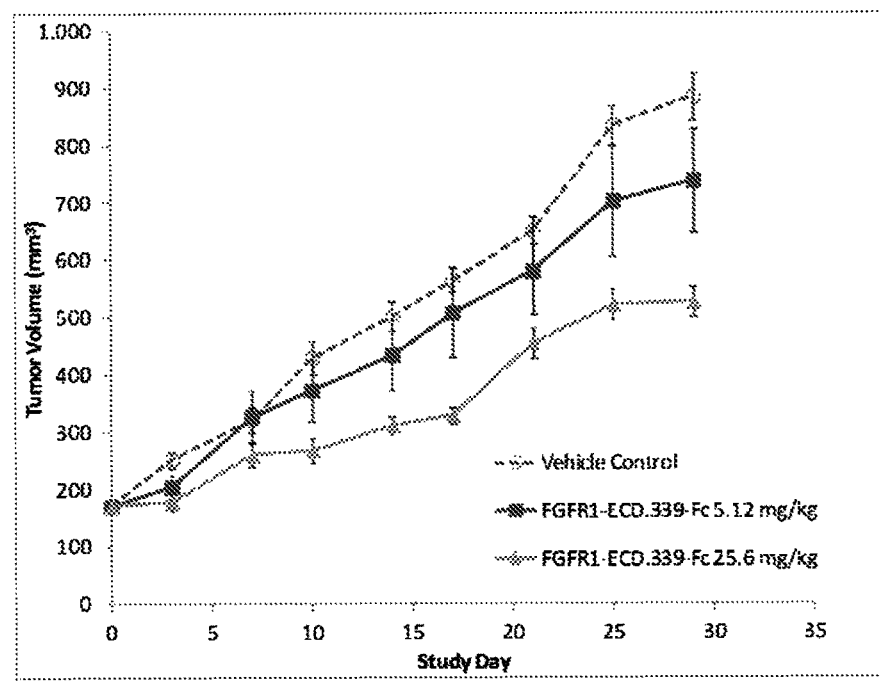
FIG. 11 show mean tumor volume at various time points in mice implanted with MSTO-211H cells and treated with FGFR1-ECD.339-Fc, as described in Example 11.

As shown in FIG. 11, tumor growth inhibition (TGI) was observed at day 29 in mice treated with of FGFR1-ECD.339-Fc at 5.12 mg/kg (20.3% TGI) and 25.6 mg/kg (50.1% TGI).

Endothelial cell immunohistochemical (IHC) staining using a rat anti-mouse pan-endothelial cell antigen antibody (MECA-32; BD Biosciences, Franklin Lakes, N.J.) was performed on tumors from a NCI-H226 (mesothelioma) xenograft study. Tumor-bearing mice were treated with either vehicle (0.9% saline) or increasing doses of FGFR1-ECD.339-Fc (1.024, 5.12, or 25.6 mg/kg) three times a week (t.i.w.) for 29 days, as described above. Tumors were harvested on day 30. Quantification of MECA-32 IHC staining was analyzed by measuring the number of blood vessels/tissue area.

Figure 12:
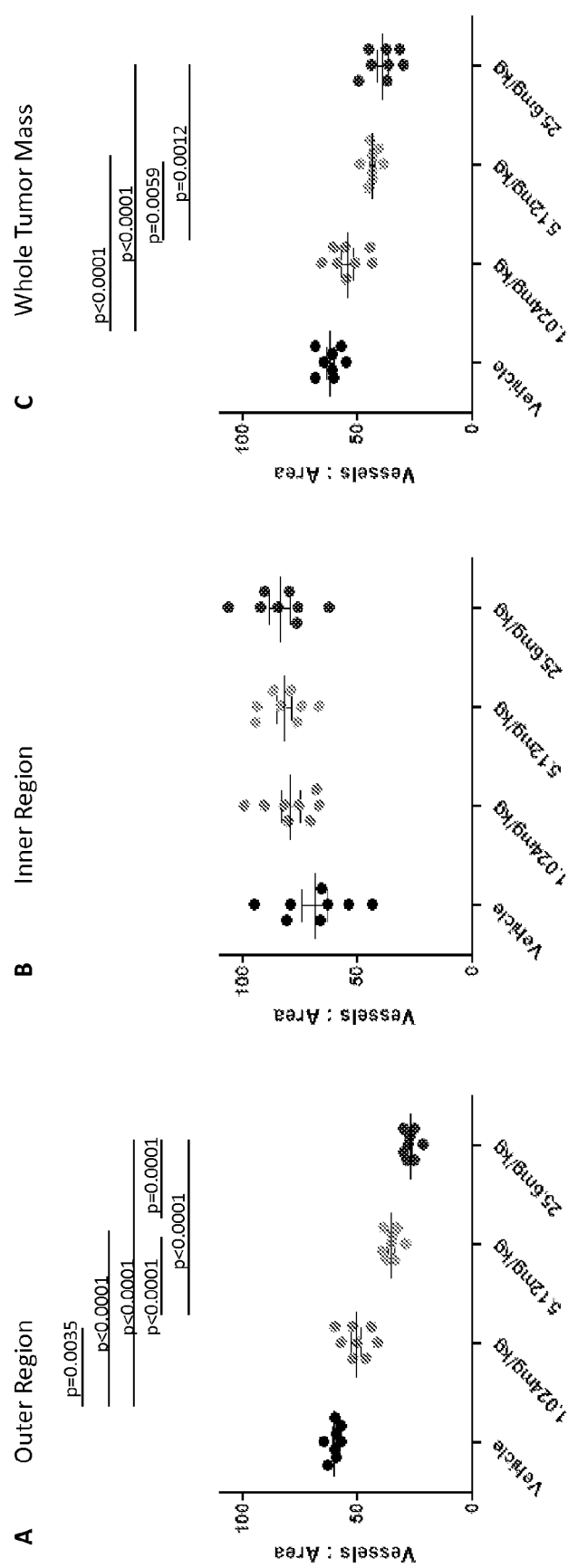
FIG. 12A-C show vessel area determined by immunohistochemistry in mice implanted with NCI-H226 cells and treated with FGFR1-ECD.339-Fc as described in Example 11.

As shown in FIG. 12, a dose-dependent and a statistically-significant reduction in blood vessel density with FGFR1-ECD.339-Fc treatment was observed using the outer region data (A) and the outer+inner region data sets (whole tumor mass; C). In this experiment, no significant differences were demonstrated with the inner region data set (B).

Another nonlimiting exemplary method of measuring blood vessel density by IHC uses antibodies that recognize CD31/PECAM-1.

Example 12: Administration of FGFR1-ECD.339-Fc in HLF Tumor Xenograft Models

Six week old female CB17 SCID mice were purchased from Charles River Laboratories (Wilmington, Mass.) and were acclimated for 1 week before the start of the study. Human hepatocellular carcinoma (HCC) cell line HLF was purchased from JCRB (Cat. No. JCRB0405). The cells were cultured for three passages in complete growth medium to expand for implantation. HLF cells were cultured in Dulbecco's Modified Eagle Medium (DMEM) supplemented with 10% Fetal Bovine Serum (FBS) and Antibiotic-Antimycotic solution. Cells were grown at 37° C. in a humidified atmosphere with 5% $CO_2$.

When the cultured cells reached 85-90% confluence, cells were harvested and resuspended in cold $Ca^{2+}$ and $Mg^{2+}$ free phosphate buffered saline (PBS) containing 50% Matrigel at $2.5 \times 10^7$ cells per milliliter. The cells were implanted subcutaneously over the right flank of the mice at $2.5 \times 10^6$ cells/100 µl/mouse. Mice were monitored twice weekly following cell implantation for tumor growth. Once HLF tumors reached an average size of 100 $mm^3$, according to the formula Tumor size $(mm^3)$=(width (mm)×length $(mm))^2/2$, mice were sorted and randomized into one of four treatment group and dosing was initiated. The first tumors reached this volume in approximately 2 months. Tumor-bearing mice continued to be added to the in vivo study as they reached a volume of approximately 100 $mm^3$ (n=8-10 per group).

FGFR1-ECD.339-Fc or albumin as a negative control, was dosed at 15 mg/kg via intraperitoneal (IP) injection twice per week. Sorafenib (Nexavar®) was dosed at 20 mg/kg via oral gavage daily, five times per week. As a control for sorafenib treatment, animals were dosed via daily gavage with vehicle (1% DMSO/19% 1:1 cremophor/ethanol/80% water). Upon initiation of therapy, tumor sizes were measured in each mouse twice weekly. The length and width of each tumor was measured using calipers and the tumor size calculated according to the formula above. Mice were euthanized when the subcutaneous tumor volumes exceeded 1500 $mm^3$, when the tumors became excessively necrotic, or when animal health became compromised.

Comparisons of tumor volume as a consequence of treatment with FGFR1-ECD.339-Fc and/or sorafenib were determined to be statistically significant if $P<0.05$. P-values were calculated using unpaired, two-tailed t-test analyses of the calculated tumor volumes on day 24 following initiation of treatment.

Figure 13:
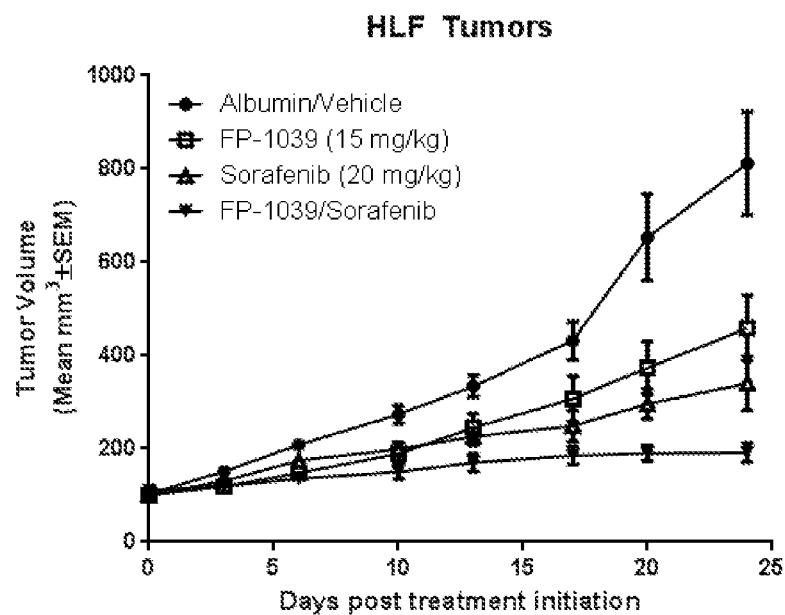
FIG. 13A-B show (A) mean tumor volume at various time points, and (B) final tumor volume, in mice implanted with HLF cells and treated with FGFR1-ECD.339-Fc ("FP-1039"), sorafenib, FGFR1-ECD.339-Fc ("FP-1039") and sorafenib, or albumin, as described in Example 12.
Figure 13:
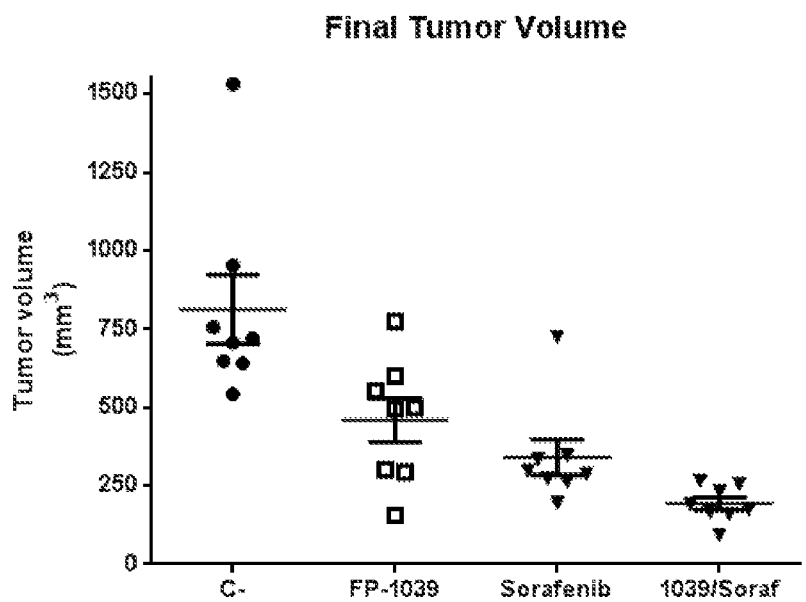

FIG. 13 shows the results of this experiment. The HLF xenograft model (high FGF2, low VEGF; FGF2/VEGF=1.23; see Table 3) responded to FGFR1-ECD.339-Fc ("FP-1039") as a single therapy ($p=0.0175$ at 24 days), and also responded to sorafenib as a single agent therapy ($p=0.0020$ at 24 days). See FIGS. 13A and B. The combination of FGFR1-ECD.339-Fc and sorafenib significantly increased tumor growth inhibition over sorafenib alone ($p=0.0289$) or over FGFR1-ECD.339-Fc alone ($p=0.0026$). See id. This analysis demonstrated that FGFR1-ECD.339-Fc alone inhibited tumor growth in the HLF xenograft model, which has high FGF2 and low VEGF, and that the combination of FGFR1-ECD.339-Fc and sorafenib significantly increased tumor growth inhibition over sorafenib or FGFR1-ECD.339-Fc alone.

Table of Sequences

The following table lists certain sequences discussed herein. FGFR1 sequences are shown without the signal peptide, unless otherwise indicated.

Sequences and Descriptions

| SEQ ID NO | Description | Sequence |
|---|---|---|
| 1 | Full-length human FGFR1 ECD (with signal peptide); SP-hFGFR1-ECD.353 | MWSWKCLLFW AVLVTATLCT ARPSPTLPEQ AQPWGAPVEV ESFLVHPGDL LQLRCRLRDD VQSINWLRDG VQLAESNRTR ITGEEVEVQD SVPADSGLYA CVTSSPSGSD TTYFSVNVSD ALPSSEDDDD DDDSSSEEKE TDNTKPNPVA PYWTSPEKME KKLHAVPAAK TVKFKCPSSG TPNPTLRWLK NGKEFKPDHR IGGYKVRYAT WSIIMDSVVP SDKGNYTCIV ENEYGSINHT YQLDVVERSP HRPILQAGLP ANKTVALGSN VEFMCKVYSD PQPHIQWLKH IEVNGSKIGP DNLPYVQILK TAGVNTIDKE MEVLHLRNVS FEDAGEYTCL AGNSIGLSHH SAWLTVLEAL EERPAVMTSP LYLE |
| 2 | Full-length human FGFR1 ECD (without signal peptide); hFGFR1-ECD.353 | RPSPTLPEQ AQPWGAPVEV ESFLVHPGDL LQLRCRLRDD VQSINWLRDG VQLAESNRTR ITGEEVEVQD SVPADSGLYA CVTSSPSGSD TTYFSVNVSD ALPSSEDDDD DDDSSSEEKE TDNTKPNPVA PYWTSPEKME KKLHAVPAAK TVKFKCPSSG TPNPTLRWLK NGKEFKPDHR IGGYKVRYAT WSIIMDSVVP SDKGNYTCIV ENEYGSINHT YQLDVVERSP HRPILQAGLP ANKTVALGSN VEFMCKVYSD PQPHIQWLKH IEVNGSKIGP DNLPYVQILK TAGVNTIDKE MEVLHLRNVS FEDAGEYTCL AGNSIGLSHH SAWLTVLEAL EERPAVMTSP LYLE |
| 3 | SP-hFGFR1-ECD.339 | MWSWKCLLFW AVLVTATLCT ARPSPTLPEQ AQPWGAPVEV ESFLVHPGDL LQLRCRLRDD VQSINWLRDG VQLAESNRTR ITGEEVEVQD SVPADSGLYA CVTSSPSGSD TTYFSVNVSD ALPSSEDDDD DDDSSSEEKE TDNTKPNPVA PYWTSPEKME KKLHAVPAAK TVKFKCPSSG TPNPTLRWLK NGKEFKPDHR IGGYKVRYAT WSIIMDSVVP SDKGNYTCIV ENEYGSINHT YQLDVVERSP HRPILQAGLP ANKTVALGSN VEFMCKVYSD PQPHIQWLKH IEVNGSKIGP DNLPYVQILK TAGVNTIDKE MEVLHLRNVS FEDAGEYTCL AGNSIGLSHH SAWLTVLEAL |
| 4 | hFGFR1-ECD.339 | RPSPTLPEQ AQPWGAPVEV ESFLVHPGDL LQLRCRLRDD VQSINWLRDG VQLAESNRTR ITGEEVEVQD SVPADSGLYA CVTSSPSGSD TTYFSVNVSD ALPSSEDDDD DDDSSSEEKE TDNTKPNPVA PYWTSPEKME KKLHAVPAAK TVKFKCPSSG TPNPTLRWLK NGKEFKPDHR IGGYKVRYAT WSIIMDSVVP SDKGNYTCIV ENEYGSINHT YQLDVVERSP HRPILQAGLP ANKTVALGSN VEFMCKVYSD PQPHIQWLKH IEVNGSKIGP |

| SEQ ID NO | Description | Sequence |
|---|---|---|
| | | DNLPYVQILK TAGVNTIDKE MEVLHLRNVS FEDAGEYTCL AGNSIGLSHH SAWLTVLEAL |
| 5 | SP-hFGFR1-ECD.339-Fc | MWSWKCLLFW AVLVTATLCT ARPSPTLPEQ AQPWGAPVEV ESFLVHPGDL LQLRCRLRDD VQSINWLRDG VQLAESNRTR ITGEEVEVQD SVPADSGLYA CVTSSPSGSD TTYFSVNVSD ALPSSEDDDD DDDSSSEEKE TDNTKPNPVA PYWTSPEKME KKLHAVPAAK TVKFKCPSSG TPNPTLRWLK NGKEFKPDHR IGGYKVRYAT WSIIMDSVVP SDKGNYTCIV ENEYGSINHT YQLDVVERSP HRPILQAGLP ANKTVALGSN VEFMCKVYSD PQPHIQWLKH IEVNGSKIGP DNLPYVQILK TAGVNTIDKE MEVLHLRNVS FEDAGEYTCL AGNSIGLSHH SAWLTVLEAL EPKSSDKTHT CPPCPAPELL GGPSVFLFPP KPKDTLMISR TPEVTCVVVD VSHEDPEVKF NWYVDGVEVH NAKTKPREEQ YNSTYRVVSV LTVLHQDWLN GKEYKCKVSN KALPAPIEKT ISKAKGQPRE PQVYTLPPSR DELTKNQVSL TCLVKGFYPS DIAVEWESNG QPENNYKTTP PVLDSDGSFF LYSKLTVDKS RWQQGNVFSC SVMHEALHNH YTQKSLSLSP GK |
| 6 | hFGFR1-ECD.339-Fc | RPSPTLPEQ AQPWGAPVEV ESFLVHPGDL LQLRCRLRDD VQSINWLRDG VQLAESNRTR ITGEEVEVQD SVPADSGLYA CVTSSPSGSD TTYFSVNVSD ALPSSEDDDD DDDSSSEEKE TDNTKPNPVA PYWTSPEKME KKLHAVPAAK TVKFKCPSSG TPNPTLRWLK NGKEFKPDHR IGGYKVRYAT WSIIMDSVVP SDKGNYTCIV ENEYGSINHT YQLDVVERSP HRPILQAGLP ANKTVALGSN VEFMCKVYSD PQPHIQWLKH IEVNGSKIGP DNLPYVQILK TAGVNTIDKE MEVLHLRNVS FEDAGEYTCL AGNSIGLSHH SAWLTVLEAL EPKSSDKTHT CPPCPAPELL GGPSVFLFPP KPKDTLMISR TPEVTCVVVD VSHEDPEVKF NWYVDGVEVH NAKTKPREEQ YNSTYRVVSV LTVLHQDWLN GKEYKCKVSN KALPAPIEKT ISKAKGQPRE PQVYTLPPSR DELTKNQVSL TCLVKGFYPS DIAVEWESNG QPENNYKTTP PVLDSDGSFF LYSKLTVDKS RWQQGNVFSC SVMHEALHNH YTQKSLSLSP GK |
| 7 | hFGFR1 signal peptide | MWSWKCLLFWAVLVTATLCTA |
| 8 | Fc C237S | EPKSSDKTHT CPPCPAPELL GGPSVFLFPP KPKDTLMISR TPEVTCVVVD VSHEDPEVKF NWYVDGVEVH NAKTKPREEQ YNSTYRVVSV LTVLHQDWLN GKEYKCKVSN KALPAPIEKT ISKAKGQPRE PQVYTLPPSR DELTKNQVSL TCLVKGFYPS DIAVEWESNG QPENNYKTTP PVLDSDGSFF LYSKLTVDKS RWQQGNVFSC SVMHEALHNH YTQKSLSLSP GK |
| 9 | Exemplary Fc #1 | ERKCCVECPP CPAPPVAGPS VFLFPPKPKD TLMISRTPEV TCVVVDVSHE DPEVQFNWYV DGVEVHNAKT KPREEQFNST FRVVSVLTVV HQDWLNGKEY KCKVSNKGLP APIEKTISKT KGQPREPQVY TLPPSREEMT KNQVSLTCLV KGFYPSDIAV EWESNGQPEN NYKTTPPMLD SDGSFFLYSK LTVDKSRWQQ GNVFSCSVMH EALHNHYTQK SLSLSPGK |
| 10 | Exemplary Fc #2 | ESKYGPPCPS CPAPEFLGGP SVFLFPPKPK DTLMISRTPE VTCVVVDVSQ EDPEVQFNWY VDGVEVHNAK TKPREEQFNS TYRVVSVLTV LHQDWLNGKE YKCKVSNKGL PSSIEKTISK AKGQPREPQV YTLPPSQEEM TKNQVSLTCL VKGFYPSDIA VEWESNGQPE NNYKTTPPVL DSDGSFFLYS RLTVDKSRWQ EGNVFSCSVM HEALHNHYTQ KSLSLSLGK |

The invention claimed is:

1. A method of treating mesothelioma comprising administering to a human subject with mesothelioma an effective amount of a fibroblast growth factor receptor 1 (FGFR1) extracellular domain (ECD) or FGFR1 ECD fusion molecule and at least one therapeutic agent selected from paclitaxel, carboplatin, docetaxel, pemetrexed, and cisplatin, wherein the mesothelioma has a higher level of fibroblast growth factor 2 (FGF2) mRNA compared to vascular endothelial growth factor (VEGF) mRNA or a higher level of FGF2 protein compared to VEGF protein.

2. The method of claim 1, wherein the method comprises administering an effective amount of an FGFR1 ECD or FGFR1 ECD fusion molecule, paclitaxel and carboplatin.

3. The method of claim 1, wherein the method comprises administering an effective amount of an FGFR1 ECD or FGFR1 ECD fusion molecule and docetaxel.

4. The method of claim 1, wherein the method comprises administering an effective amount of an FGFR1 ECD or FGFR1 ECD fusion molecule, pemetrexed, and cisplatin.

5. The method of claim 1, wherein administration of the FGFR1 ECD or FGFR1 ECD fusion molecule and at least one therapeutic agent reduces blood vessel density in the mesothelioma.

6. The method of claim 1, wherein the mesothelioma has a higher level of FGF2 compared to a level of FGF2 in a non-cancerous mesothelial reference sample or cell.

7. The method of claim 1, wherein the mesothelioma has a higher level of FGF2 mRNA compared to VEGF mRNA.

8. The method of claim 1, wherein the mesothelioma has a higher level of FGF2 protein compared to VEGF protein.

9. The method of claim 1, wherein the method comprises administering an FGFR1 ECD.

10. The method of claim 9, wherein the FGFR1 ECD comprises an amino acid sequence selected from SEQ ID NOs: 1 to 4.

11. The method of claim 1, wherein the method comprises administering an FGFR1 ECD fusion molecule.

12. The method of claim 11, wherein the FGFR1 ECD fusion molecule comprises an FGFR1 ECD and a fusion partner, and wherein the fusion partner is Fc.

13. The method of claim 12, wherein the FGFR1 ECD fusion molecule comprises a sequence selected from SEQ ID NO: 5 and SEQ ID NO: 6.

14. The method of claim 13, wherein the FGFR1 ECD fusion molecule comprises the sequence of SEQ ID NO: 6.

15. The method of claim 4, wherein the method comprises administering an FGFR1 ECD fusion molecule.

16. The method of claim 15, wherein the FGFR1 ECD fusion molecule comprises an FGFR1 ECD and a fusion partner, and wherein the fusion partner is Fc.

17. The method of claim 16, wherein the FGFR1 ECD fusion molecule comprises a sequence selected from SEQ ID NO: 5 and SEQ ID NO: 6.

18. The method of claim 11, wherein the FGFR1 ECD fusion molecule is administered at a dose of 5-20 mg/kg.

19. The method of claim 11, wherein the FGFR1 ECD fusion molecule is administered weekly.

* * * * *